United States Patent
Gan et al.

(12)

(10) Patent No.: US 6,743,904 B2
(45) Date of Patent: Jun. 1, 2004

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Weiniu Gan, Gaithersburg, MD (US); Jane Ye, Boyds, MD (US); Valentina Di Francesco, Rockville, MD (US); Ellen M Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 280 days.

(21) Appl. No.: 09/805,455

(22) Filed: Mar. 14, 2001

(65) Prior Publication Data

US 2003/0166203 A1 Sep. 4, 2003

(51) Int. Cl.[7] ......................... C07H 21/02; C07H 21/04; C12Q 1/68; C12P 21/00
(52) U.S. Cl. ......................... 536/23.1; 536/24.3; 435/6; 435/69.1
(58) Field of Search .............................. 536/23.1, 24.3; 435/6, 69.1

(56) References Cited

FOREIGN PATENT DOCUMENTS

WO     WO 98 53601 A1    11/1998

OTHER PUBLICATIONS

Guru et al, "A transcript map for the 2.8 Mb region containing the multiple endocrine neoplasia type 1 locus", Genome Research (1997) 7:725–735.*

Kawasaki et al. "A Rap Guanine Nucleotide Exchange Factor Enriched Highly in Basal Ganglia." Proc. Natl. Acad. Sci. Oct. 1998. vol. 95, pp. 13278–13283.

Clyde–Smith et al. "Characterization of RasGRP2. a Plasma Membrane–Targeted Dual Specifically Ras/Rap Exchange Factor." J. Biol. Chem. Oct. 13, 2000. vol. 275, No. 41, pp. 32260–32267.

Kedra et al. "The Germinal Center Kinase Gene and a Novel CDC–25 Like Gene are Located in the Vicinity of the PYGM Gene on 11q13." Human Genet. 1997. vol. 100, pp. 611–619.

Guru et al. "A Transcript Map for the 2.8 Mb Region Containing the Multiple Endocrine Neoplasia Type 1 Locus." Genome Research. 1997. vol. 7, pp. 725–735.

International Search report dated May 22, 2003.

* cited by examiner

*Primary Examiner*—Jeffrey Fredman
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

9 Claims, 21 Drawing Sheets

```
   1 TCCTCCGGTC GCCCGCCCTC GGGGCAGCTA GTGGCGCAGC CCCCCGCCCG
  51 CGGCCCTGGC CTCCCGGGCG GCGCGGCAGG GGAGGGGTTA AGCTGCCGCA
 101 GGGACCGCCG CGTGCGGGGC GAGAGGGAGC CCCCGGTGGG GGTGGCGCAG
 151 CCGGCGGGGT TCGGTCCGAG CCCGGTGGGA GGCTCCCGGA GCGCAGCCTG
 201 GGCCCAGCCC ACCCCGCGCC GGCGGCCATG GCAGGCACCC TGGACCTGGA
 251 CAAGGGCTGC ACGGTGGAGG AGCTGCTCCG CGGGTGCATC GAAGCCTTCG
 301 ATGACTCCGG GAAGGTGCGG GACCCGCAGC TGGTGCGCAT ATTCCTCATG
 351 ATGCACCCCT GGTACATCCC CTCCTCTCAG CTGGCGGCCA AGCTGCTCCA
 401 CATCTACCAA CAATCCCGGA AGGACAACTC CAATTCCCTG CAGGTGAAAA
 451 CGTGCCACCT GGTCAGGTAC TGGATCTCCG CCTTCCCAGC GGAGTTTGAC
 501 TTGAACCCGG AGTTGGCTGA GCAGATCAAG GAGCTGAAGG CTCTGCTAGA
 551 CCAAGAAGGG AACCGACGGC ACAGCAGCCT AATCGACATA GACAGCGTCC
 601 CTACCTACAA GTGGAAGCGG CAGGTGACTC AGCGGAACCC TGTGGGACAG
 651 AAAAAGCGCA AGATGTCCCT GTTGTTTGAC CACCTGGAGC CCATGGAGCT
 701 GGCGGAGCAT CTCACCTACT GGAGTATCG CTCCTTCTGC AAGATCCTGT
 751 TTCAGGACTA TCACAGTTTC GTGACTCATG GCTGCACTGT GGACAACCCC
 801 GTCCTGGAGC GGTTCATCTC CCTCTTCAAC AGCGTCTCAC AGTGGGTGCA
 851 GCTCATGATC CTCAGCAAAC CCACAGCCCC GCAGCGGGCC CTGGTCATCA
 901 CACACTTTGT CCACGTGGCG GAGAAGCTGC TACAGCTGCA GAACTTCAAC
 951 ACGCTGATGG CAGTGGTCGG GGGCCTGAGC CACAGCTCCA TCTCCCGCCT
1001 CAAGGAGACC CACAGCCACG TTAGCCCTGA GACCATCAAG CTCTGGGAGG
1051 GTCTCACGGA ACTAGTGACG GCGACAGGCA ACTATGGCAA CTACCGGCGT
1101 CGGCTGGCAG CCTGTGTGGG CTTCCGCTTC CCGATCCTGG GTGTGCACCT
1151 CAAGGACCTG GTGGCCCTGC AGCTGGCACT GCCTGACTGG CTGGACCCAG
1201 CCCGGACCCG GCTCAACGGG GCCAAGATGA AGCAGCTCTT TAGCATCCTG
1251 GAGGAGCTGG CCATGGTGAC CAGCCTGCGG CCACCAGTAC AGGCCAACCC
1301 CGACCTGCTG AGCCTGCTCA CGGTGTCTCT GGATCAGTAT CAGACGGAGG
1351 ATGAGCTGTA CCAGCTGTCC CTGCAGCGGG AGCCGCGCTC CAAGTCCTCG
1401 CCAACCAGCC CCACGAGTTG CACCCCACCA CCCCGGCCCC CGGTACTGGA
1451 GGAGTGGACC TCGGCTGCCA AACCCAAGCT GGATCAGGCC CTCGTGGTGG
1501 AGCACATCGA AAGATGGTG GAGTCTGTGT TCCGGAACTT TGACGTCGAT
1551 GGGGATGGCC ACATCTCACA GGAAGAATTC CAGATCATCC GTGGGAACTT
1601 CCCTTACCTC AGCGCCTTTG GGGACCTCGA CCAGAACCAG GATGGCTGCA
1651 TCAGCAGGGA GGAGATGGTT TCCTATTTCC TGCGCTCCAG CTCTGTGTTG
1701 GGGGGCGCA TGGGCTTCGT ACACAACTTC CAGGAGAGCA ACTCCTTGCG
1751 CCCCGTCGCC TGCCGCCACT GCAAAGCCCT GATCCTGGGC ATCTACAAGC
1801 AGGGCCTCAA ATGCCGAGCC TGTGGAGTGA ACTGCCACAA GCAGTGCAAG
1851 GATCGCCTGT CAGTTGAGTG TCGGCGCAGG GCCCAGAGTG TGAGCCTGGA
1901 GGGGTCTGCA CCCTCACCCT CACCCATGCA CAGCCACCAT CACCGCGCCT
1951 TCAGCTTCTC TCTGCCCCGC CCTGGCAGGC GAGGCTCCAG GCCTCCAGCA
2001 ATCCCCCTCC CAGCAGAGAT CCGTGAGGAG GAGGTACAGA CGGTGGAGGA
2051 TGGGGTGTTT GACATCCACT TGTAATAGAT GCTGTGGTTG GATCAAGGAC
2101 TCATTCCTGC CTTGGAGAAA ATACTTCAAC CAGAGCAGGG AGCCTGGGGG
2151 TGTCGGGGCA GGAGGCTGGG GATGGGGTG GGATATGAGG GTGGCATGCA
2201 GCTGAGGGCA GGGCCAGGGC TGGTGTCCCT AAGGTTGTAC AGACTCTTGT
2251 GAATATTTGT ATTTTCCAGA TGGAATAAAA AGGCCCGTGT AATTAAAAAA
2301 AAAAAAAAAA AAAAAAAAAA AAAAAAAAAA AAAAAAAAAA AAAAAAAA    (SEQ ID NO:1)
```

FEATURES:
5'UTR:        1-227
Start Codon:  228
Stop Codon:   2073
3'UTR:        2076

FIGURE 1

Homologous proteins:
Top 10 BLAST Hits

|  | Score | E |
|---|---|---|
| CRA\|1000682340958 /altid=gi\|6358505 /def=gb\|AAF07219.1\|AF043722... | 1293 | 0.0 |
| CRA\|18000005086608 /altid=gi\|5031623 /def=ref\|NP_005816.1\| RAS ... | 1241 | 0.0 |
| CRA\|18000005188697 /altid=gi\|6755290 /def=ref\|NP_035372.1\| RAS,... | 1202 | 0.0 |
| CRA\|18000005205935 /altid=gi\|7662334 /def=ref\|NP_056191.1\| KIAA... | 618 | e-175 |
| CRA\|18000005188699 /altid=gi\|3928857 /def=gb\|AAC79700.1\| (AF081... | 533 | e-150 |
| CRA\|18000005152782 /altid=gi\|9507035 /def=ref\|NP_062084.1\| RAS ... | 531 | e-149 |
| CRA\|18000005192860 /altid=gi\|7242201 /def=ref\|NP_035376.1\| RAS ... | 529 | e-149 |
| CRA\|18000005192861 /altid=gi\|4038292 /def=gb\|AAC97349.1\| (AF106... | 526 | e-148 |
| CRA\|18000005188698 /altid=gi\|5032025 /def=ref\|NP_005730.1\| RAS ... | 525 | e-148 |
| CRA\|1000733831533 /altid=gi\|6650545 /def=gb\|AAF21898.1\|AF081197... | 525 | e-148 |

BLAST dbEST hits:

|  | Score | E |
|---|---|---|
| gi\|5432583 /dataset=dbest /taxon=9606 ... | 1310 | 0.0 |
| gi\|9876673 /dataset=dbest /taxon=960... | 1281 | 0.0 |
| gi\|11286864 /dataset=dbest /taxon=96... | 1249 | 0.0 |
| gi\|11285315 /dataset=dbest /taxon=96... | 1207 | 0.0 |
| gi\|5432584 /dataset=dbest /taxon=9606 ... | 733 | 0.0 |
| gi\|4372300 /dataset=dbest /taxon=9606 ... | 720 | 0.0 |
| gi\|12295751 /dataset=dbest /taxon=96... | 700 | 0.0 |
| gi\|12288965 /dataset=dbest /taxon=96... | 599 | e-168 |
| gi\|6920402 /dataset=dbest /taxon=960... | 573 | e-161 |
| gi\|2005039 /dataset=dbest /taxon=9606 ... | 573 | e-161 |

EXPRESSION INFORMATION FOR MODULATORY USE:
library source:
From BLAST dbEST hits:

| gi\|5432583 | Testis |
| gi\|9876673 | Liver-non-cancerous |
| gi\|11286864 | Brain glioblastoma |
| gi\|11285315 | Brain glioblastoma |
| gi\|5432584 | Testis |
| gi\|4372300 | B Cell Chronic lymphatic leukemia |
| gi\|12295751 | Adult marrow |
| gi\|12288965 | Adult marrow |
| gi\|6920402 | Lymph germinal center B cell |
| gi\|2005039 | Lymph |

From tissue screening panels:
Leukocyte

FIGURE 1

```
  1 MAGTLDLDKG CTVEELLRGC IEAFDDSGKV RDPQLVRIFL MMHPWYIPSS
 51 QLAAKLLHIY QQSRKDNSNS LQVKTCHLVR YWISAFPAEF DLNPELAEQI
101 KELKALLDQE GNRRHSSLID IDSVPTYKWK RQVTQRNPVG QKKRKMSLLF
151 DHLEPMELAE HLTYLEYRSF CKILFQDYHS FVTHGCTVDN PVLERFISLF
201 NSVSQWVQLM ILSKPTAPQR ALVITHFVHV AEKLLQLQNF NTLMAVVGGL
251 SHSSISRLKE THSHVSPETI KLWEGLTELV TATGNYGNYR RRLAACVGFR
301 FPILGVHLKD LVALQLALPD WLDPARTRLN GAKMKQLFSI LEELAMVTSL
351 RPPVQANPDL LSLLTVSLDQ YQTEDELYQL SLQREPRSKS SPTSPTSCTP
401 PPRPPVLEEW TSAAKPKLDQ ALVVEHIEKM VESVFRNFDV DGDGHISQEE
451 FQIIRGNFPY LSAFGDLDQN QDGCISREEM VSYFLRSSSV LGGRMGFVHN
501 FQESNSLRPV ACRHCKALIL GIYKQGLKCR ACGVNCHKQC KDRLSVECRR
551 RAQSVSLEGS APSPSPMHSH HHRAFSFSLP RPGRRGSRPP AIPLPAEIRE
601 EEVQTVEDGV FDIHL (SEQ ID NO:2)
```

FEATURES:
Functional domains and key regions:
[1] PDOC00004 PS00004 CAMP_PHOSPHO_SITE
cAMP- and cGMP-dependent protein kinase phosphorylation site Number of matches: 3
    1    113-116    RRHS
    2    144-147    RKMS
    3    584-587    RRGS

[2] PDOC00005 PS00005 PKC_PHOSPHO_SITE
Protein kinase C phosphorylation site

Number of matches: 7
    1     27-29    SGK
    2     63-65    SRK
    3    126-128   TYK
    4    134-136   TQR
    5    269-271   TIK
    6    349-351   SLR
    7    506-508   SLR

[3] PDOC00006 PS00006 CK2_PHOSPHO_SITE
Casein kinase II phosphorylation site

Number of matches: 9
    1     12-15    TVEE
    2     63-66    SRKD
    3    117-120   SLID
    4    163-166   TYLE
    5    339-342   SILE
    6    373-376   TEDE
    7    447-450   SQEE
    8    476-479   SREE
    9    605-608   TVED

[4] PDOC00008 PS00008 MYRISTYL
N-myristoylation site

Number of matches: 4
    1     19-24    GCIEAF
    2    249-254   GLSHSS
    3    284-289   GNYGNY
    4    492-497   GGRMGF

FIGURE 2

[5] PDOC00009 PS00009 AMIDATION
Amidation site 582-585 PGRR

[6] PDOC00018 PS00018 EF_HAND
EF-hand calcium-binding domain

Number of matches: 2
     1    439-451 DVDGDGHISQEEF
     2    468-480 DQNQDGCISREEM

[7] PDOC00379 PS00479 DAG_PE_BIND_DOM_1
Phorbol esters / diacylglycerol binding domain 499-548 HNFQESNSLRPVACRHCKALILGIYKQGLKCRACGVNCHKQCKDRLSVEC

Membrane spanning structure and domains:
| Helix | Begin | End | Score | Certainty |
|-------|-------|-----|-------|-----------|
| 1     | 34    | 54  | 0.713 | Putative  |
| 2     | 195   | 215 | 0.653 | Putative  |
| 3     | 238   | 258 | 0.788 | Putative  |

FIGURE 2

BLAST Alignment to Top Hit:
```
>CRA|18000005086608 /altid=gi|5031623 /def=ref|NP_005816.1| RAS guanyl
        releasing protein 2 (calcium and DAG-regulated); calcium
        and diacylglycerol-regulated guanine nucleotide exchange
        factor I [Homo sapiens] /org=Homo sapiens /taxon=9606
        /dataset=nraa /length=609
        Length = 609
 Score = 1241 bits (3176), Expect = 0.0
 Identities = 608/615 (98%), Positives = 609/615 (98%)
 Frame = +3

Query: 228  MAGTLDLDKGCTVEELLRGCIEAFDDSGKVRDPQLVRIFLMMHPWYIPSSQLAAKLLHIY 407
            MAGTLDLDKGCTVEELLRGCIEAFDDSGKVRDPQLVR+FLMMHPWYIPSSQLAAKLLHIY
Sbjct: 1    MAGTLDLDKGCTVEELLRGCIEAFDDSGKVRDPQLVRMFLMMHPWYIPSSQLAAKLLHIY 60

Query: 408  QQSRKDNSNSLQVKTCHLVRYWISAFPAEFDLNPELAEQIKELKALLDQEGNRRHSSLID 587
            QQSRKDNSNSLQVKTCHLVRYWISAFPAEFDLNPELAEQIKELKALLDQEGNRRHSSLID
Sbjct: 61   QQSRKDNSNSLQVKTCHLVRYWISAFPAEFDLNPELAEQIKELKALLDQEGNRRHSSLID 120

Query: 588  IDSVPTYKWKRQVTQRNPVGQKKRKMSLLFDHLEPMELAEHLTYLEYRSFCKILFQDYHS 767
            IDSVPTYKWKRQVTQRNPVGQKKRKMSLLFDHLEPMELAEHLTYLEYRSFCKILFQDYHS
Sbjct: 121  IDSVPTYKWKRQVTQRNPVGQKKRKMSLLFDHLEPMELAEHLTYLEYRSFCKILFQDYHS 180

Query: 768  FVTHGCTVDNPVLERFISLFNSVSQWVQLMILSKPTAPQRALVITHFVHVAEKLLQLQNF 947
            FVTHGCTVDNPVLERFISLFNSVSQWVQLMILSKPTAPQRALVITHFVHVAEKLLQLQNF
Sbjct: 181  FVTHGCTVDNPVLERFISLFNSVSQWVQLMILSKPTAPQRALVITHFVHVAEKLLQLQNF 240

Query: 948  NTLMAVVGGLSHSSISRLKETHSHVSPETIKLWEGLTELVTATGNYGNYRRRLAACVGFR 1127
            NTLMAVVGGLSHSSISRLKETHSHVSPETIKLWEGLTELVTATGNYGNYRRRLAACVGFR
Sbjct: 241  NTLMAVVGGLSHSSISRLKETHSHVSPETIKLWEGLTELVTATGNYGNYRRRLAACVGFR 300

Query: 1128 FPILGVHLKDLVALQLALPDWLDPARTRLNGAKMKQLFSILEELAMVTSLRPPVQANPDL 1307
            FPILGVHLKDLVALQLALPDWLDPARTRLNGAKMKQLFSILEELAMVTSLRPPVQANPDL
Sbjct: 301  FPILGVHLKDLVALQLALPDWLDPARTRLNGAKMKQLFSILEELAMVTSLRPPVQANPDL 360

Query: 1308 LSLLTVSLDQYQTEDELYQLSLQREPRSKSSPTSPTSCTPPPRPPVLEEWTSAAKPKLDQ 1487
            LSLLTVSLDQYQTEDELYQLSLQREPRSKSSPTSPTSCTPPPRPPVLEEWTSAAKPKLDQ
Sbjct: 361  LSLLTVSLDQYQTEDELYQLSLQREPRSKSSPTSPTSCTPPPRPPVLEEWTSAAKPKLDQ 420

Query: 1488 ALVVEHIEKMVESVFRNFDVDGDGHISQEEFQIIRGNFPYLSAFGDLDQNQDGCISREEM 1667
            ALVVEHIEKMVESVFRNFDVDGDGHISQEEFQIIRGNFPYLSAFGDLDQNQDGCISREEM
Sbjct: 421  ALVVEHIEKMVESVFRNFDVDGDGHISQEEFQIIRGNFPYLSAFGDLDQNQDGCISREEM 480

Query: 1668 VSYFLRSSSVLGGRMGFVHNFQESNSLRPVACRHCKALILGIYKQGLKCRACGVNCHKQC 1847
            VSYFLRSSSVLGGRMGFVHNFQESNSLRPVACRHCKALILGIYKQGLKCRACGVNCHKQC
Sbjct: 481  VSYFLRSSSVLGGRMGFVHNFQESNSLRPVACRHCKALILGIYKQGLKCRACGVNCHKQC 540

Query: 1848 KDRLSVECRRRAQSVSLEGSAPSPSPMHSHHHRAFSFSLPRPGRRGSRPPAIPLPAEIRE 2027
            KDRLSVECRRRAQSVSLEGSAPSPSPMHSHHHRAFSFSLPRPGRRGSRPP      EIRE
Sbjct: 541  KDRLSVECRRRAQSVSLEGSAPSPSPMHSHHHRAFSFSLPRPGRRGSRPP------EIRE 594

Query: 2028 EEVQTVEDGVFDIHL 2072
            EEVQTVEDGVFDIHL
Sbjct: 595  EEVQTVEDGVFDIHL 609    (SEQ ID NO:4)
```

FIGURE 2

```
>CRA|1000682340958 /altid=gi|6358505 /def=gb|AAF07219.1|AF043722_1
         (AF043722) guanine exchange factor MCG7 isoform 1 [Homo
         sapiens] /org=Homo sapiens /taxon=9606 /dataset=nraa
         /length=671
       Length = 671
 Score = 1293 bits (3309), Expect = 0.0
 Identities = 639/670 (95%), Positives = 643/670 (95%), Gaps = 4/670 (0%)
 Frame = +3

Query: 75    GRGGVKLPQGPPRAGREGAPGGGGAAG----GVRSEPGGRLPERSLGPAHPAPAAMAGTL 242
             GRG   P   + +E   G  +G        GVRSEPGGRLPERSLGPAHPAPAAMAGTL
Sbjct: 8     GRGTQGWPGSSEQHVQEATSSAGLHSGVDELGVRSEPGGRLPERSLGPAHPAPAAMAGTL 67

Query: 243   DLDKGCTVEELLRGCIEAFDDSGKVRDPQLVRIFLMMHPWYIPSSQLAAKLLHIYQQSRK 422
             DLDKGCTVEELLRGCIEAFDDSGKVRDPQLVR+FLMMHPWYIPSSQLAAKLLHIYQQSRK
Sbjct: 68    DLDKGCTVEELLRGCIEAFDDSGKVRDPQLVRMFLMMHPWYIPSSQLAAKLLHIYQQSRK 127

Query: 423   DNSNSLQVKTCHLVRYWISAFPAEFDLNPELAEQIKELKALLDQEGNRRHSSLIDIDSVP 602
             DNSNSLQVKTCHLVRYWISAFPAEFDLNPELAEQIKELKALLDQEGNRRHSSLIDIDSVP
Sbjct: 128   DNSNSLQVKTCHLVRYWISAFPAEFDLNPELAEQIKELKALLDQEGNRRHSSLIDIDSVP 187

Query: 603   TYKWKRQVTQRNPVGQKKRKMSLLFDHLEPMELAEHLTYLEYRSFCKILFQDYHSFVTHG 782
             TYKWKRQVTQRNPVGQKKRKMSLLFDHLEPMELAEHLTYLEYRSFCKILFQDYHSFVTHG
Sbjct: 188   TYKWKRQVTQRNPVGQKKRKMSLLFDHLEPMELAEHLTYLEYRSFCKILFQDYHSFVTHG 247

Query: 783   CTVDNPVLERFISLFNSVSQWVQLMILSKPTAPQRALVITHFVHVAEKLLQLQNFNTLMA 962
             CTVDNPVLERFISLFNSVSQWVQLMILSKPTAPQRALVITHFVHVAEKLLQLQNFNTLMA
Sbjct: 248   CTVDNPVLERFISLFNSVSQWVQLMILSKPTAPQRALVITHFVHVAEKLLQLQNFNTLMA 307

Query: 963   VVGGLSHSSISRLKETHSHVSPETIKLWEGLTELVTATGNYGNYRRRLAACVGFRFPILG 1142
             VVGGLSHSSISRLKETHSHVSPETIKLWEGLTELVTATGNYGNYRRRLAACVGFRFPILG
Sbjct: 308   VVGGLSHSSISRLKETHSHVSPETIKLWEGLTELVTATGNYGNYRRRLAACVGFRFPILG 367

Query: 1143  VHLKDLVALQLALPDWLDPARTRLNGAKMKQLFSILEELAMVTSLRPPVQANPDLLSLLT 1322
             VHLKDLVALQLALPDWLDPARTRLNGAKMKQLFSILEELAMVTSLRPPVQANPDLLSLLT
Sbjct: 368   VHLKDLVALQLALPDWLDPARTRLNGAKMKQLFSILEELAMVTSLRPPVQANPDLLSLLT 427

Query: 1323  VSLDQYQTEDELYQLSLQREPRSKSSPTSPTSCTPPPRPPVLEEWTSAAKPKLDQALVVE 1502
             VSLDQYQTEDELYQLSLQREPRSKSSPTSPTSCTPPPRPPVLEEWTSAAKPKLDQALVVE
Sbjct: 428   VSLDQYQTEDELYQLSLQREPRSKSSPTSPTSCTPPPRPPVLEEWTSAAKPKLDQALVVE 487

Query: 1503  HIEKMVESVFRNFDVDGDGHISQEEFQIIRGNFPYLSAFGDLDQNQDGCISREEMVSYFL 1682
             HIEKMVESVFRNFDVDGDGHISQEEFQIIRGNFPYLSAFGDLDQNQDGCISREEMVSYFL
Sbjct: 488   HIEKMVESVFRNFDVDGDGHISQEEFQIIRGNFPYLSAFGDLDQNQDGCISREEMVSYFL 547

Query: 1683  RSSSVLGGRMGFVHNFQESNSLRPVACRHCKALILGIYKQGLKCRACGVNCHKQCKDRLS 1862
             RSSSVLGGRMGFVHNFQESNSLRPVACRHCKALILGIYKQGLKCRACGVNCHKQCKDRLS
Sbjct: 548   RSSSVLGGRMGFVHNFQESNSLRPVACRHCKALILGIYKQGLKCRACGVNCHKQCKDRLS 607

Query: 1863  VECRRRAQSVSLEGSAPSPSPMHSHHHRAFSFSLPRPGRRGSRPPAIPLPAEIREEEVQT 2042
             VECRRRAQSVSLEGSAPSPSPMHSHHHRAFSFSLPRPGRRGSRPP      EIREEEVQT
Sbjct: 608   VECRRRAQSVSLEGSAPSPSPMHSHHHRAFSFSLPRPGRRGSRPP------EIREEEVQT 661

Query: 2043  VEDGVFDIHL 2072
             VEDGVFDIHL
Sbjct: 662   VEDGVFDIHL 671    (SEQ ID NO:5)
```

FIGURE 2

```
>CRA|18000005188697 /altid=gi|6755290 /def=ref|NP_035372.1| RAS,
         guanyl releasing protein 2; RAP 1A protein-specific
         guanine nucleotide exchange factor 1; CalDAG-GEFI [Mus
         musculus] /org=Mus musculus /taxon=10090 /dataset=nraa
         /length=608
         Length = 608
 Score = 1202 bits (3076), Expect = 0.0
 Identities = 589/615 (95%), Positives = 597/615 (96%)
 Frame = +3

Query: 228   MAGTLDLDKGCTVEELLRGCIEAFDDSGKVRDPQLVRIFLMMHPWYIPSSQLAAKLLHIY 407
             MA TLDLDKGCTVEELLRGCIEAFDDSGKVRDPQLVR+FLMMHPWYIPSSQLA+KLLH Y
Sbjct: 1     MASTLDLDKGCTVEELLRGCIEAFDDSGKVRDPQLVRMFLMMHPWYIPSSQLASKLLHFY 60

Query: 408   QQSRKDNSNSLQVKTCHLVRYWISAFPAEFDLNPELAEQIKELKALLDQEGNRRHSSLID 587
             QQSRKDNSNSLQVKTCHLVRYW+SAFPAEFDLNPELAE IKELKALLDQEGNRRHSSLID
Sbjct: 61    QQSRKDNSNSLQVKTCHLVRYWVSAFPAEFDLNPELAEPIKELKALLDQEGNRRHSSLID 120

Query: 588   IDSVPTYKWKRQVTQRNPVGQKKRKMSLLFDHLEPMELAEHLTYLEYRSFCKILFQDYHS 767
             I+SVPTYKWKRQVTQRNPV QKKRKMSLLFDHLEPMELAEHLTYLEYRSFCKILFQDYHS
Sbjct: 121   IESVPTYKWKRQVTQRNPVEQKKRKMSLLFDHLEPMELAEHLTYLEYRSFCKILFQDYHS 180

Query: 768   FVTHGCTVDNPVLERFISLFNSVSQWVQLMILSKPTAPQRALVITHFVHVAEKLLQLQNF 947
             FVTHGCTVDNPVLERFISLFNSVSQWVQLMILSKPTA QRALVITHFVHVAEKLLQLQNF
Sbjct: 181   FVTHGCTVDNPVLERFISLFNSVSQWVQLMILSKPTATQRALVITHFVHVAEKLLQLQNF 240

Query: 948   NTLMAVVGGLSHSSISRLKETHSHVSPETIKLWEGLTELVTATGNYGNYRRRLAACVGFR 1127
             NTLMAVVGGLSHSSISRLKETHSHVSP+TIKLWEGLTELVTATGNY NYRRRLAACVGFR
Sbjct: 241   NTLMAVVGGLSHSSISRLKETHSHVSPDTIKLWEGLTELVTATGNYSNYRRRLAACVGFR 300

Query: 1128  FPILGVHLKDLVALQLALPDWLDPARTRLNGAKMKQLFSILEELAMVTSLRPPVQANPDL 1307
             FPILGVHLKDLVALQLALPDWLDP RTRLNGAKM+QLFSILEELAMVTSLRPPVQANPDL
Sbjct: 301   FPILGVHLKDLVALQLALPDWLDPGRTRLNGAKMRQLFSILEELAMVTSLRPPVQANPDL 360

Query: 1308  LSLLTVSLDQYQTEDELYQLSLQREPRSKSSPTSPTSCTPPPRPPVLEEWTSAAKPKLDQ 1487
             LSLLTVSLDQYQTEDELYQLSLQREPRSKSSPTSPTSCTPPPRPPVLEEWTS AKPKLDQ
Sbjct: 361   LSLLTVSLDQYQTEDELYQLSLQREPRSKSSPTSPTSCTPPPRPPVLEEWTSVAKPKLDQ 420

Query: 1488  ALVVEHIEKMVESVFRNFDVDGDGHISQEEFQIIRGNFPYLSAFGDLDQNQDGCISREEM 1667
             ALV EHIEKMVESVFRNFDVDGDGHISQEEFQIIRGNFPYLSAFGDLDQNQDGCISREEM
Sbjct: 421   ALVAEHIEKMVESVFRNFDVDGDGHISQEEFQIIRGNFPYLSAFGDLDQNQDGCISREEM 480

Query: 1668  VSYFLRSSSVLGGRMGFVHNFQESNSLRPVACRHCKALILGIYKQGLKCRACGVNCHKQC 1847
             +SYFLRSSSVLGGRMGFVHNFQESNSLRPVACRHCKALILGIYKQGLKCRACGVNCHKQC
Sbjct: 481   ISYFLRSSSVLGGRMGFVHNFQESNSLRPVACRHCKALILGIYKQGLKCRACGVNCHKQC 540

Query: 1848  KDRLSVECRRRAQSVSLEGSAPSPSPMHSHHHRAFSFSLPRPGRRGSRPPAIPLPAEIRE 2027
             KDRLSVECRRRAQSVSLEGSAPSPSP H+ HHRAFSFSLPRPGRR SRPP      EIRE
Sbjct: 541   KDRLSVECRRRAQSVSLEGSAPSPSPTHT-HHRAFSFSLPRPGRRSSRPP------EIRE 593

Query: 2028  EEVQTVEDGVFDIHL 2072
             EEVQTVEDGVFDIHL
Sbjct: 594   EEVQTVEDGVFDIHL 608    (SEQ ID NO:6)
```

FIGURE 2

```
>CRA|18000005205935 /altid=gi|7662334 /def=ref|NP_056191.1| KIAA0846
            protein [Homo sapiens] /org=Homo sapiens /taxon=9606
            /dataset=nraa /length=689
          Length = 689
  Score =  618 bits (1576), Expect = e-175
  Identities = 314/597 (52%), Positives = 409/597 (67%), Gaps = 5/597 (0%)
  Frame = +3

Query: 234   GTLDLDKGCTVEELLRGCIEAFDDSGKVRDPQLVRIFLMMHPWYIPSSQLAAKLLHIYQQ 413
             G+  L K T++ELL CIE FDD+G++ +  L RI L+MH WY+ S++LA KLL  +Y+
Sbjct: 2     GSSGLGKAATLDELLCTCIEMFDDNGELDNSYLPRIVLLMHRWYLSSTELAEKLLCMYRN 61

Query: 414   SRKDNSNSLQVKTCHLVRYWISAFPAEFDLNPELAEQIKELKALLDQEGNRRHSSLIDID 593
             +  ++ N  ++K C+ +RYWI  FPAEF+L+  L  +E + +  Q G  +H SLIDI
Sbjct: 62    ATGESCNEFRLKICYFMRYWILKFPAEFNLDLGLIRMTEEFREVASQLGYEKHVSLIDIS 121

Query: 594   SVPTYKWKRQVTQRNPVGQKKRKMSLLFDHLEPMELAEHLTYLEYRSFCKILFQDYHSFV 773
             S+P+Y W R+VTQR V  KK K  LLFDHLEP+ELAEHLT+LE++SF +I F DY S+V
Sbjct: 122   SIPSYDWMRRVTQRKKVS-KKGKACLLFDHLEPIELAEHLTFLEHKSFRRISFTDYQSYV 180

Query: 774   THGCTVDNPVLERFISLFNSVSQWVQLMILSKPTAPQRALVITHFVHVAEKLLQLQNFNT 953
              HGC  +NP LER I+LFN +S+WVQLM+LSKPT  QRA VIT F++VA+KLLQL+NFNT
Sbjct: 181   IHGCLENNPTLERSIALFNGISKWVQLMVLSKPTPQQRAEVITKFINVAKKLLQLKNFNT 240

Query: 954   LMAVVGGLSHSSISRLKETHSHVSPETIKLWEGLTELVTATGNYGNYRRRLAACVGFRFP 1133
             LMAVVGGLSHSSISRLKETHSH+S E  K W  +TELV++ GNY NYR+  A C GF+ P
Sbjct: 241   LMAVVGGLSHSSISRLKETHSHLSSEVTKNWNEMTELVSSNGNYCNYRKAFADCDGFKIP 300

Query: 1134  ILGVHLKDLVALQLALPDWLDPARTRLNGAKMKQLFSILEELAMVTSLRPPVQANPDLLS 1313
             ILGVHLKDL+A+ +  PDW +    ++N KM QL    L EL  +      ++ N DL++
Sbjct: 301   ILGVHLKDLIAVHVIFPDWTE--ENKVNIVKMHQLSVTLSELVSLQNASHHLEPNMDLIN 358

Query: 1314  LLTVSLDQYQTEDELYQLSLQREPRSKSSPTSPTSCTPPPRPPVLEEWTSAAKPKLDQAL 1493
             LLT+SLD Y TED++Y+LSL  EPR+  SPTSPT+    P +P V  EW    PK D  +
Sbjct: 359   LLTLSLDLYHTEDDIYKLSLVLEPRNSKSPTSPTT---PNKPVVPLEWALGVMPKPDPTV 415

Query: 1494  VVEHIEKMVESVFRNFDVDGDGHISQEEFQIIRGNFPYLSAFGDLDQNQDGCISREEMVS 1673
             + +HI K+VESVFRN+D D DG+ISQE+F+ I  NFP+L +F LD++QDG IS++EM++
Sbjct: 416   INKHIRKLVESVFRNYDHDHDGYISQEDFESIAANFPFLDSFCVLDKDQDGLISKDEMMA 475

Query: 1674  YFLRSSSVLGGRM--GFVHNFQESNSLRPVACRHCKALILGIYKQGLKCRACGVNCHKQC 1847
             YFLR+ S L  +M  GF+HNFQE   L+P  C  HC    + GI KQG KC+ CG NCHKQC
Sbjct: 476   YFLRAKSQLHCKMGPGFIHNFQEMTYLKPTFCEHCAGFLWGIIKQGYKCKDCGANCHKQC 535

Query: 1848  KDRLSVECRRRAQSVSL---EGSAPSPSPMHSHHHRAFSFSLPRPGRRGSRPPAIPL 2009
             KD L + CRR A++ SL    GS P +  P      F F  G R    AI L
Sbjct: 536   KDLLVLACRRFARAPSLSSGHGSLPGSPSLPPAQDEVFEFPGVTAGHRDLDSRAITL 592    (SEQ
ID NO:7)

>CRA|18000005188699 /altid=gi|3928857 /def=gb|AAC79700.1| (AF081196)
            calcium and DAG-regulated guanine nucleotide exchange
            factor II [Rattus norvegicus] /org=Rattus norvegicus
            /taxon=10116 /dataset=nraa /length=795
          Length = 795
  Score =  533 bits (1358), Expect = e-150
  Identities = 267/590 (45%), Positives = 390/590 (65%), Gaps = 12/590 (2%)
  Frame = +3

Query: 156   GVRSEPGGRLPERSLGPAHPAPAAMAGTLD--------LDKGCTVEELLRGCIEAFDDS 308
             G R+ P GRL +S    PA  ++A              L KG ++++L+  CI++FD
Sbjct: 17    GSRAGPKGRLEAKSTNSPLPAQPSLAQITQFRMMVSLGHLAKGASLDDLIDSCIQSFDAD 76
```

FIGURE 2

```
Query:  309  GKV-RDPQLVRIFLMMHPWYIPSSQLAAKLLHIYQQSRKDNSNSLQVKTCHLVRYWISAF  485
             G + R QL+++ L MH    I S++L KL+++Y+ + + NS  + +K C+ VRYWI+ F
Sbjct:   77  GNLCRSNQLLQVMLTMHRIIISSAELLQKLMNLYKDALEKNSPGICLKICYFVRYWITEF  136

Query:  486  PAEFDLNPELAEQIKELKALLDQEGNRRHSSLIDIDSVPTYKWKRQVTQRNPVG-QKKRK  662
                F ++  L   ++E + L+      G  H  LID  + +  W R++TQR     KKRK
Sbjct:  137  WIMFKMDASLTSTMEEFQDLVKANGEESHCHLIDTTQINSRDWSRKLTQRIKSNTSKKRK  196

Query:  663  MSLLFDHLEPMELAEHLTYLEYRSFCKILFQDYHSFVTHGCTVDNPVLERFISLFNSVSQ  842
             +SLLFDHLEP EL+EHLTYLE++SF +I F DY +++ + C  +NP +ER I+L N +SQ
Sbjct:  197  VSLLFDHLEPEELSEHLTYLEFKSFRRISFSDYQNYLVNSCVKENPTMERSIALCNGISQ  256

Query:  843  WVQLMILSKPTAPQRALVITHFVHVAEKLLQLQNFNTLMAVVGGLSHSSISRLKETHSHV  1022
             WVQLM+LS+PT   RA V   F+HVA+KL QLQNFNTLMAV+GGL HSSISRLKET SHV
Sbjct:  257  WVQLMVLSRPTPQLRAEVFIKFIHVAQKLHQLQNFNTLMAVIGGLCHSSISRLKETSSHV  316

Query: 1023  SPETIKLWEGLTELVTATGNYGNYRRRLAACVGFRFPILGVHLKDLVALQLALPDWLDPA  1202
                E  K+   +TEL+++  NY NYRR    C F+ PILGVHLKDL++L  A+PD+L+
Sbjct:  317  PHEINKVLGEMTELLSSCRNYDNYRRAYGECTHFKIPILGVHLKDLISLYEAMPDYLEDG  376

Query: 1203  RTRLNGAKMKQLFSILEELAMVTSLRPPVQANPDLLSLLTVSLDQYQTEDELYQLSLQRE  1382
               ++N K+ L++ + EL +  + PP+ AN DL+ LLT+SLD Y TEDE+Y+LS  RE
Sbjct:  377  --KVNVQKLLALYNHINELVQLQDVAPPLDANKDLVHLLTLSLDLYYTEDEIYELSYARE  434

Query: 1383  PRSKSSPTSPTSCTPPPRPPVLEEWTSAAKPKLDQALVVEHIEKMVESVFRNFDVDGDGH  1562
             PR+  +P         P +PPV+ +W S   PK D   + +H+++MV SVF+N+D+D DG+
Sbjct:  435  PRNHRAPP-----LTPSKPPVVVDWASGVSPKPDPKTISKHVQRMVDSVFKNYDLDQDGY  489

Query: 1563  ISQEEFQIIRGNFPYLSAFGDLDQNQDGCISREEMVSYFLRSSSVLGG-RMGFVHNFQES  1739
             ISQEEF+ I  +FP+  +F +D++++G ISR+E+ +YF+R+SS+    +GF HNFQE+
Sbjct:  490  ISQEEFEKIAASFPF--SFCVMDKDREGLISRDEITAYFMRASSIYSKLGLGFPHNFQET  547

Query: 1740  NSLRPVACRHCKALILGIYKQGLKCRACGVNCHKQCKDRLSVECRRRAQS  1889
             L+P  C  +C  + G+ KQG +C+  CG+NCHKQCKD +  EC++R++S
Sbjct:  548  TYLKPTFCDNCAGFLWGVIKQGYRCKDCGMNCHKQCKDLVVFECKKRSKS  597  (SEQ ID NO:8)
```

Hmmer search results (Pfam):

| Model | Description | Score | E-value | N |
|---|---|---|---|---|
| PF00617 | RasGEF domain | 123.5 | 4e-33 | 1 |
| PF00130 | Phorbol esters/diacylglycerol binding domain | 59.5 | 3.6e-14 | 1 |
| PF00036 | EF hand | 21.8 | 0.00027 | 2 |
| PF01237 | Oxysterol-binding protein | 3.5 | 4.2 | 1 |

Parsed for domains:

| Model | Domain | seq-f | seq-t | hmm-f | hmm-t | | score | E-value |
|---|---|---|---|---|---|---|---|---|
| PF01237 | 1/1 | 249 | 272 | .. | 1 | 24 [. | 3.5 | 4.2 |
| PF00617 | 1/1 | 148 | 336 | .. | 1 | 227 [] | 123.5 | 4e-33 |
| PF00036 | 1/2 | 430 | 458 | .. | 1 | 29 [] | 17.4 | 0.0047 |
| PF00036 | 2/2 | 463 | 482 | .. | 5 | 24 .. | 6.7 | 4.9 |
| PF00130 | 1/1 | 499 | 548 | .. | 1 | 51 [] | 59.5 | 3.6e-14 |

FIGURE 2

```
   1 ACAGAAAGGT CCTGTTTCTA AGTCTTACAT TACCAAGACT GAGGTGCGGG
  51 GGCGGTCCTG GATCCCCCGC CCCAAGGCTG GGAGGGGCAC GCCTCGGAAG
 101 GGAGGTTTGG GGTCGGTGGT TTCACAGTGA GTGTGTCTGA AGCCAAATGG
 151 TCGGAAACCG TTACCCGCTC TCCTAGGCCC GGCTAGTGGG GACCCCAACC
 201 GCCTGCGGCT GCCCCTCCCA AGTTCCTCCC TGTTGGCCAG GCATCCAGGT
 251 CTCCAGTCTC CGAGCTGCGG AGAACCCACC GCCACATGCG GCTGCCCCTT
 301 TCCATTCGAC CCTGTGGGGA GCCAGGCTTC CGGGCCCCG TTCCTCCTGT
 351 GTGAACTGGG CCCCCCGCCC CCATTCCCAG ACATCAAGGC CGCGTCTCCA
 401 GATAGCCACG ATTTCATTCC TCGCTCCCCA CAGGTCCCTC TCCCCAAAAT
 451 ATTCCCATCT TGTCCTAGCC CATCCCCCAG ACTATCTCAA GGACCAGCTG
 501 TCCCCACGCC CCCGACCTCC ACTAGGCCTG TGCCACCCGC TGCCTGCAGG
 551 AAGACGCCCG GTCCCGGCC GGGTTAGCCC CATGGGAACG GTTTGTCTCG
 601 AAAACAGGAA CCCGAGCTGG GGGCTGGGCG GGCGCCCCT TCCCCACCGC
 651 AGTCCGCTTC CTGCCCCTCC CGGCTTCCTC CGCCCGACAC CCAGGCAGGG
 701 CGGGGGGCAC TGGGGCGTCC GCGGTTGGGG GAGGGGCTCT TCGTTTCGGT
 751 CCCCCCTCCC GCGTCCCGGG CGGCGGGGCC TCCGGTCGCC CGCCTCGGGG
 801 CAGCTAGTGG CGCAGCCCCC CGCCCGCGGC CCTGGCCTCC CGGGCGGCGC
 851 GGCAGGGGAG GGGTTAAGCT GCCGCAGGGA CCGCCGCGTG CGGGGCGAGA
 901 GGGAGCCCCC GGTGGGGGTG GCGCAGCCGG CGGTGCGGAG CTCCGCGCAG
 951 GGGCGGAGGG GGGAGGGGGC AGCCTGGCGC GGGGGCGGGG GCGGGGCGGC
1001 GGGGAGCGGG GCCGCGGCGT GGAGAGCGGG CGGGAGCCGC AGCCGCAGCG
1051 AGGCCGGCGG GCGGGAGCGC ACGGAGGTGG GGTCGGCCAG GCCGGTGCGG
1101 GCTCCTTGCG GCAGGTCCCA AGAGTGAGTG GGCGAGCGCG GGCGGGGCGC
1151 CAGGCGAAGG AGGGCGCGGC CCCCAGCGAC TCCCCCCCCG CCCAGGGCGG
1201 CGCGGGCGGG CTGGGGGCGG CGAGCGGGTG GGGAGTCTGC GGCCCGGGTC
1251 TGGGAGAGGG GGCAGCGGCC ACGAGAGCTA AGGCGCGCTG GATCCCCGGA
1301 GGGCGGAGGA CCTCCACGGT GCACCCAGCT TTTCCCAGCC ACCTTCCAGC
1351 GGGGCCCTCC CCCGCGTACC CCCATTTGGC AGATGAGAAA ATTGAGGCTC
1401 CCAGAGGCCA AGTGATTCTC AAGGTCACAC GAGGAAGCGG TAGAGCCAGG
1451 CGGGGACGGC TCTGGGTGGC TCTTAGGAAA AGTCCGCCTG AGAACTCCGT
1501 ACAGGAGCTC CCCTGTCCTC CAGCCTGGGG GAGTGAGTAT GTGTAGGGCC
1551 GGGGTACCTT TCCGTGGGGC AAGGCTCTGC CAAAATCTGG GAGTGAGGGG
1601 AGTCAGGGAG CTGGGGCCGC AGGGCGGGCC CTGCACCGCA AATGGGAGGG
1651 GGGCGACGGA ATGGGCGTGC GCACCCATGG GGGTGTGTGC ATGTGTGTGG
1701 GAGTGTACAT GCGTGGAGAG GCACTGCCTT GCGTGTGTGC ACACGTGTGA
1751 GGATGTCAGC GCCTGTGTGG CCGCGGGACT CAAGGCTGGC CTGGCTCAAG
1801 TGAACAGCAC GTCCAGGAGG CGACCTCGTC CGCGGGTTTG CATTCTGGGG
1851 TGGACGAGCT GGGTATGTGT GCCTGAGGGT TTCTTCGTGC AGGTGTGCAC
1901 AGGGTGTGGG TGCCATTGTG TGTGAGAGAC GGAGGATGGG GAGGCCGGTG
1951 CCTGTGGCCC GGTGCGTGTA AGTGCGGACG CCTGCACCTC CACTTAGGTC
2001 CCCGGCCTCC GACGACTAAC TTGGGTGTGG AGTGTTTGCC CCTGCCAGGG
2051 TGCGTATGAC CCCGCCAGTG ACCGGAGTTG CTAATGGTGT CATGCACCCA
2101 CCGGCCACCC TTGGCGCGAG CGCCCCCCTC TGGACACCCT GCTCCGTGCG
2151 CGCTCACAGT TCGCCTGTGC GGGGCCGGGG CCAGGGTCAG GAGCCGGGGA
2201 TAGGGAGGAA GAGGGCCTGT GGACAAGCTG AGCCGGGACC CCTGGGACCT
2251 TTGCGGAGGT GGCCTGGGAG CGCTCAGTTC CCAGGCTGAG GCTTCCCGCT
2301 GACGCCTCCT GGCCGCAGCG GGCTCCCCCC GCCCCAGGAA TGTTCCTCTC
2351 CCATCCAGTC CGCCTCCCCT AGGGCAGGCC CCTGGGGGC TGCCGCAGCC
2401 CCGCCTCGCC TTCCTGGGCT CCCGGGAGGG GGCGAGGCGA GCAGGACGCC
2451 TGGGTTCTCT CCCCCCACCT CCCATACCAG GGAGAAATTC CTCCGAGGTC
2501 CCCTCAGGCT CTGGGTTCCC AAAATAACCC TGCGGGGAA GGGAGGCTGT
2551 GGAGGGAGGG AAGCGGGAGG GGCGCAGAGC CGAGCTGCGG GGTGCTGCAG
2601 GTGCCTCTGG GGAGAGGGCG CGAGGAGAAG GCGCCCTGCG GGGGGCTGGG
2651 CGCCAGCCAG TCCTGGGATC TTGGTTCGTC CCCATCCTCG TGAAGCCCCT
2701 CGGCCTTCCC GCGACTCCGA GGGTGGGCCG GAAGCCTCTC TGCGGGTCCG
2751 TTTCCCAACT GGCGGGTTGC ACCATCCCGG GCCAGACCGT TTAACCCCGG
2801 GAGTGGCCGC GGGGGACAAC TCCGCCCCTG TCCAGCAGGG GGCGTGCCCG
2851 CCCCGCCCCG TTTCTGCCCG CGGGGCCGCT CCCCCGCCCG CGACTCCGCA
2901 GACTCCCGCT CTGCCTCTCC CGGGACAGGG GTTCGGTCCG AGCCCGGTGG
2951 GAGGCTCCCG GAGCGCAGCC TGGGCCCAGC CCACCCCGCG CCGGCGGCCA
3001 TGGCAGGCAC CCTGGACCTG GACAAGGGCT GCACGGTGGA GGAGCTGCTC
3051 CGCGGGTGCA TCGAAGCCTT CGGTGAGTGG CTCGGGAGGG CACACGGAGC
3101 CTGAGCCTAG CCCCGAGTCT GAGCCCGGGT CCCTGCCTCC CAGGCACAGT
```

FIGURE 3

```
3151 CCAGGGCACA GCCCTGACCC GGACCCACCC TGCTCCGCAG CGTGCAGTCT
3201 CTTTAACGAA AGCCTCCTCC GCAACGCAGG GCAGAGAGAT GCACGCCCTT
3251 CAGACAGATG AGGTTTCCCT TCTCTAGCCT TCCCCAGCGG CGGCGAAGGG
3301 AGGGCCGGGT CCCGGACTCT GACACTTGAG GGGCATTATC TGTCTCCCGG
3351 GGAATCCGGA GGAACTCGCT ATCTCCGGCC TGGGAGCTGT TTCCGGCTAA
3401 TGGGGGGCGG CTTATCTGGT GAAGGGGTGC CCCTTCCCCC CAAGCGCTCA
3451 GGAAATGACC TCTGGATTCT TGACCCCGGG GAACCCAGGC TCCTTCCGCC
3501 CCAGCTGGTT CCCCTCCGGA CGATGGGCGG CTCGGGCGCT CCCCTCCTCC
3551 AGTCCTCAGG GCGTGCCTAT CTCTCGCCCA CCACACCTTT CCTCTCTAAT
3601 TTGCCTCCTG CTCTCGGAGT CCTGGGCAAG CAGGAGGTGG GCGGGGTCGA
3651 GCGTGCACCC GAAGGACCGA TACCTGGCGG GTTGCGGGGT GAGGATGAGG
3701 CATGGTAGCT GCGGACCCAG CTCAGCCACC TGTCTTTGAC CCTTCGGAGT
3751 CAGATGACTC CGGGAAGGTG CGGGACCCGC AGCTGGTGCG CATGTTCCTC
3801 ATGATGCACC CCTGGTACAT CCCCTCCTCT CAGCTGGCGG CCAAGCTGCT
3851 CCACATATAT CCTTCGCCGG CCTTGCCAAG GCCCCCGCCG TCGGAGCCCA
3901 TGCGCAGCCC CTCTGCCCAG CCCAGGTGCA GAATGAGCCT CGCTCCTAAG
3951 TATAGGCCAC TCCTTATCCC AGAGCTCAGG CGTCGTCCCA GCCTCCAACT
4001 AGGGCCTAGG CTCTGCCCCC TCCTTGCTCC TAGCGACTCG GTCCTGTCCC
4051 CAGGCTCTGT CCCCAGCCGA GGCCTTGCCC TCCTTCTCCC TAGAGTCTAG
4101 GGCCTGCCCC TGCTTCAGGC TTGGGTGCGC CCCGTGCATC TCTCTCTCCC
4151 AGAGCCCAGG CTTTGCTTTC AGCCTCCCTC AGCACCTAGT CCTCCACCCC
4201 CACCTCCAAC CCCTCCCAGA GCTCAAGCCT CACCCCCAGC ATCTCCGCAG
4251 AGCGCAAGCC CCATCCCTAG AACGTGTCTC CTAGAACCAG GCCCCGCCCC
4301 CAGCCTCCCT CCACGCAGGC CTCCCTTTCT AGAGTTAAGC GGCCTCCTTA
4351 ACCCTCTCCT TCACCTACCA ACAATCCCGG AAGGACAACT CCAATTCCCT
4401 GCAGGTGAAA ACGTGCCACC TGGTCAGGTG AGTCTTTCCC CTGGGGCTCT
4451 AGCCCCTCCC CTTTCTCCCT TCTCTCTGGC TTCAGGCTGG CCTGGAGGAG
4501 GGGGCAGGGC GCTGTTTCTG GGAGTGGGTT TGAACCCTGG CTTGTCCGGG
4551 TGGGCAGTGC TGCCACAGGC TCACCCCTTC CTGGGTCTGG GCCTTAATTT
4601 TCTTTTCTGC GCAGTGCGGG TGGTTGTCTC AAGGGTCTAA TGTACACTTG
4651 GAGTGGCGAA GGAAAGAGCT GGAACCATAG TTTGAGGGTC TTTTTGCTTA
4701 GGTGACTATA ATCTCAAATA GCTCCTTGCA GCCTGCTGGG TGATGGTGGG
4751 GGAAGGGCTA TCTTGGGTGA CTCCCCGCTC CTCCAGGTAC TGGATCTCCG
4801 CCTTCCCAGC GGAGTTTGAC TTGAACCCGG AGTTGGCTGA GCAGATCAAG
4851 GAGCTGAAGG CTCTGCTAGA CCAAGAAGGG AACCGACGGC ACAGCAGCCT
4901 AATCGACATA GACAGCGTGT GCGTGGGGGG AGCACAGAGG GCTGGGGGGG
4951 CACTCAGTAT CCTATACCAT CTGTGCTTAA TAAATGTCTG TTGAACTGAA
5001 TGAGTGAGGG TCATGTTGCT CTCTCGCTTA AAAACCTTCC ATGGCTCCCT
5051 ATTGCCTTCA ACATGCCTCC TCTGGGCAGC TTGGCGTTCC TGCCTCATCT
5101 TCCACTGCCA CCACCCATCC CACACACCTC CTCCTGTAGC TGCGCTGGGT
5151 CGGCTCCCCG TCGGCTGAGC TCTCGAGTCC TTTCTCATCA TGGTGCTCTG
5201 CTCATATCAT CCCCCTTGCT GCCTCCTCCG TGTTACCAAG ACTCAGTTCA
5251 GGCATGAAGT CTCCGTGGGC TCTGAGGGTT CGGGGCTCTT CCGGGGTAGA
5301 ATTTGTCGTT CCCACCTCTG TTTTCCATGG CACTTTGTAC AGACTCCTGT
5351 ACAAAGACCT CTGTACATGT GTCACGCTGT TTTGTGATCA TGTGTTTCTG
5401 TGTCTGTCTC CCTCAGTAGA CTGTGAGCTC CTCGAGGGCA GGAACCGTGT
5451 CTTACTCATC TCTGTATTCC CAGCGCCTAG CACAGTGCCT GGCACAGAGT
5501 ACGTTGTTCA TAAATGTGTG TTGAGTGCAT GACGGGGTGG GGGGAGATGA
5551 GGAGGAGTTG CTGGGACTGG GAACATTCGT GCCTAGGACA GTGCCTCGCA
5601 TTATGTAGGT TCTCAGTAAG CGTGAATGGT GTGTCTGTGT GAGTGGGGGG
5651 CCACGAGGCA TGCGCATGTC CAGCAAAGGG CTCACTACCC CTGCCCCCCC
5701 AGCCCTACCT ACAAGTGGAA GCGGCAGGTG ACTCAGCGGA ACCCTGTGGG
5751 ACAGAAAAAG CGCAAGATGT CCCTGTTGTT TGACCACCTG GAGCCCATGG
5801 AGCTGGCGGA GCATCTCACC TACTTGGAGT ATCGCTCCTT CTGCAAGATC
5851 CTGGTGCGGC CCGAGGGCTG GGGGGTCAGG GGTCCAATGT GGGCTGGAAG
5901 AGAGTTCTAG GAGGGGCAGG GTCCCTGGCG TAGGCTGGGT CACAGGGTGC
5951 ATCAGGGGTT TCAGTGTAAC CACTGAAGGT CAGCTGGAGG GTGAGGAGTG
6001 GCTATCAGTG AGGGGAGAGG CCGGCAAGGT GCTGAGGCCA CTCCTCATGC
6051 CCCCAGTTTC AGGACTATCA CAGTTTCGTG ACTCATGGCT GCACTGTGGA
6101 CAACCCCGTC CTGGAGCGGT TCATCTCCCT CTTCAACAGC GTCTCACAGT
6151 GGGTGCAGCT CATGATCCTC AGCAAACCCA CAGCCCCGCA GCGGGCCCTG
6201 GTCATCACAC ACTTTGTCCA CGTGGCGGAG GTGCCTGCCC CTCCCTCCCG
6251 GTGTCTCCCA ACCACCCCAC ATGCCAGTCA GGCCAACCCT TCCCTTCCCC
```

FIGURE 3

```
6301 TAACCCACTG CCTTCTCTCT AGATAAGCTG GGCCAAATTC TGGGCCCACT
6351 CAGTGACTCC CTGCCTCTCC GTCCCCATTT GCCTTCCAGA AGCTGCTACA
6401 GCTGCAGAAC TTCAACACGC TGATGGCAGT GGTCGGGGGC CTGAGCCACA
6451 GCTCCATCTC CCGCCTCAAG GAGACCCACA GCCACGTTAG CCCTGAGACC
6501 ATCAAGGTGC CTGGGACTGG GGAGGGGCCG GTGCTTCCCA GGTCTGTCTT
6551 CACTGGGTCC TCCCAGCAGC ACTGGGGGCT GGGCACAGCT GTCCTCATTT
6601 GATAGATATG GAAATGGAGG CTCAGAGGGG TTAAGTGCTT TTCTCAGTTT
6651 GCACAATGGC AACAGCAGAG TGGGGGCTCA CAGGTCGTCA GGGACCCCAA
6701 AGCTAGTACT TTTTTTTTTT TTTTTAAGAC AGGGTCTCTC TCTCTGTTGT
6751 CCAGACTGGA GTTCAGTGGT GCAGTCACAA GCTCACTGCA GCCTTGAATT
6801 CCTGAGCTCA ATCGATCCTC CCACCTCAGC CTCCTGAGTA GCTGGGACTA
6851 CAGGTGTACG CCACCATGCC TAATTTTTGT ATTGTTATTA ATTTTTTTTT
6901 TTTTTTTTTA GAGATGGGGT TTTGCCATGT TGCCCAGACT GGTCTTGAAC
6951 TCCTGGGCTC AAGTGATCCG CCTGCCTTGG CCTCCCAAAG TGCTGAGATT
7001 ATGGCTTGAG CCATTGTGCC TTGCCACTTG TAGTTCTTC TTTTCTTTCT
7051 CCTTCATTTT TTATTATTTT TGAAGTATTT TGAAGTATTG AGTAACATAC
7101 ATATAGAAAA GTATATAAAA ACATATGAGA CTGGGCGTAG TAGCTCACAC
7151 CTGTAATCCC AGCACTTTGG GAGGCTGAGG TGGGCAGATC ACGTGACATC
7201 AGGAGTTTGA GACCAGCCTG GCCAACAAGG TGGAAACCCA TCTCTACTAA
7251 AATACAAAAA TTAGCCAGGC ATGGTGGCAC GCACCTGGAA TCCAAGCTAC
7301 TTGGGAGGCT GAGGCAGGAG GAGAATTACT TGAACTCAGG AGGCGGAGGT
7351 TGCAGTGAGC CAAGATTGTG CCACTTCACT CCAGCCTGGG CGACAGAGTG
7401 AGACTCCATC TAAAAAAAAA GAAAAGTATA TAAAAACATA TGAATAGTTT
7451 AAAGAAAAAT TGTAAAGAAA ACACTGTGTA ACTACTGCCC GGGTTGGGAA
7501 ATAGAACCTT GCCAGGCCCC CAAGCGCCCA GCACTTTAGA GCATAACTCC
7551 CTCCCCACGA CTTTTGCAAT GATGATCTTG CTTTTCTTTA TAGCTTCACC
7601 ATGTAGGTAT GCGGTCCAAA ACAATGTGGG GCTTTTTGTT GTCTGTTTTG
7651 AACTTTCTAT GAATGGAATG TTGTTTGTGT TATTTTATGT CTTGCTTTTT
7701 TCATTCCACA TGGTTCTGAG AGTCTTTTCA TTCTGTCATG TGGAGCAATT
7751 GTTTTTTCAT TTTCATTGCC ATATAATATT TTATTGTACG TCTACCCCAA
7801 TTCATTTATT TATTTATTTT TTTGAGATGG AGTCTGTCTC TGTCATCCAG
7851 GCTGGAGTGC GGTGGCGAGA TCTCATCACT GCAACTTCCG TCTCCTGGGT
7901 TTACGTGATT CTCGTGCCTC AGCCTCCTGA GTAGCTGGGA TTATGGGCTC
7951 GTACCACCAC GTCTGGCTAA TTTTTTGTAG AGACAGGCTT TCACCATGTT
8001 GCCGAGGCTG GTCTTGAACT CCTGAGCTCA GGCAATCCAC CCGCTTTAGC
8051 CTCCCAAAGT GCTGGGATTA CAGGTGTGAG CCACTGCCCC CAGCCTACCC
8101 CAATTTATGT ATTGATTCTA TTGTTGAATG TTGGGGTTTT TCCTTTTCTT
8151 TTCTTTCTTT CTTTTTCTTT CTTTTTTTCT TTTTTTGGA GAGGGAGTCT
8201 TGCTCTGTCG CCAGGCTGGA GTGCAGTGAC GCTAATTTGG CTCACTGCAT
8251 CACTGCACCC TCTGCCTCCC GGGTTCAAGC GATTCTCCTG CCTCAGCCTC
8301 CTGAGTAGCT GGGACTACAG GCATGCACCA CCACACCCGG CTAATTTTTG
8351 TATTTTTTTA GTAGAGATGA GGTTTCCACC ATGTTGGCCA AGATGGTCTC
8401 CATCTCTTGA CCTCATGATC CATCTGCCAT GGCCTCCCAA AGTGCTGAGA
8451 TTACAAGTGT GAGCCACCAC GCCCAGCTGG TTTTTCCAGT TTTTGCTGTT
8501 TGGACGGGGT GGCTGAGTAT GTTCTTCCAG GTCATTGTCC TGTGCTGCCT
8551 TGCCTCCCTG AGCCTCTGTT TCTCCTGTTA AATGTTGATG ATTCCCTGCA
8601 TCCAGGCCTG GTTTAGAGGT GTGGTGCTTT TGGCAGTGAG TATTGCCTTG
8651 AATTCATGGC AATGAATTCA ATCCCCAGGG GCTGAGAGAG CCAGTCGTGG
8701 GGGACAGTAA GGGAGGTTTT TACTCTTTCA CCTGTCCCTG ACCCTGACTC
8751 CTCCTCACCC CCTCCTACAT TTCCAGGGCT GAGGTAGGGA GGATAGTTGT
8801 GGGGGTATGA CTCCTCTGTC CTTTGTCCCC AGCTCTGGGA GGGTCTCACG
8851 GAACTAGTGA CGGCGACAGG CAACTATGGC AACTACCGGC GTCGGCTGGC
8901 AGCCTGTGTG GGCTTCCGCT TCCCGATCCT GGGTGTGCAC CTCAAGGACC
8951 TGGTGGCCCT GCAGCTGGCA CTGCCTGACT GGCTGGACCC AGCCCGGACC
9001 CGGCTCAACG GGGCCAAGAT GAAGCAGCTC TTTAGCATCC TGGAGGAGCT
9051 GGCCATGGTG ACCAGCCTGC GGCACCAGT ACAGGCCAAC CCCGACCTGC
9101 TGAGCCTGCT CACGGTGAGG AGCAGGGGGC AGGGAGGTGG GGAGCTGGGC
9151 ACCAGGGGTT GACAGTTTCC CCAGGTCCTG GCTGTGGGCG TGGCCTGGGG
9201 CTCTGGGTTC TGGCCAAGAA ACTGAGATCT AGCGTGGGCT CTGGGGTTTG
9251 GAGTGGATGC TGAGAAGGGG TCCAGGCTCT GGTTGGGGCT GTGGACTGAG
9301 GTCTGATCTC CAGGCTGGTA TGTGGACTGT GGGCAGTTTG AACTGGGCCT
9351 GGGTCCCGGG TTGAGTTCTG GCAATGGGCT GTGTTCTAGG GCTGGGCCAA
9401 GCTCTGCATT CTGTGGGCAG GGTGGTTTC TAAGCATGGC CCTGGGCTCG
```

FIGURE 3

```
 9451 GAGTGAAGTT CTGGGCTTGG CTTTACACTT GGTCTTGGGG TCTAGGGTGG
 9501 GAGTTGGGTT CTGGTTTAGA TCCAGACAAG GTTCTAGACA TTGGGCTGGG
 9551 GCTTAAGTGT TAAGGTTTGG AGTGGATTCT TAGCTGCTTC TGGGCTCTGG
 9601 AGGGGATCAG GGTTGAAATC AGAGCTTCTG GCTGGGTTCC GACCTGGCTT
 9651 CTTCCCTGAC ATCTTGGCAA TATGTTGTGT TCAAGGTTTG GGCCATGCT
 9701 GTGGTTTGAT CTGTGCGCTG GGATGACATG GGGGTTGCTG TGCTGTGTTC
 9751 TAAGCCAGGC TTTGTCCTGA GTCTAGCTTC TGACCCGAGC TCTGGCTGAG
 9801 CTGTGGCCTC TAGGTCGACC TTTGGCCCTG GGCTCTGTGG CCGTGGGCAG
 9851 GGGCCAGTGG GGGTGATCAG ATCTGTGTGT CCCAGGTGTC TCTGGATCAG
 9901 TATCAGACGG AGGATGAGCT GTACCAGCTG TCCCTGCAGC GGGAGCCGCG
 9951 CTCCAAGTCC TCGGTGAGGG GGTACTCCCT CCTCTCCACT CTGCCCTTCC
10001 CTCCTGAGAA TCCCAGGATG TGAGGATGGG AAGAGCTCTT AGCAGCCACC
10051 TCACCCATCC ATCTTGTAGG ACAGAGGCAT CCTGGGGGTA GGGCAGTAGT
10101 GTTGGGCAGA CTTCCCTCTC CCAGGGATTC CCCTCTCTGT TCCCCGGGGC
10151 TCTGGGCTCC CCCTGCCTCT GGCCCTAGCT CAGGCCCGAC CATTTCCATA
10201 GCCAACCAGC CCCACGAGTT GCACCCCACC ACCCCGGCCC CCGGTACTGG
10251 AGGAGTGGAC CTCGGCTGCC AAACCCAAGC TGGATCAGGC CCTCGTGGTG
10301 GAGCACATCG AGAAGATGGT GGAGGTGAGC TCCTGCGGAG CCTGAGCAGT
10351 GTGTGGGGAG AGGCCAGTTT GCCGGAGCAC TGCCCTGGAA GCCAGCACGA
10401 GTGTCCTGTT CAAGACCCAG CACTCAGCCC CTAGGAGTCA CAGGGCCTGG
10451 CAGGCCAGCT GCACGGGGCT GAAGTGCCCC TGGGTAGGGT GGGGGTGGAG
10501 GTATGGAACG GGGGTGGTGT CAGAGACCTC TCTGAGACAC ACCTCATCAA
10551 ATGGACTGGG AACGTGGGAA GGGACAGGAC CTGATGTCCC CTTTACTCTC
10601 CCCTCTTCTG GCTCTGCGTG TCCCTCTGCG TGCCCCAGTC TGTGTTCCGG
10651 AACTTTGACG TCGATGGGA TGGCCACATC TCACAGGAAG AATTCCAGAT
10701 CATCCGTGGG AACTTCCCTT ACCTCAGCGC CTTTGGGGAC CTCGACCAGA
10751 ACCAGTGAGG AGGGCTGGGG ACCTGGGGGA GAGGGAAGGC AACTCAGCCC
10801 ACTTCTGCCT GGGCTTCAGT TTCTTGTGTG CAAGATGAGG TCACTGAGCC
10851 AGATGATCTT GGCCTGGGAA GCTGCCAGTG TGGGAAAGGG CACTTGCTTT
10901 TGTGGGGAGG AGAGGCTGCC AGCTGTGGAG GCGCAGTGGT ATCTCACAAA
10951 TTCAGACAGA TGGGGGGCTC CACCTGAGTC TTGCAAAGAC TGTGACCTGG
11001 GGACTGTGGC TACAAAAGTG CTGTTTTATT TGTGGAGCTC ACAGCTGTCA
11051 AGAAGTGTGG GCAACTTGAG CTCCTGGATA GTCTGTTCTA ATGAATAGAT
11101 AAGAAAGGTT TGTAATTAGC AGTACCCAGT TGTTTATCAA CAGTTCATAT
11151 GCTGACAATT TGGAAAAACA GCTGGTTCTC TGAAGTAGGT TAAACATGCC
11201 CCCTGAAGCC AGATTCATGC CCTATTTTTG CTGAGCAGAA AAAACTCCAT
11251 TCAAATTTA AAGTCCATCT CAGGTCGATT TATTTTTTAA TGTTACCTGT
11301 ATTTCAAAAA TCTGTTGTTT TTTATTTCCA CATTACAAAA ATCCACGGTA
11351 AAATAAAATC TAGGTGGTAA AATAAATTTA TAGTGAACAA AATGTTTAAA
11401 GTAAGAAGTG AGAGGCCAGG TGCGGTGCCT CACGCCTGTA ATCCTAGCAC
11451 TTTGGGAGAC TGAGTTGGCA GGATCAATTC AGGCCAGGAG TTTGAGCCCA
11501 GCCTGGGCAA CAGATAAGA CCCTGTCTCT ACAAAAATTA TTATTATTAT
11551 TTTTGAGACA GAGTCTCACT CTGTTGCCCA GGCTGGAGTG CAGTGGTACA
11601 ATCTCGGCTC GCTGCAACCT CCACTTCCTG GGTTCAAGTG ATTCTCCTGC
11651 TTCAGCTTCC TGAGTAGCTG GGATTACAGG CATGCATCAC CGTGCCTGGC
11701 TAATTTTTGT ATTTTTAGCA GAGATGGGGT TTTACCATGT TGGCCAGGCT
11751 GGTCTCAAAC TCTTGACCTC AAGTGATCTA CCTGCCTTGG CCCCCCAAAG
11801 TGCTAGGATT ACAGGCATGA GCTACTGCTC CTAGCCTAAA AAAATTTTTT
11851 TTGGGCATGG GTGGCACGTG CCTGTAGTCC CAGCTACTCA GGAGGCTGAG
11901 GCAGGAGGAA CCCTTGAGCC CAGGAGGTTG AGACTGCAGT GAGCTGTCAT
11951 CACACCACTG CACTTCAGCC TGGGTGACTG CGCGAGATCA CCCCCATCAA
12001 AAAAAAAAAA AAAGAAAAA AAAGGAAGA AATGAAAGTC CCCTCTTTCC
12051 TTTTCCACTG GTAGAAGTTG CCATGATTAA GCACTGTTAA CAATATTAAG
12101 CTTGGCAGTA TGTGGATTCT TCCAGTCTTC TTTTCCCAGG CAGGTGCACA
12151 TTGATAGAGA TTTTGTTTGT TTGGTGTCTG TTTCATGGAC AAACAGGATT
12201 AGAGCATAAA TCTAGTTCTG CTTGTGGCTT TTATCATAGC TGCTTTATTT
12251 CTTCTCCCAG ATTTTAGGCA GAGGTAGTTG AGTTCCATGT TTTCTCCCTG
12301 GGTTGGTGGG TGGATTTTTA TCTAGACCAC CTTTTCAGTG AGAATGACCC
12351 TTTGAGACGA TGGAGGCCTC AGCTTCATGC AGCGGGCTCA GCCTTAACCC
12401 TCCACCTCCT GCAGGCCCCA AGCTGTGTGT GTGTGTGTGT GTGTGTGTGT
12451 GTGTGTGTGT GTGTGTGTGT GTTGGTAAGG GGAAAGCCCC TGGTTGGGTA
12501 TCAAAACCT AGCACCTGGT TCGGCAGGAG GGAGACCAGC ACCGGCTCCC
12551 CAGGACCAGG CCCAGCTCAC CACTTCATTG TAAAGCTCCC TCTTTGTTTC
```

FIGURE 3

```
12601 TGGAACTTGG GTGTTTCCAT TTCTTTCTTA CAAAATTATC TATGCATTTA
12651 CAGCAATTGT TGATATATCT TTAGGCAGCA TCTAGGTACT TGTAGTGGGT
12701 TCTCTTTTTT CTTTTTTCTT TTTTTAATC ACCCTCTCTT TTTTTTGAGA
12751 CAGAGTCTCA CTCTGTCGCT CAGGCTGGAG TGCAATAGCG CGATCTTGGC
12801 TCACTGCAAC CTCTGCCTCC CAGGTTCAAG TAATTCTCAT GCCTCAGCCT
12851 CCCAAGTAGC TGAGATTACA GGCACTGGCC ACCAGACCCG GCTAATTTTT
12901 TTTTCTTTTT CTTTTTTTTG AGACGGAGTT TCGCTCTTTG TTGCCCAGGC
12951 TGGAGTACAG TGGTGTGATC TCGGCTCACT GCAACCTCCG CCTCCCGGGT
13001 TCAAGTGATT CTCCTGTCTC AGCCTCCCGA GTAGCTGGGA TTACAGGCGC
13051 GCGCCACCAT GCCTGGCTAA TTTTGTATTT TTTTTTTTT GAGACAGAGT
13101 CTCACTCTGT CACCCAGACT GGAGTGCGGT GGCGCGATCT CGGCTCACTG
13151 CAAGCTCTGC TTCCCGGGTT CATGCCATTC TCCTGCCTCA GCCTCCGGAG
13201 TAGCTGGGAC TACAAGCACC CACCACCGTG CCCGGCTAAT TTTTTGTATT
13251 TTTAGTAGAG ACGGGGTTTC ACCGTGGTCT CGACCTCCAG ACCTCGTGAT
13301 CCACTAGCCT CAGCCTCCCA AAGTGCTGGG ATTACAGGCG TGAGCCACCT
13351 CACCCAGCCT AATTTTGTAT TTTTAGTAGA GATGGGGTTT CACCATGTTG
13401 CGCAGGCTGG TATTGAACTT CTGACCTCAG GTGATCCGCC CGCCTCGGCC
13451 TCCCGAAGTT CTGGGATTAT AGGCGTGAGC CACCGCACCT GGCCTAATTT
13501 TTGTATTTTT AGTAGAGATG GAGTTTTACC TTGTTGGCCA GGCTGGTCTT
13551 GAACTCCTGA CCTCACCTCA GGTGATCTGC CCACCTCGGC CTCCCAAAGT
13601 GCTGGGATTA CAGGCATGAG CCACTGTGCA CCCGGCCTAA AAATCACCAT
13651 CTTGACAGAA CTTCACGCCT TGCTTTTTGT TTTTTTTCAT CTTTGTGCTT
13701 GTTTTCCACT TAACCCTTGA TCACAGACAT CTTTCCATGT GGATTCATGT
13751 AGAACTACCT CATTCGTTAG AACAGCTGCA GAGTATTCCA CTGTGCGGTT
13801 AGTCCATCAT TTCCCTAACC ATCCTCCTGC TGATGGACAG TTAGACTGTT
13851 CCAGTTTTTC AGTATGATTC TATGCCAGGC TGCCATGAAC GTCCTTTTAC
13901 TGATCCACTC AGGCCAGTAT TTCTGTAGGA GAAATTCCTA GAAGTGGGAT
13951 AATTGGATCA AAAGATATGC ACATTCTAAA TTAGGAGAGA GACTGCCAAA
14001 CTGACCTCAG ACAAGGTTGT ACCAGTTTGC ACCCCCATCA GCAGCGTACA
14051 AGTGCCTGCT TCCCAACTTC CTCGCCAACA GGGATGCTAT AAAAAGCTTC
14101 ACAATTTTGC CAGTCTCATT GGCAAATGGT ATCTTGGTTA AATTTGCATT
14151 TCTTTAATAC TAAGTGGGGG TAGGGTATCT TTTCATATGT TTATTGGCCA
14201 TTTATTTCTT CTGTCAATTG CCTGTTCTGA TTCCTTGTCC ATTATTCTAC
14251 TGGGTTTGTT GGTCTTTTTC TCATTGATTT TTAGAATCTC TGTTAATGGA
14301 TATTAACCCT TTGCTGTTGA ATGTGTTTGC AAATATTTTC TCCCTGTCTG
14351 TCATTTATGT GTCTTTTTCC ATATAAATTT AAAAAATTTT GGTGGGCTCA
14401 ATAGGTCAGT CTTTCCCTTC CGGGCTTCTG GGATTTGTGT TCGGGGTAGA
14451 AAGGCCCTCA GCCCCTCAAG ATTATAAAAT TATAAAACCT TTTCTTTTTT
14501 TTTTTTTTTT CTGAGACAGG GTGTCTTGCC ATGTCACCCA GGCTGGAGTG
14551 CAGTGGCATG ATCTTGGCTC GCTGCAACCT CCACCTCCCA GGTTCAAGTG
14601 ATTCTCGTGC CTTAGCCTCC CGAGTAGCTG GGATTATAGG TGCCTGCCAC
14651 TATGCCTGGC TAATTTTTTG TATTTTTAGT AGAGACGGGG CTTTGCCATG
14701 TTGGCCAGGC TGGTCTTGAA CTCCTGACCT CGTGATCCAC CCGCCTTGGC
14751 CTCCCAAAGT GCTGGACTA CAGGCGTAAG CCACTGTGCT CGGCCCTATA
14801 TTTTTTTCAG ATAGCCAGTT ATCCTAATGC TCCCTTGATT TGATGGACCA
14851 CCTGGATCAC ACATTATGAG CCCCCTCATA AGCAGGTGGG AGTCTCAAGC
14901 GAGGGCCAGT CCCGATGGGA ATAGCACTTG GTGGCTGAGG ACCCTCCTAT
14951 CTGTGCAGAC ACTGTTGTAA AACTTCACAT GCATCATCTA ATTTAGTCCT
15001 CACCAAAATC CTATGAAATG TAGGAATGAT CATTACACCC ATTTATAGAT
15051 AAGGAAACGG AGGGACAGGG AGATTACTCC GCTACAGGTC AAGAGGCAGG
15101 GAAGTAGAGC TGCGATTTGA ACTGAGGTCT GTGTCTAGAA CACGTGCTCA
15151 TTCTTTCCCT AAAATGTATT CATAGGTGAA AAAGGGCTTC TGCGGAAAGC
15201 CCTGGGTTAT GTGGGAAACC CTGGATTTAC AGCTGTCTTT CCAGCAGGAT
15251 GATGCAGGAG AGAGAGGGAT GCGATTCTC CCAATCTCTC CTGGTCCCAG
15301 AACTCATTAG AGAGTTCTCC CTGCTGAGGG CTCCCGACTG GTGTTGCACA
15351 CAGTACACTT CGGGAGCCCG AGGCTGATGG TTCCATGGAA AGTACACAGT
15401 CATTTTAGTT TGCACACCAA GTGTGAAGTG GCAGGACAG GCCACTGTTC
15451 TGAGAAGGAA CCCAGGGAAA GGGACTGGCC CAAGACCACA CACTGGTTAG
15501 CGGCACTTCC CACATCTGCC TGACCCCTAG TCCAGTGCCG CCTTTTCTTT
15551 ACTCTGCAAC AGGAGTCCAA AATCAGGAGT TCCATGAGGA CACTGGGAAC
15601 AGTGGGATGG GTTAGGCCAG CGGTGGATGG TTCTGGGGAG GGCCCGAGCT
15651 GAAGCGCCCC CGCAACTCCC CACAGGGATG GCTGCATCAG CAGGGAGGAG
15701 ATGGTTTCCT ATTTCCTGCG CTCCAGCTCT GTGTTGGGGG GGCGCATGGG
```

FIGURE 3

```
15751 CTTCGTACAC AACTTCCAGG AGAGCAACTC CTTGCGCCCC GTCGCCTGCC
15801 GCCACTGCAA AGCCCTGGTG AGAGTCCCTT TCCCGGCTCA CGGCCCAAGC
15851 CACGCCCCTC CAGCCCCGGC CCCGCCCTCC CTTCTGGCCC CGCCTCTGCC
15901 AGAGCCCTTC TCAAGCCAGG AAAACCTGGT AATTCTATTT GCCTCTCCTC
15951 CTGTGGTTCT GCCCGGGGCC CTGAGGCGGG CTCTAAAGCC CTAGTCTCAC
16001 CCTCAAGAAG GAAGAAGTAG AGTCATCACC TCTAAATCCC TCCTCCCACC
16051 ACGGCCCCTC CTCTATTGCA GATCCTGGGC ATCTACAAGC AGGGCCTCAA
16101 ATGCCGAGGT GAGATGGAAT GACTGGAAGG GCTGCTGGGC AGTGTTTTTT
16151 TTGTTTGTTT GTTTGTTTGG GAGAGTTACT ATTTTGGTGG GGCAATTGCC
16201 AAGGAGTGAA GTACCTTAAA ATCAGAGGCG CATGGCCGGG CATGGTGGCT
16251 CAAGCCTGTA ATCCCAGCAC TTTGGGAGGC CGAGGCGCGC AGATCACCTG
16301 AGGTCAGGAG TTCAAGACCA GCCTGACCAA CATAGCGCAA CCCCGCCTCT
16351 ACTAAAAATA CAAAAGTAG CTGGGCGTGG TGGCACCCAC CTGTAATCCC
16401 AGCTACTTGG GAGGCTGAGG CATGAGAATC GCTTGAACCT GGGAGGCGGG
16451 GTTTGCAGTG AGCCGAGATC ACGCCACTGC ACTCCAGCCT GGGCAACAGA
16501 GAGGGCTCTG TCTCAAAAAA AAAAAACAAC AAAAAAACCC CCAAAACCAA
16551 AACCCCACAA AATCAGAGGC TCAAGATGAC TGATGTGAAG GGAGTGGCGT
16601 TTAAGAGGCC ATTTATTTTG ATGACGCAGC TGCCCAGGAA CAGAGAACAT
16651 GGGAGAAGGC ATAGACTGAC AATTAGGAGG AGGAGAACAC TTTGGAAGGA
16701 GACTCTTATT TTGGTGGGGC AGCTGCTCAG GAACAAAGGT TCCTGGTAGG
16751 GGGGCGCAAG CCTGCGGGAT GGGATGGAGG GTATTCTGAC CAATGTCCCT
16801 GGCTGGCTCT CCATTTGCTC TCCCCCAGCC TGTGGAGTGA ACTGCCACAA
16851 GCAGTGCAAG GATCGCCTGT CAGTTGAGTG TCGGCGCAGG GCCCAGAGTG
16901 TGAGCCTGGA GGGGTCTGCA CCCTCACCCT CACCCATGCA CAGCCACCAT
16951 CACCGCGCCT TCAGCTTCTC TCTGCCCCGC CCTGGCAGGC GAGGCTCCAG
17001 GCCTCCAGGT AAGAGGGAGT CATTCTGTAC TGGCCTGTGG AGGGAAGGAT
17051 GCAGGGCTAC TGGGGCAAAG AACGCAGGAT GGAAGCCATT CCAAAGTGCA
17101 TAATTCTCTT TTTGTGGTGG GATAATAAAG AAGGGACAGG CCGGGCGCGG
17151 TGGCTCACGC CTGTAATCCC AGCACTTTGG GAGGCCGAGG CGGGCGGATC
17201 ACGAGGTCAG GAGATCGAGA CCATCCTGGC TAACACGGTG AAACCCCATC
17251 TTTACTAAAA ATACAAAAAA AAAAAATTAG CCAGGCGTGG TGGCGGACGC
17301 CTGTAGTCCC AGCTACTTGG GAGGCTGAGG CAGGAGAATG GCATGAACCC
17351 GGGAGGCGGG GCTTGCAGTG AGCCGAGATC GCGCCACTGC ACTCCAGCCT
17401 GGGCGATAGA GCAAGACTCC GTCTCAGAAA AAAAAAAAAT AAAAAATAAA
17451 GAAGGGACAG GTAAGGGTGC CAGAAAGTGG CCAGGAAGCC CTGGACCTTC
17501 TGAGGCTGAG GAGAGAGACC CTAATTTATA AAGAGGTATA AAAGTGAAAG
17551 AGGCTTCAAG ATTCCAGTTA CAGTCTTATT TTGTTGGAGG GGTTAACAAA
17601 GGATTGGAGA AGGTGTTATA TGAGCCATTG GCTTGCCTTT CCCTTTCTGG
17651 CTGCTCTGGA GGCTCTTCTG GGGAAAGTCC CTTGCCCTGA TAATGTCCTG
17701 GCAGCTCTCT TGGGGTATTT GATGGTTTTA GGTCAGTTTG CTGAATGACA
17751 ACTGGCCAAA TGATTATTTT GCTGAGAACA GTCCGAACAA CTATGTTAAA
17801 CTGGGGTCTA AGGTAGTTGA TCACAACTGT TTGGGTTGGC ATAAGTCCTC
17851 AAAAACAGA GGCAGGCACA GGGCATACAT CCTCAAAAAT AGAAAAGATA
17901 AATCCATTTG CATTGAGCCT TCCAGAAGTG CTGGGGTCTA AAATGTGAAA
17951 TACACACAAA ATTGACATTT AAGCAAACTG CGCTGACAAA TCTGTGGCTG
18001 AAAAGCTGT GGCAAAACAA AAACATAGAA AAAGAGCCTC AAAAATTGGG
18051 CTGAGGCCAG GCATGGTGGC TCACGCCTGT AATCCTAGCA CTTTGGGAAG
18101 CCAAGGTGGG TGGATCACCC GAGGTCAGGA GTTGGAGACC AGACTGGCCA
18151 ACGTGGCAAA ACATCATCTC TACAATACAA AAATACAAAA ATTAGCTGGG
18201 CGTGGTGGCA GGCGCCTGTA ATCCCAGCTA CTTGGGAGGC TGAGGCACGA
18251 GAATCGCTTG AACCTGGGAG GTGGAGGTTG CAGAGAGCCG AGATTGCGCC
18301 ATTGCACTCC AGCCTGGGCG ACAGAGAGAG ACTCTGTCTC AAAAAAAAAA
18351 AAAAAAAAA AAATTGGGCT GTGAGGTCAT GCAGGGAATT GATTTTTGGT
18401 GGGTGGGTCT GCTTCTGGGA TGATGTGGAT GCCTCCCGTG GAGAGGGGAA
18451 GGGTTGATGA AGTCCCAGGG ACCTGGAAGT GTGTTCTGCA GCAATCCCCC
18501 TCCCAGCAGA GATCCGTGAG GAGGAGGTAC AGACGGTGGA GGATGGGGTG
18551 TTTGACATCC ACTTGTAATA GATGGTGAGT CCTCCCACAG CTGGCACCAG
18601 AGCTCCCCAC TGAGGGCTGG GGGGAGCTG GGGAGTATCA GGGAAATGGG
18651 TGCTTTATCC AAATGGCTCC AAGCCAGGTG GGCTACTACC TTGTTGTTAG
18701 GGGGGTGTCT TCCTCACAAC CTGTTTTTCT CTTCCCAGCT GTGGTTGGAT
18751 CAAGGACTCA TTCCTGCCTT GGAGAAAATA CTTCAACCAG AGCAGGGAGC
18801 CTGGGGGTGT CGGGGCAGGA GGCTGGGGAT GGGGGTGGGA TATGAGGGTG
18851 GCATGCAGCT GAGGGCAGGG CCAGGGCTGG TGTCCCTAAG GTTGTACAGA
```

FIGURE 3

```
18901 CTCTTGTGAA TATTTGTATT TTCCAGATGG AATAAAAAGG CCCGTGTAAT
18951 TAACCTTCAC CATCAGCGCC TAGAATCCCG GGGGGTAGGG GGATGGTATA
19001 CTTTACAGGA TGACAATCTT GGGAGCTAGA ACTTTGTAGC CAGAGAAACT
19051 TGGGAGGTCT GGAATCTCAT GTGTCTGGAG TCTTGGGGAA GAGAATCTTA
19101 GAAGCAGAAA ACCTTGGAAC ATAAGAATCT TGGGGAGGGT CTAGGATCTT
19151 GAGGAGACCA GATCCTTGGA CATCTAAAAC TTGAAACTAG TAGGTCTGCA
19201 CCCGAGAATT GCAGGGCCAG TCATGCATAC CCAAAGCCTT CAGCCCATGG
19251 CCGAAATTCC CTTGCTGGAC AGGGGGCCTT TCAGCCCCTG CTTGGACGCT
19301 TCCAGTAACA GGGCCCTCAC TGCAGGAATC GTGGGAGGGA GAGGGGCAGC
19351 ACAGAGTTGC TGGCTGTCGG GGAAGGGAGG GAGGGCCCTG GGCAGTCCGA
19401 GGGCCCTGCT GGGCTTGTGC CTCAGGGTGG GGGCTGCACT CCTCCGCCTT
19451 GCAGCCTCCT GGCCTGGTGC TGCTGCCAGC CGGAAGGACA GTGACTTCCA
19501 GAGGAAATGC ATATTGATCC TGCTTTCAGC CTCCGGTGGT GGCTTCTCCC
19551 AACCCAGCTC TTCCCTCCTG AGCCTGCAGC ACGGAGGTTT TGGGGGTCAC
19601 TGCTACCTAA AGAAGGCTAA GGCCACTTCT GAGGCTGGTC TGGGAGTTTA
19651 CTAAAGGTTC TGAAGCTGGG CCGGGCTGCC CCTGGGATCA GGAGACTCCA
19701 GACAGCAGTC CTGACAATGG GAACTACCTC CTCAGTCCCC CAAACTGGGA
19751 GGTGTCCCAC AGCAGCTGTA GGATTGTCCT AGGGGTGGAG ACCTGAGCAC
19801 CTTCCACTCC AAAGCACAGT ATCTGTGGGC CTGGCAGTGG CCTCAGTTCC
19851 CCATGAGTG CCCCGGTCCC CCACCCCAGG GTTTCCCCAC ATCACATCCA
19901 TCCCTGCTTT GAGACCCCAC TCCCCCTGGC CTGTTCTTTA TTTTGGGTCA
19951 CTCCCTTCTC TTTCCTGGTC ATATCTCTCC TGCAGGCCTA CCCTGTGTTG
20001 GGCCCCCCAG CCCTGTCTCT GCATCGGGTG CCCCCCTGCC CCTCCTTCTG
20051 TCCTCAGCCC CCTCCGCCCT TCCCCCTCTT GAGGCTGTAA TATCCGTTTC
20101 ACGATTTGGG GGCTGAGTTG CTATAACAAC AGACGGCGAT TGTGTTGTGA
20151 AGAGCAGCTC GCTCCTGTGC CGCCTGCCTC CTGTGCTGCC TCCATCCCTG
20201 CAGCCCAGTC GGTTCCTCTT GGCTCCTCTC GTCACTACCC TCCAGTTCCA
20251 GTCTGGCCTC TTCCTGGTGT GTGTGTGTGT GTGTGTGT GTGTGTGTAT
20301 GCATGCATGC ATATGTGTGT CCAGGTCTGC CTGCCCGGGA TGTGACAAGT
20351 AGCGGTCTTC ATGGTTGCAT GTGTCTGAAT TTGGTGTCTG AGCTTCACAT
20401 TGTATGCGCC TGTGTGCATG TGTGTGCATG GACATGCATG CTGTATCTGC
20451 TGTGTTTCCC CTCCCCCATG TGTCCCCACT GGCCTTTGCA CATGGGAGAA
20501 GGGCATGTGC TCAGCATATC ACTCAACTGT CCACATTGGG TGGGTACCTG
20551 TGTGTGGTGT GTGTGTGTGG GGGGTGTGTC TTGAAGTGGC AGGTCCCAAA
20601 TGCTTAGGCA ATCTGAACCT TGGACCTTGC AGAGAGGAGA GATGTCCCTG
20651 TAGGTGGGAG GGACAGGGAG ATGCAGCAGC TGCCCGGTGA CCTTTTCTGC
20701 CCTTGATGGG CAAAGCTGGG GGTAGGGAAA GGAGACAAGT GCTCATACTT
20751 ACCTCCCTCC CTGCCCAGGC TCCTCTGTAA GGGTCTGAGT CTGTCTCTGT
20801 GAGCCATTGC ATCTGTCTGT CTATGCCCTG ATGCCTGGAT GGACAAGGGG
20851 TGTGTGTGTG TGTGTGTGTG TGTGTGTGTG AGTGTGAGGC TGCAGGAAGA
20901 GGAACAGTGG GGGATGGGCA GGAAAGTGGG CTGTGGGGTC AGGGAGGCGA
20951 T   (SEQ ID NO:3)
```

FEATURES:
Start:    3000
Exon:     3000-3072
Intron:   3073-3753
Exon:     3754-3855
Intron:   3856-4363
Exon:     4364-4427
Intron:   4428-4786
Exon:     4787-4918
Intron:   4919-5702
Exon:     5703-5853
Intron:   5854-6056
Exon:     6057-6230
Intron:   6231-6389
Exon:     6390-6506
Intron:   6507-8832
Exon:     8833-9114
Intron:   9115-9885
Exon:     9886-9963

FIGURE 3

```
Intron:   9964-10201
Exon:    10202-10324
Intron:  10325-10638
Exon:    10639-10754
Intron:  10755-15675
Exon:    15676-15817
Intron:  15818-16071
Exon:    16072-16108
Intron:  16109-16828
Exon:    16829-17008
Intron:  17009-18491
Exon:    18492-18565
Stop:    18566
```

CHROMOSOME MAP POSITION:
Chromosome 11

ALLELIC VARIANTS (SNPs):
DNA

| Position | Major | Minor | Domain |
|---|---|---|---|
| 5539 | C | G | Intron |
| 5658 | T | G | Intron |
| 5861 | C | T | Intron |
| 6023 | A | G | Intron |
| 6799 | C | T | Intron |
| 9579 | C | A | Intron |
| 9842 | T | C | Intron |
| 10159 | T | C | Intron |
| 12025 | A | - G | Intron |
| 14723 | T | C | Intron |
| 14996 | G | A | Intron |
| 16153 | T | G | Intron |
| 16181 | G | A | Intron |
| 16756 | A | G | Intron |
| 18059 | A | G | Intron |
| 18364 | A | - T | Intron |
| 18861 | G | A | Beyond ORF(3') |
| 20443 | G | A | Beyond ORF(3') |
| 20881 | A | T | Beyond ORF(3') |

Context:

DNA
Position
5539    AGACTCAGTTCAGGCATGAAGTCTCCGTGGGCTCTGAGGGTTCGGGGCTCTTCCGGGGTA
        GAATTTGTCGTTCCCACCTCTGTTTTCCATGGCACTTTGTACAGACTCCTGTACAAAGAC
        CTCTGTACATGTGTCACGCTGTTTTGTGATCATGTGTTTCTGTGTCTGTCTCCCTCAGTA
        GACTGTGAGCTCCTCGAGGGCAGGAACCGTGTCTTACTCATCTCTGTATTCCCAGCGCCT
        AGCACAGTGCCTGGCACAGAGTACGTTGTTCATAAATGTGTGTTGAGTGCATGACGGGGT
        [C,G]
        GGGGGAGATGAGGAGGAGTTGCTGGGACTGGGAACATTCGTGCCTAGGACAGTGCCTCGC
        ATTATGTAGGTTCTCAGTAAGCGTGAATGGTGTGTCTGTGTGAGTGGGGGGCCACGAGGC
        ATGCGCATGTCCAGCAAAGGGCTCACTACCCCTGCCCCCCCAGCCCTACCTACAAGTGGA
        AGCGGCAGGTGACTCAGCGGAACCCTGTGGGACAGAAAAAGCGCAAGATGTCCCTGTTGT
        TTGACCACCTGGAGCCCATGGAGCTGGCGGAGCATCTCACCTACTTGGAGTATCGCTCCT 5658    CCTCTGTACATGTGTCACGCTGTTTTGTGATCATGTGTTTCTGTGTCTGTCTCCCTCAGT
        AGACTGTGAGCTCCTCGAGGGCAGGAACCGTGTCTTACTCATCTCTGTATTCCCAGCGCC
        TAGCACAGTGCCTGGCACAGAGTACGTTGTTCATAAATGTGTGTTGAGTGCATGACGGGG
        TGGGGGGAGATGAGGAGGAGTTGCTGGGACTGGGAACATTCGTGCCTAGGACAGTGCCTC
        GCATTATGTAGGTTCTCAGTAAGCGTGAATGGTGTGTCTGTGTGAGTGGGGGGCCACGAG

FIGURE 3

```
          [T,G]
          CATGCGCATGTCCAGCAAAGGGCTCACTACCCCTGCCCCCCCAGCCCTACCTACAAGTGG
          AAGCGGCAGGTGACTCAGCGGAACCCTGTGGGACAGAAAAAGCGCAAGATGTCCCTGTTG
          TTTGACCACCTGGAGCCCATGGAGCTGGCGGAGCATCTCACCTACTTGGAGTATCGCTCC
          TTCTGCAAGATCCTGGTGCGGCCCGAGGGCTGGGGGGTCAGGGGTCCAATGTGGGCTGGA
          AGAGAGTTCTAGGAGGGGCAGGGTCCCTGGCGTAGGCTGGGTCACAGGGTGCATCAGGGG

5861      CTGGGACTGGGAACATTCGTGCCTAGGACAGTGCCTCGCATTATGTAGGTTCTCAGTAAG
          CGTGAATGGTGTGTCTGTGTGAGTGGGGGGCCACGAGGCATGCGCATGTCCAGCAAAGGG
          CTCACTACCCCTGCCCCCCCAGCCCTACCTACAAGTGGAAGCGGCAGGTGACTCAGCGGA
          ACCCTGTGGGACAGAAAAAGCGCAAGATGTCCCTGTTGTTTGACCACCTGGAGCCCATGG
          AGCTGGCGGAGCATCTCACCTACTTGGAGTATCGCTCCTTCTGCAAGATCCTGGTGCGGC
          [C,T]
          CGAGGGCTGGGGGGTCAGGGGTCCAATGTGGGCTGGAAGAGAGTTCTAGGAGGGGCAGGG
          TCCCTGGCGTAGGCTGGGTCACAGGGTGCATCAGGGGTTTCAGTGTAACCACTGAAGGTC
          AGCTGGAGGGTGAGGAGTGGCTATCAGTGAGGGGAGAGGCCGGCAAGGTGCTGAGGCCAC
          TCCTCATGCCCCAGTTTCAGGACTATCACAGTTTCGTGACTCATGGCTGCACTGTGGAC
          AACCCCGTCCTGGAGCGGTTCATCTCCCTCTTCAACAGCGTCTCACAGTGGGTGCAGCTC

6023      GGCAGGTGACTCAGCGGAACCCTGTGGGACAGAAAAAGCGCAAGATGTCCCTGTTGTTTG
          ACCACCTGGAGCCCATGGAGCTGGCGGAGCATCTCACCTACTTGGAGTATCGCTCCTTCT
          GCAAGATCCTGGTGCGGCCCGAGGGCTGGGGGGTCAGGGGTCCAATGTGGGCTGGAAGAG
          AGTTCTAGGAGGGGCAGGGTCCCTGGCGTAGGCTGGGTCACAGGGTGCATCAGGGGTTTC
          AGTGTAACCACTGAAGGTCAGCTGGAGGGTGAGGAGTGGCTATCAGTGAGGGGAGAGGCC
          [A,G]
          GCAAGGTGCTGAGGCCACTCCTCATGCCCCAGTTTCAGGACTATCACAGTTTCGTGACT
          CATGGCTGCACTGTGGACAACCCCGTCCTGGAGCGGTTCATCTCCCTCTTCAACAGCGTC
          TCACAGTGGGTGCAGCTCATGATCCTCAGCAAACCCACAGCCCCGCAGCGGGCCCTGGTC
          ATCACACACTTTGTCCACGTGGCGGAGGTGCCTGCCCCTCCCTCCCGGTGTCTCCCAACC
          ACCCCACATGCCAGTCAGGCCAACCCTTCCCTTCCCCTAACCCACTGCCTTCTCTCTAGA

6799      CCATCAAGGTGCCTGGGACTGGGGAGGGGCCGGTGCTTCCCAGGTCTGTCTTCACTGGGT
          CCTCCCAGCAGCACTGGGGGCTGGGCACAGCTGTCCTCATTTGATAGATATGGAAATGGA
          GGCTCAGAGGGGTTAAGTGCTTTTCTCAGTTTGCACAATGGCAACAGCAGAGTGGGGGCT
          CACAGGTCGTCAGGGACCCCAAAGCTAGTACTTTTTTTTTTTTTTTTTAAGACAGGGTCTC
          TCTCTCTGTTGTCCAGACTGGAGTTCAGTGGTGCAGTCACAAGCTCACTGCAGCCTTGAA
          [C,T]
          TCCTGAGCTCAATCGATCCTCCCACCTCAGCCTCCTGAGTAGCTGGGACTACAGGTGTAC
          GCCACCATGCCTAATTTTTGTATTGTTATTAATTTTTTTTTTTTTTTTAGAGATGGGG
          TTTTGCCATGTTGCCCAGACTGGTCTTGAACTCCTGGGCTCAAGTGATCCGCCTGCCTTG
          GCCTCCCAAAGTGCTGAGATTATGGCTTGAGCCATTGTGCCTTGCCACTTGTAGTTTCTT
          CTTTTCTTTCTCCTTCATTTTTTATTATTTTTGAAGTATTTTGAAGTATTGAGTAACATA

9579      CTGGTTGGGGCTGTGGACTGAGGTCTGATCTCCAGGCTGGTATGTGGACTGTGGGCAGTT
          TGAACTGGGCCTGGGTCCCGGGTTGAGTTCTGGCAATGGGCTGTGTTCTAGGGCTGGGCC
          AAGCTCTGCATTCTGTGGGCAGGGGTGGTTTCTAAGCATGGCCCTGGGCTCGGAGTGAAG
          TTCTGGGCTTGGCTTTACACTTGGTCTTGGGGTCTAGGGTGGGAGTTGGGTTCTGGTTTA
          GATCCAGACAAGGTTCTAGACATTGGGCTGGGGCTTAAGTGTTAAGGTTTGGAGTGGATT
          [C,A]
          TTAGCTGCTTCTGGGCTCTGGAGGGGATCAGGGTTGAAATCAGAGCTTCTGGCTGGGTTC
          CGACCTGGCTTCTTCCCTGACATCTTGGCAATATGTTGTGTTCAAGGTTTGGGGCCATGC
          TGTGGTTTGATCTGTGCGCTGGGATGACATGGGGGTTGCTGTGCTGTGTTCTAAGCCAGG
          CTTTGTCCTGAGTCTAGCTTCTGACCCGAGCTCTGGCTGAGCTGTGGCCTCTAGGTCGAC
          CTTTGGCCCTGGGCTCTGTGGCCGTGGGCAGGGGCCAGTGGGGGTGATCAGATCTGTGTG

9842      TGGGCTGGGGCTTAAGTGTTAAGGTTTGGAGTGGATTCTTAGCTGCTTCTGGGCTCTGGA
          GGGGATCAGGGTTGAAATCAGAGCTTCTGGCTGGGTTCCGACCTGGCTTCTTCCCTGACA
          TCTTGGCAATATGTTGTGTTCAAGGTTTGGGGCCATGCTGTGGTTTGATCTGTGCGCTGG
          GATGACATGGGGGTTGCTGTGCTGTGTTCTAAGCCAGGCTTTGTCCTGAGTCTAGCTTCT
          GACCCGAGCTCTGGCTGAGCTGTGGCCTCTAGGTCGACCTTTGGCCCTGGGCTCTGTGGC
          [T,C]
          GTGGGCAGGGGCCAGTGGGGGTGATCAGATCTGTGTGTCCCAGGTGTCTCTGGATCAGTA
          TCAGACGGAGGATGAGCTGTACCAGCTGTCCCTGCAGCGGGAGCCGCGCTCCAAGTCCTC
```

FIGURE 3

```
              GGTGAGGGGGTACTCCCTCCTCTCCACTCTGCCCTTCCCTCCTGAGAATCCCAGGATGTG
              AGGATGGGAAGAGCTCTTAGCAGCCACCTCACCCATCCATCTTGTAGGACAGAGGCATCC
              TGGGGGTAGGGCAGTAGTGTTGGGCAGACTTCCCTCTCCCAGGGATTCCCCTCTCTGTTC

10159   GGGGGTGATCAGATCTGTGTGTCCCAGGTGTCTCTGGATCAGTATCAGACGGAGGATGAG
              CTGTACCAGCTGTCCCTGCAGCGGGAGCCGCGCTCCAAGTCCTCGGTGAGGGGGTACTCC
              CTCCTCTCCACTCTGCCCTTCCCTCCTGAGAATCCCAGGATGTGAGGATGGGAAGAGCTC
              TTAGCAGCCACCTCACCCATCCATCTTGTAGGACAGAGGCATCCTGGGGGTAGGGCAGTA
              GTGTTGGGCAGACTTCCCTCTCCCAGGGATTCCCCTCTCTGTTCCCCGGGGCTCTGGGCT
              [T,C]
              CCCCTGCCTCTGGCCCTAGCTCAGGCCCGACCATTTCCATAGCCAACCAGCCCCACGAGT
              TGCACCCCACCACCCCGGCCCCCGGTACTGGAGGAGTGGACCTCGGCTGCCAAACCCAAG
              CTGGATCAGGCCCTCGTGGTGGAGCACATCGAGAAGATGGTGGAGGTGAGCTCCTGCGGA
              GCCTGAGCAGTGTGTGGGGAGAGGCCAGTTTGCCGGAGCACTGCCCTGGAAGCCAGCACG
              AGTGTCCTGTTCAAGACCCAGCACTCAGCCCCTAGGAGTCACAGGGCCTGGCAGGCCAGC

12025   TGGGGTTTTACCATGTTGGCCAGGCTGGTCTCAAACTCTTGACCTCAAGTGATCTACCTG
              CCTTGGCCCCCCAAAGTGCTAGGATTACAGGCATGAGCTACTGCTCCTAGCCTAAAAAAA
              TTTTTTTTGGGCATGGGTGGCACGTGCCTGTAGTCCCAGCTACTCAGGAGGCTGAGGCAG
              GAGGAACCCTTGAGCCCAGGAGGTTGAGACTGCAGTGAGCTGTCATCACACCACTGCACT
              TCAGCCTGGGTGACTGCGCGAGATCACCCCCATCAAAAAAAAAAAAAAAAGAAAAAAAAA
              [A,-,G]
              GAAGAAATGAAAGTCCCCTCTTTCCTTTTCCACTGGTAGAAGTTGCCATGATTAAGCACT
              GTTAACAATATTAAGCTTGGCAGTATGTGGATTCTTCCAGTCTTCTTTTCCCAGGCAGGT
              GCACATTGATAGAGATTTTGTTTGTTTGGTGTCTGTTTCATGGACAAACAGGATTAGAGC
              ATAAATCTAGTTCTGCTTGTGGCTTTTATCATAGCTGCTTTATTTCTTCTCCCAGATTTT
              AGGCAGAGGTAGTTGAGTTCCATGTTTTCTCCCTGGGTTGGTGGGTGGATTTTTATCTAG

14723   GGCTTCTGGGATTTGTGTTCGGGGTAGAAAGGCCCTCAGCCCCTCAAGATTATAAAATTA
              TAAAACCTTTTCTTTTTTTTTTTTTTTCTGAGACAGGGTGTCTTGCCATGTCACCCAGG
              CTGGAGTGCAGTGGCATGATCTTGGCTCGCTGCAACCTCCACCTCCCAGGTTCAAGTGAT
              TCTCGTGCCTTAGCCTCCCGAGTAGCTGGGATTATAGGTGCCTGCCACTATGCCTGGCTA
              ATTTTTTGTATTTTTAGTAGAGACGGGGCTTTGCCATGTTGGCCAGGCTGGTCTTGAACT
              [T,C]
              CTGACCTCGTGATCCACCCGCCTTGGCCTCCCAAAGTGCTGGGACTACAGGCGTAAGCCA
              CTGTGCTCGGCCCTATATTTTTTCAGATAGCCAGTTATCCTAATGCTCCCTTGATTTGA
              TGGACCACCTGGATCACACATTATGAGCCCCCTCATAAGCAGGTGGGAGTCTCAAGCGAG
              GGCCAGTCCCGATGGGAATAGCACTTGGTGGCTGAGGACCCTCCTATCTGTGCAGACACT
              GTTGTAAAACTTCACATGCATCATCTAATTTAGTCCTCACCAAAATCCTATGAAATGTAG

14996   CCATGTTGGCCAGGCTGGTCTTGAACTCCTGACCTCGTGATCCACCCGCCTTGGCCTCCC
              AAAGTGCTGGGACTACAGGCGTAAGCCACTGTGCTCGGCCCTATATTTTTTCAGATAGC
              CAGTTATCCTAATGCTCCCTTGATTTGATGGACCACCTGGATCACACATTATGAGCCCCC
              TCATAAGCAGGTGGGAGTCTCAAGCGAGGGCCAGTCCCGATGGGAATAGCACTTGGTGGC
              TGAGGACCCTCCTATCTGTGCAGACACTGTTGTAAAACTTCACATGCATCATCTAATTTA
              [G,A]
              TCCTCACCAAAATCCTATGAAATGTAGGAATGATCATTACACCCATTTATAGATAAGGAA
              ACGGAGGGACAGGGAGATTACTCCGCTACAGGTCAAGAGGCAGGGAAGTAGAGCTGCGAT
              TTGAACTGAGGTCTGTGTCTAGAACACGTGCTCATTCTTTCCCTAAAATGTATTCATAGG
              TGAAAAAGGGCTTCTGCGGAAAGCCCTGGGTTATGTGGGAAACCCTGGATTTACAGCTGT
              CTTTCCAGCAGGATGATGCAGGAGAGAGAGGGATGCGATTTCTCCCAATCTCTCCTGGTC

16153   CGCCCCTCCAGCCCCGGCCCCGCCCTCCCTTCTGGCCCCGCCTCTGCCAGAGCCCTTCTC
              AAGCCAGGAAAACCTGGTAATTCTATTTGCCTCTCCTCCTGTGGTTCTGCCCGGGGCCCT
              GAGGCGGGCTCTAAAGCCCTAGTCTCACCCTCAAGAAGGAAGAAGTAGAGTCATCACCTC
              TAAATCCCTCCTCCCACCACGGCCCCTCCTCTATTGCAGATCCTGGGCATCTACAAGCAG
              GGCCTCAAATGCCGAGGTGAGATGGAATGACTGGAAGGGCTGCTGGGCAGTGTTTTTTTT
              [T,G]
              TTTGTTTGTTTGTTTGGGAGAGTTACTATTTTGGTGGGGCAATTGCCAAGGAGTGAAGTA
              CCTTAAAATCAGAGGCGCATGGCCGGGCATGGTGGCTCAAGCCTGTAATCCCAGCACTTT
              GGGAGGCCGAGGCGCGCAGATCACCTGAGGTCAGGAGTTCAAGACCAGCCTGACCAACAT
              AGCGCAACCCCGCCTCTACTAAAAATACAAAAAGTAGCTGGGCGTGGTGGCACCCACCTG
              TAATCCCAGCTACTTGGGAGGCTGAGGCATGAGAATCGCTTGAACCTGGGAGGCGGGGTT
```

FIGURE 3

| | |
|---|---|
| 16181 | CTTCTGGCCCCGCCTCTGCCAGAGCCCTTCTCAAGCCAGGAAAACCTGGTAATTCTATTT |
| | GCCTCTCCTCCTGTGGTTCTGCCCGGGGCCCTGAGGCGGGCTCTAAAGCCCTAGTCTCAC |
| | CCTCAAGAAGGAAGAAGTAGAGTCATCACCTCTAAATCCCTCCTCCCACCACGGCCCCTC |
| | CTCTATTGCAGATCCTGGGCATCTACAAGCAGGGCCTCAAATGCCGAGGTGAGATGGAAT |
| | GACTGGAAGGGCTGCTGGGCAGTGTTTTTTTTGTTTGTTTGTTTGGGAGAGTTACT |
| | [G,A] |
| | TTTTGGTGGGGCAATTGCCAAGGAGTGAAGTACCTTAAAATCAGAGGCGCATGGCCGGGC |
| | ATGGTGGCTCAAGCCTGTAATCCCAGCACTTTGGGAGGCCGAGGCGCGCAGATCACCTGA |
| | GGTCAGGAGTTCAAGACCAGCCTGACCAACATAGCGCAACCCCGCCTCTACTAAAAATAC |
| | AAAAAGTAGCTGGGCGTGGTGGCACCCACCTGTAATCCCAGCTACTTGGGAGGCTGAGGC |
| | ATGAGAATCGCTTGAACCTGGGAGGCGGGGTTTGCAGTGAGCCGAGATCACGCCACTGCA |
| | |
| 16756 | CAGTGAGCCGAGATCACGCCACTGCACTCCAGCCTGGGCAACAGAGAGGGCTCTGTCTCA |
| | AAAAAAAAAAACAACAAAAAAACCCCCAAAACCAAAACCCCACAAAATCAGAGGCTCAAG |
| | ATGACTGATGTGAAGGGAGTGGCGTTTAAGAGGCCATTTATTTTGATGACGCAGCTGCCC |
| | AGGAACAGAGAACATGGGAGAAGGCATAGACTGACAATTAGGAGGAGGAGAACACTTTGG |
| | AAGGAGACTCTTATTTTGGTGGGGCAGCTGCTCAGGAACAAAGGTTCCTGGTAGGGGGGC |
| | [A,G] |
| | CAAGCCTGCGGGATGGGATGGAGGGTATTCTGACCAATGTCCCTGGCTGGCTCTCCATTT |
| | GCTCTCCCCCAGCCTGTGGAGTGAACTGCCACAAGCAGTGCAAGGATCGCCTGTCAGTTG |
| | AGTGTCGGCGCAGGGCCCAGAGTGTGAGCCTGGAGGGGTCTGCACCCTCACCCTCACCCA |
| | TGCACAGCCACCATCACCGCGCTTCAGCTTCTCTCTGCCCCGCCCTGGCAGGCGAGGCT |
| | CCAGGCCTCCAGGTAAGAGGGAGTCATTCTGTACTGGCCTGTGGAGGGAAGGATGCAGGG |
| | |
| 18059 | AATGATTATTTTGCTGAGAACAGTCCGAACAACTATGTTAAACTGGGGTCTAAGGTAGTT |
| | GATCACAACTGTTTGGGTTGGCATAAGTCCTCAAAAAACAGAGGCAGGCACAGGGCATAC |
| | ATCCTCAAAAATAGAAAGATAAATCCATTTGCATTGAGCCTTCCAGAAGTGCTGGGGTC |
| | TAAAATGTGAAATACACACAAAATTGACATTTAAGCAAACTGCGCTGACAAATCTGTGGC |
| | TGAAAAAGCTGTGGCAAAACAAAAACATAGAAAAAGAGCCTCAAAAATTGGGCTGAGGCC |
| | [A,G] |
| | GGCATGGTGGCTCACGCCTGTAATCCTAGCACTTTGGGAAGCCAAGGTGGGTGGATCACC |
| | CGAGGTCAGGAGTTGGAGACCAGACTGGCCAACGTGGCAAAACATCATCTCTACAATACA |
| | AAAATACAAAAATTAGCTGGGCGTGGTGGCAGGCGCCTGTAATCCCAGCTACTTGGGAGG |
| | CTGAGGCACGAGAATCGCTTGAACCTGGGAGGTGGAGGTTGCAGAGAGCCGAGATTGCGC |
| | CATTGCACTCCAGCCTGGGCGACAGAGAGAGACTCTGTCTCAAAAAAAAAAAAAAAAAAA |
| | |
| 18364 | TGGTGGCTCACGCCTGTAATCCTAGCACTTTGGGAAGCCAAGGTGGGTGGATCACCCGAG |
| | GTCAGGAGTTGGAGACCAGACTGGCCAACGTGGCAAAACATCATCTCTACAATACAAAAA |
| | TACAAAAATTAGCTGGGCGTGGTGGCAGGCGCCTGTAATCCCAGCTACTTGGGAGGCTGA |
| | GGCACGAGAATCGCTTGAACCTGGGAGGTGGAGGTTGCAGAGAGCCGAGATTGCGCCATT |
| | GCACTCCAGCCTGGGCGACAGAGAGAGACTCTGTCTCAAAAAAAAAAAAAAAAAAAAAAA |
| | [A,-,T] |
| | TGGGCTGTGAGGTCATGCAGGGAATTGATTTTTGGTGGGTGGGTCTGCTTCTGGGATGAT |
| | GTGGATGCCTCCCGTGGAGAGGGGAAGGGTTGATGAAGTCCCAGGGACCTGGAAGTGTGT |
| | TCTGCAGCAATCCCCCTCCCAGCAGAGATCCGTGAGGAGGAGGTACAGACGGTGGAGGAT |
| | GGGGTGTTTGACATCCACTTGTAATAGATGGTGAGTCCTCCCACAGCTGGCACCAGAGCT |
| | CCCCACTGAGGGCTGGGGGGAGCTGGGGAGTATCAGGGAAATGGGTGCTTTATCCAAAT |
| | |
| 18861 | ACTTGTAATAGATGGTGAGTCCTCCCACAGCTGGCACCAGAGCTCCCCACTGAGGGCTGG |
| | GGGGGAGCTGGGGAGTATCAGGGAAATGGGTGCTTTATCCAAATGGCTCCAAGCCAGGTG |
| | GGCTACTACCTTGTTGTTAGGGGGTGTCTTCCTCACAACCTGTTTTTCTCTTCCCAGCT |
| | GTGGTTGGATCAAGGACTCATTCCTGCCTTGGAGAAAATACTTCAACCAGAGCAGGGAGC |
| | CTGGGGGTGTCGGGGCAGGAGGCTGGGGATGGGGGTGGGATATGAGGGTGGCATGCAGCT |
| | [G,A] |
| | AGGGCAGGGCCAGGGCTGGTGTCCCTAAGGTTGTACAGACTCTTGTGAATATTTGTATTT |
| | TCCAGATGGAATAAAAAGGCCCGTGTAATTAACCTTCACCATCAGCGCCTAGAATCCCGG |
| | GGGGTAGGGGGATGGTATACTTTACAGGATGACAATCTTGGGAGCTAGAACTTTGTAGCC |
| | AGAGAAACTTGGGAGGTCTGGAATCTCATGTGTCTGGAGTCTTGGGAAGAGAATCTTAG |
| | AAGCAGAAAACCTTGGAACATAAGAATCTTGGGGAGGGTCTAGGATCTTGAGGAGACCAG |
| | |
| 20443 | TGTTGTGAAGAGCAGCTCGCTCCTGTGCCGCCTGCCTCCTGTGCTGCCTCCATCCCTGCA |
| | GCCCAGTCGGTTCCTCTTGGCTCCTCTCGTCACTACCCTCCAGTTCCAGTCTGGCCTCTT |

FIGURE 3

```
         CCTGGTGTGTGTGTGTGTGTGTGTGTGTGTGTATGCATGCATGCATATGTGTGTCC
         AGGTCTGCCTGCCCGGGATGTGACAAGTAGCGGTCTTCATGGTTGCATGTGTCTGAATTT
         GGTGTCTGAGCTTCACATTGTATGCGCCTGTGTGCATGTGTGTGCATGGACATGCATGCT
         [G,A]
         TATCTGCTGTGTTTCCCCTCCCCCATGTGTCCCCACTGGCCTTTGCACATGGGAGAAGGG
         CATGTGCTCAGCATATCACTCAACTGTCCACATTGGGTGGGTACCTGTGTGTGGTGTGTG
         TGTGTGGGGGGTGTGTCTTGAAGTGGCAGGTCCCAAATGCTTAGGCAATCTGAACCTTGG
         ACCTTGCAGAGAGGAGAGATGTCCCTGTAGGTGGGAGGGACAGGGAGATGCAGCAGCTGC
         CCGGTGACCTTTTCTGCCCTTGATGGGCAAAGCTGGGGTAGGGAAAGGAGACAAGTGCT

20881    TTGAAGTGGCAGGTCCCAAATGCTTAGGCAATCTGAACCTTGGACCTTGCAGAGAGGAGA
         GATGTCCCTGTAGGTGGGAGGGACAGGGAGATGCAGCAGCTGCCCGGTGACCTTTTCTGC
         CCTTGATGGGCAAAGCTGGGGTAGGGAAAGGAGACAAGTGCTCATACTTACCTCCCTCC
         CTGCCCAGGCTCCTCTGTAAGGGTCTGAGTCTGTCTCTGTGAGCCATTGCATCTGTCTGT
         CTATGCCCTGATGCCTGGATGGACAAGGGGTGTGTGTGTGTGTGTGTGTGTGTGTGTG
         [A,T]
         GTGTGAGGCTGCAGGAAGAGGAACAGTGGGGGATGGGCAGGAAAGTGGGCTGTGGGGTCA
         GGGAGGCGAT
```

FIGURE 3

ISOLATED HUMAN RAS-LIKE PROTEINS, NUCLEIC ACID MOLECULES ENCODING THESE HUMAN RAS-LIKE PROTEINS, AND USES THEREOF

FIELD OF THE INVENTION

The present invention is in the field of Ras-like proteins that are related to the Ras guanyl nucleotide releasing protein subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

Ras-like proteins, particularly members of the Ras guanyl nucleotide releasing protein subfamilies, are a major target for drug action and development. Accordingly, it is valuable to the field of pharmaceutical development to identify and characterize previously unknown members of these subfamily of Ras-like proteins. The present invention advances the state of the art by providing a previously unidentified human Ras-like proteins that have homology to members of the Ras guanyl nucleotide releasing protein subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF) . . . ), insulin, an interleukin (IL), granulocyte colony-stimulating factor (G-CSF), granulocyte/macrophage colony-stimulating factor (GM-CSF).

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called "Raf protein", can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) which regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal transducing proteins are members of the Ras superfamily.

The Ras superfamily is a class of low molecular weight (LMW) GTP-binding proteins that consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization which is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I–IV) have been studied in the LMW GTP-binding proteins. Motif I is the most variable but has the conserved sequence, GXXXXGK. The lysine residue is essential in interacting with the .beta.- and gamma.-phosphates of GTP. Motif II, III, and IV contain highly conserved sequences of DTAGQ, NKXD, and EXSAX, respectively. Specifically, Motif II regulates the binding of gamma-phosphate of GTP; Motif III regulates the binding of GTP; and Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL 184 is a potential regulatory protein associated with Ca.sup.2+- dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Biol.) 340:267–271). All Rho proteins have a CAAX motif that binds a prenyl group and either a palmitoylation site or a basic amino acid-rich region, suggesting their role in membrane-associated functions. In particular, RhoD is a protein that functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of serine/threonine kinases that control cell growth and differentiation. Mutant Ras proteins, which bind but cannot hydrolyze GTP, are permanently activated and cause continuous cell proliferation or cancer. TC21, a Ras-like protein, is highly expressed in a human teratocarcinoma cell line (Drivas, G. T. et al. (1990) Mol. Cell. Biol. 10: 1793–1798). Rin and Rit are characterized as membrane-binding, Ras-like proteins without the lipid-binding CAAX motif and carboxy terminal cysteine (Lee, C. -H. J. et al. (1996) J. Neurosci. 16: 6784–6794). Further, Rin is shown to localize in neurons and have calcium-dependant calmodulin-binding activity.

Ras Guanyl Nucleotide Releasing Proteins

The novel human protein, and encoding gene, provided by the present invention is related to the family of Ras (and Rap) guanyl nucleotide releasing proteins (RASGRP or RasGRP), which are also referred to as guanine nucleotide exchange factors (GEFs), guanyl releasing proteins, and calcium- and diacylglycerol-regulated guanine nucleotide exchange factors (CALDAG-GEF). These proteins can activate both Ras and Rap proteins, particularly by switching Ras/Rap from the inactive GDP-bound state to the active GTP-bound state. The protein of the present invention shows a particularly high degree of similarity to Ras (and Rap) guanyl nucleotide releasing protein 2 (RASGRP2). Furthermore, the protein of the present invention may be an alternatively spliced variant of the protein provided in Genbank gi5031623. Specifically, the protein of the present invention has an additional 6 amino acids that are not present in the art-known protein of gi5031623 (see the amino acid sequence alignment in FIG. 2).

RASGRP2 is thought to play a critical role in neuronal function by controlling the relative activation of Ras and Rap1 signaling induced by calcium and diacylglycerol; furthermore, this control may be important for Ras/Rap modulation of both normal and malignant conditions. Rap proteins are members of the Ras small G protein family, are able to block Ras signaling via the Ras/Raf-1/MAP kinase pathway, and can also activate MAP kinase via B-Raf (Kawasaki et al., *Proc Natl Acad Sci U S A* 1998 Oct. 27;95(22): 13278–83).

RasGRP2 is targeted to the plasma membrane by N-terminal myristoylation and palmitoylation. RasGRP2 catalyzes nucleotide exchange on N-Ras, Ki-Ras, and Rap1. Expression of RasGRP2 has been observed to accelerate cell growth. RasGRP2 is a dual-specificity Ras and Rap exchange factor (Clyde-Smith et al., *J Biol Chem* 2000 Oct. 13;275(41):32260–7). RasGRP is also expressed in T cells and links T-cell receptors and phospholipase C-gammal to RasErk signaling; importantly, this pathway is readily amenable to therapeutic intervention (Ebinu et al., *Blood* 2000 May 15;95(10):3199–203).

For a further view of Ras/Rap guanyl nucleotide releasing proteins, see Kedra et al., *Hum. Genet.* 100: 611–619, 1997; Bottorff et al., *Genome* 10: 358–361, 1999; and Ebinu et al., *Science* 280: 1082–1086, 1998

The discovery of new human Ras-like proteins and the polynucleotides that encode them satisfies a need in the art by providing new compositions that are useful in the diagnosis, prevention, and treatment of inflammation and disorders associated with cell proliferation and apoptosis.

SUMMARY OF THE INVENTION

The present invention is based in part on the identification of amino acid sequences of human Ras-like protein polypeptides and proteins that are related to the Ras guanyl nucleotide releasing protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in humans in the testis, liver, brain glioblastomas, B cell chronic lymphatic leukemia, marrow, lymph (including germinal center B cells), and leukocytes.

DESCRIPTION OF THE FIGURE SHEETS

FIG. 1 provides the nucleotide sequence of a cDNA molecule that encodes the Ras-like protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the testis, liver, brain glioblastomas, B cell chronic lymphatic leukemia, marrow, lymph (including germinal center B cells), and leukocytes.

FIG. 2 provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 19 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the Ras guanyl nucleotide releasing protein subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the Ras guanyl nucleotide releasing protein subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the Ras guanyl nucleotide releasing protein subfamily and the expression pattern observed. Experimental data as provided in FIG. 1 indicates expression in humans in the testis, liver, brain glioblastomas, B cell chronic lymphatic leukemia, marrow, lymph (including germinal center B cells), and leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known Ras guanyl nucleotide releasing protein family or subfamily of Ras-like proteins.

Specific Embodiments

Peptide Molecules

The present invention provides nucleic acid sequences that encode protein molecules that have been identified as being members of the Ras-like protein family and are related to the Ras guanyl nucleotide releasing protein subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in humans in the testis, liver, brain glioblastomas, B cell chronic lymphatic leukemia, marrow, lymph (including germinal center B cells), and leukocytes. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-terminus of the Ras-like protein polypeptide.

In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Project*, Smith, D. W., ed., Academic Press, New York, 1993; *Computer Analysis of Sequence Data, Part 1*, Griffin, A. M., and Griffin, H. G., eds. Humana Pess, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequence is determined using the Needleman and Wunsch (*J. Mol. Biol* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM 120 weight residue table, a gap length penalty of 12 and a gap penalty of 4.

The nucleic acid and protein sequences of the present invention can further be used as a "query sequence" to perform a search against sequence databases to, for example identify other family members or related sequences. Such searches can be performed using the NBLAST and XBLAST programs (version.2.0) of Altschul, et al. (*J. Mol. Biol.* 215:403–10 (1990)). BLAST nucleotide searches can be performed with the NBLAST program, score=100, word length=12, to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein. The gene encoding the novel ras-like protein of the present invention is located on a genome component that has been mapped to human chromosome 11 (as indicated in FIG. 3), which is supported by multiple lines of evidence, such as STS and BAC map data.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. The gene encoding the novel ras-like protein of the present invention is located on a genome component that has been mapped to human chromosome 11 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the ras-like protein of the present invention. SNPs were identified at 19 different nucleotide positions. Some of these SNPs, which are located in introns and outside the ORF, may affect control/regulatory elements.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., *J. Mol. Biol.* 224:899–904 (1992); de Vos et al. *Science* 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins-Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes. A large percentage of pharmaceutical agents are being developed that modulate the activity of Ras-like proteins, particularly members of the Ras guanyl nucleotide releasing protein subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the testis, liver, brain glioblastomas, B cell chronic lymphatic leukemia, marrow, lymph (including germinal center B cells), and leukocytes. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the Ras guanyl nucleotide releasing protein subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes.

The proteins of the present invention are also useful in drug screening assays, in cell-based or cell-free systems. Cell-based systems can be native, i.e., cells that normally express the Ras-like protein, as a biopsy or expanded in cell culture. Experimental data as provided in FIG. 1 indicates expression in humans in the testis, liver, brain glioblastomas, B cell chronic lymphatic leukemia, marrow, lymph (including germinal center B cells), and leukocytes. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, Ras guanyl nucleotide releasing protein or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising Ras guanyl nucleotide releasing protein may be administered to a subject to prevent or treat a disorder associated with increased apoptosis including, but not limited to, those listed above.

In still another embodiment, an agonist which is specific for Ras guanyl nucleotide releasing protein may be administered to prevent or treat a disorder associated with increased apoptosis including, but not limited to, those listed above.

In a further embodiment, a vector capable of expressing Ras guanyl nucleotide releasing protein, or a fragment or a derivative thereof, may be used to prevent or treat a disorder associated with increased apoptosis including, but not limited to, those listed above.

In cancer, where Ras guanyl nucleotide releasing protein promotes cell proliferation, it is desirable to decrease its activity. Therefore, in one embodiment, an antagonist of Ras guanyl nucleotide releasing protein may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for Ras guanyl nucleotide releasing protein may be used directly as an antagonist, or indirectly as a targeting or delivery mechanism for bringing a phannaceutical agent to cells or tissue which express Ras guanyl nucleotide releasing protein.

In another embodiment, a vector expressing the complement of the polynucleotide encoding Ras guanyl nucleotide releasing protein may be administered to a subject to prevent or treat a cancer including, but not limited to, the types of cancer listed above.

In inflammation, where Ras guanyl nucleotide releasing protein promotes cell proliferation, it is desirable to decrease its activity. Therefore, in one embodiment, an antagonist of Ras guanyl nucleotide releasing protein may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for Ras guanyl nucleotide releasing protein may be used directly as an antagonist, or indirectly as a targeting or delivery mechanism for bringing a pharmaceutical agent to cells or tissue which express Ras guanyl nucleotide releasing protein.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries). (Hodgson, Bio/technology, 1992 Sep. 10, (9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in humans in the testis, liver, brain glioblastomas, B cell chronic lymphatic leukemia, marrow, lymph (including germinal center B cells), and leukocytes. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:12046–12054 (1993); Bartel et al., *Biotechniques* 14:920–924 (1993); Iwabuchi et al., *Oncogene* 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in humans in the testis, liver, brain glioblastomas, B cell chronic lymphatic leukemia, marrow, lymph (including germinal center B cells), and leukocytes. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the testis, liver, brain glioblastomas, B cell chronic lymphatic leukemia, marrow, lymph (including germinal center B cells), and leukocytes. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^3H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the testis, liver, brain glioblastomas, B cell chronic lymphatic leukemia, marrow, lymph (including germinal center B cells), and leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the testis, liver, brain glioblastomas, B cell chronic lymphatic leukemia, marrow, lymph (including germinal center B cells), and leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the testis, liver, brain glioblastomas, B cell chronic lymphatic leukemia, marrow, lymph (including germinal center B cells), and leukocytes. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. The gene encoding the novel ras-like protein of the present invention is located on a genome component that has been mapped to human chromosome 11 (as indicated in FIG. 3), which is supported by multiple lines of evidence, such as STS and BAC map data.

FIG. 3 provides information on SNPs that have been found in the gene encoding the ras-like protein of the present invention. SNPs were identified at 19 different nucleotide positions. Some of these SNPs, which are located in introns and outside the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2× SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 19 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel ras-like protein of the present invention is located on a genome component that has been mapped to human chromosome 11 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes.

Nucleic acid expression assays are useful for drug screening to identify compounds that modulate Ras-like protein nucleic acid expression.

The invention thus provides a method for identifying a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in humans in the testis, liver, brain glioblastomas, B cell chronic lymphatic leukemia, marrow, lymph (including germinal center B cells), and leukocytes. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as mRNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein mRNA in the presence of the candidate compound is compared to the level of expression of Ras-like protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes. Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in humans in the testis, liver, brain glioblastomas, B cell chronic lymphatic leukemia, marrow, lymph (including germinal center B cells), and leukocytes.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as mRNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the ras-like protein of the present invention. SNPs were identified at 19 different nucleotide positions. Some of these SNPs, which are located in introns and outside the ORF, may affect control/regulatory elements. The gene encoding the novel ras-like protein of the present invention is located on a genome component that has been mapped to human chromosome 11 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the ras-like protein of the present invention. SNPs were identified at 19 different nucleotide positions. Some of these SNPs, which are located in introns and outside the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the mRNA and thus block translation of mRNA into Ras-like protein.

Alternatively, a class of antisense molecules can be used to inactivate mRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that the ras-like proteins of the present invention are expressed in humans in the testis, liver, brain glioblastomas, B cell chronic lymphatic leukemia, marrow, and lymph (including germinal center B cells), as indicated by virtual northern blot analysis. In addition, PCR-based tissue screening panels indicate expression in leukocytes. For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthe-sized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the ras-like protein of the present invention. SNPs were identified at 19 different nucleotide positions. Some of these SNPs, which are located in introns and outside the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed*, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic acid molecule consisting of a nucleotide sequence selected from the group consisting of:
   (a) a transcript/cDNA sequence that encodes a protein comprising the amino acid sequence of SEQ ID NO:2;
   (b) a nucleotide sequence consisting of SEQ ID NO: 1;
   (c) a nucleotide sequence consisting of SEQ ID NO:3; and
   (d) a nucleotide sequence that is completely complementary to a nucleotide sequence of(a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of a polypeptide encoded by the nucleic acid molecule of claim 1, and recovering said polypeptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 8
<210> SEQ ID NO 1
<211> LENGTH: 2349
<212> TYPE: DNA
<213> ORGANISM: Human

<400> SEQUENCE: 1

| | | | | | |
|---|---|---|---|---|---|
| tcctccggtc | gcccgccctc | ggggcagcta | gtggcgcagc | ccccgcccg | cggccctggc | 60 |
| ctcccgggcg | gcgcggcagg | ggaggggtta | agctgccgca | gggaccgccg | cgtgcggggc | 120 |
| gagagggagc | ccccggtggg | ggtggcgcag | ccggcggggt | tcggtccgag | cccggtggga | 180 |
| ggctcccgga | gcgcagcctg | ggcccagccc | acccgcgcc | ggcggccatg | gcaggcaccc | 240 |
| tggacctgga | caagggctgc | acggtggagg | agctgctccg | cggtgcatc | gaagccttcg | 300 |
| atgactccgg | gaaggtgcgg | gacccgcagc | tggtgcgcat | attcctcatg | atgcacccct | 360 |
| ggtacatccc | ctcctctcag | ctggcggcca | agctgctcca | catctaccaa | caatcccgga | 420 |
| aggacaactc | caattccctg | caggtgaaaa | cgtgccacct | ggtcaggtac | tggatctccg | 480 |
| ccttcccagc | ggagtttgac | ttgaaccegg | agttggctga | gcagatcaag | gagctgaagg | 540 |
| ctctgctaga | ccaagaaggg | aaccgacggc | acagcagcct | aatcgacata | gacagcgtcc | 600 |
| ctacctacaa | gtggaagcgg | caggtgactc | agcggaaccc | tgtgggacag | aaaaagcgca | 660 |
| agatgtccct | gttgtttgac | cacctggagc | ccatggagct | ggcggagcat | ctcacctact | 720 |

```
tggagtatcg ctccttctgc aagatcctgt ttcaggacta tcacagtttc gtgactcatg    780
gctgcactgt ggacaacccc gtcctggagc ggttcatctc cctcttcaac agcgtctcac    840
agtgggtgca gctcatgatc ctcagcaaac ccacagcccc gcagcgggcc ctggtcatca    900
cacactttgt ccacgtggcg gagaagctgc tacagctgca gaacttcaac acgctgatgg    960
cagtggtcgg gggcctgagc cacagctcca tctcccgcct caaggagacc cacagccacg   1020
ttagccctga ccatcaagc tctgggagg gtctcacgga actagtgacg gcgacaggca   1080
actatggcaa ctaccggcgt cggctggcag cctgtgtggg cttccgcttc ccgatcctgg   1140
gtgtgcacct caaggacctg gtggccctgc agctggcact gcctgactgg ctggacccag   1200
cccggacccg gctcaacggg gccaagatga agcagctctt tagcatcctg gaggagctgg   1260
ccatggtgac cagcctgcgg ccaccagtac aggccaaccc cgacctgctg agcctgctca   1320
cggtgtctct ggatcagtat cagacggagg atgagctgta ccagctgtcc ctgcagcggg   1380
agccgcgctc caagtcctcg ccaaccagcc ccacgagttg caccccacca ccccggcccc   1440
cggtactgga ggagtggacc tcggctgcca acccaagct ggatcaggcc ctcgtggtgg   1500
agcacatcga agatggtg gagtctgtgt tccggaactt tgacgtcgat ggggatggcc   1560
acatctcaca ggaagaattc cagatcatcc gtgggaactt cccttacctc agcgcctttg   1620 ggacctcga ccagaaccag gatggctgca tcagcaggga ggagatggtt tcctatttcc   1680
tgcgctccag ctctgtgttg gggggcgca tgggcttcgt acacaacttc caggagagca   1740
actccttgcg ccccgtcgcc tgccgccact gcaaagccct gatcctgggc atctacaagc   1800
agggcctcaa atgccgagcc tgtggagtga actgccacaa gcagtgcaag gatcgcctgt   1860
cagttgagtg tcggcgcagg gcccagagtg tgagcctgga ggggtctgca ccctcaccct   1920
cacccatgca cagccaccat caccgcgcct tcagcttctc tctgcccgc cctggcaggc   1980 gaggctccag gcctccagca atccccctcc cagcagagat ccgtgaggag gaggtacaga   2040
cggtggagga tggggtgttt gacatccact tgtaatagat gctgtggttg atcaaggac   2100 tcattcctgc cttggagaaa atacttcaac cagagcaggg agcctggggg tgtcggggca   2160
ggaggctggg gatgggggtg ggatatgagg gtggcatgca gctgagggca gggccagggc   2220
tggtgtccct aaggttgtac agactcttgt gaatatttgt attttccaga tggaataaaa   2280
aggcccgtgt aattaaaaaa aaaaaaaaaa aaaaaaaaaa aaaaaaaaaa aaaaaaaaa   2340 aaaaaaaaa                                                           2349
```

<210> SEQ ID NO 2
<211> LENGTH: 615
<212> TYPE: PRT
<213> ORGANISM: Human

<400> SEQUENCE: 2

Met Ala Gly Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
                20                  25                  30

Pro Gln Leu Val Arg Ile Phe Leu Met Met His Pro Trp Tyr Ile Pro
            35                  40                  45

Ser Ser Gln Leu Ala Ala Lys Leu Leu His Ile Tyr Gln Gln Ser Arg
        50                  55                  60

Lys Asp Asn Ser Asn Ser Leu Gln Val Lys Thr Cys His Leu Val Arg
65                  70                  75                  80

-continued

```
Tyr Trp Ile Ser Ala Phe Pro Ala Glu Phe Asp Leu Asn Pro Glu Leu
                85                  90                  95

Ala Glu Gln Ile Lys Glu Leu Lys Ala Leu Leu Asp Gln Glu Gly Asn
            100                 105                 110

Arg Arg His Ser Ser Leu Ile Asp Ile Asp Ser Val Pro Thr Tyr Lys
            115                 120                 125

Trp Lys Arg Gln Val Thr Gln Arg Asn Pro Val Gly Gln Lys Lys Arg
            130                 135                 140

Lys Met Ser Leu Leu Phe Asp His Leu Glu Pro Met Glu Leu Ala Glu
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
                180                 185                 190

Leu Glu Arg Phe Ile Ser Leu Phe Asn Ser Val Ser Gln Trp Val Gln
            195                 200                 205

Leu Met Ile Leu Ser Lys Pro Thr Ala Pro Gln Arg Ala Leu Val Ile
            210                 215                 220

Thr His Phe Val His Val Ala Glu Lys Leu Leu Gln Leu Gln Asn Phe
225                 230                 235                 240

Asn Thr Leu Met Ala Val Val Gly Gly Leu Ser His Ser Ser Ile Ser
                245                 250                 255

Arg Leu Lys Glu Thr His Ser His Val Ser Pro Glu Thr Ile Lys Leu
                260                 265                 270

Trp Glu Gly Leu Thr Glu Leu Val Thr Ala Thr Gly Asn Tyr Gly Asn
            275                 280                 285

Tyr Arg Arg Arg Leu Ala Ala Cys Val Gly Phe Arg Phe Pro Ile Leu
            290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
                340                 345                 350

Pro Val Gln Ala Asn Pro Asp Leu Leu Ser Leu Leu Thr Val Ser Leu
            355                 360                 365

Asp Gln Tyr Gln Thr Glu Asp Glu Leu Tyr Gln Leu Ser Leu Gln Arg
            370                 375                 380

Glu Pro Arg Ser Lys Ser Ser Pro Thr Ser Pro Thr Ser Cys Thr Pro
385                 390                 395                 400

Pro Pro Arg Pro Pro Val Leu Glu Glu Trp Thr Ser Ala Ala Lys Pro
                405                 410                 415

Lys Leu Asp Gln Ala Leu Val Val Glu His Ile Glu Lys Met Val Glu
            420                 425                 430

Ser Val Phe Arg Asn Phe Asp Val Asp Gly Asp Gly His Ile Ser Gln
            435                 440                 445

Glu Glu Phe Gln Ile Ile Arg Gly Asn Phe Pro Tyr Leu Ser Ala Phe
450                 455                 460

Gly Asp Leu Asp Gln Asn Gln Asp Gly Cys Ile Ser Arg Glu Glu Met
465                 470                 475                 480

Val Ser Tyr Phe Leu Arg Ser Ser Val Leu Gly Gly Arg Met Gly
                485                 490                 495
```

```
Phe Val His Asn Phe Gln Glu Ser Asn Ser Leu Arg Pro Val Ala Cys
                500                 505                 510
Arg His Cys Lys Ala Leu Ile Leu Gly Ile Tyr Lys Gln Gly Leu Lys
            515                 520                 525
Cys Arg Ala Cys Gly Val Asn Cys His Lys Gln Cys Lys Asp Arg Leu
        530                 535                 540
Ser Val Glu Cys Arg Arg Ala Gln Ser Val Ser Leu Glu Gly Ser
545                 550                 555                 560
Ala Pro Ser Pro Ser Pro Met His Ser His His Arg Ala Phe Ser
                565                 570                 575
Phe Ser Leu Pro Arg Pro Gly Arg Arg Gly Ser Arg Pro Pro Ala Ile
            580                 585                 590
Pro Leu Pro Ala Glu Ile Arg Glu Glu Val Gln Thr Val Glu Asp
        595                 600                 605
Gly Val Phe Asp Ile His Leu
        610                 615

<210> SEQ ID NO 3
<211> LENGTH: 20951
<212> TYPE: DNA
<213> ORGANISM: Human

<400> SEQUENCE: 3
acagaaaggt cctgtttcta agtcttacat taccaagact gaggtgcggg ggcggtcctg      60
gatcccccgc cccaaggctg ggaggggcac gcctcggaag ggaggtttgg ggtcggtggt     120
ttcacagtga gtgtgtctga agccaaatgg tcggaaaccg ttaccgctc tcctaggccc     180
ggctagtggg gaccccaacc gcctgcggct gcccctccca agttcctccc tgttggccag     240
gcatccaggt ctccagtctc cgagctgcgg agaacccacc gccacatgcg gctgccccct     300
tccattcgac cctgtgggga gccaggcttc cggggccccg ttcctcctgt gtgaactggg     360
cccccgccc ccattcccag acatcaaggc gcgtctcca gatagccacg atttcattcc     420
tcgctcccca caggtccctc tcccaaaat attcccatct tgtcctagcc catccccag      480
actatctcaa ggaccagctg tccccacgcc cccgacctcc actaggcctg tgccacccgc     540
tgcctgcagg aagacgcccg gtcccgggcc gggttagccc catgggaacg gtttgtctcg     600
aaaacaggaa cccgagctgg gggctgggcg gggcgcccct tccccaccgc agtccgcttc     660
ctgcccctcc cggcttcctc cgcccgacac ccaggcaggg cgggggcac tgggcgtcc      720
gcggttgggg gagggctct tcgtttcggt ccccctccc gcgtcccggg cggcggggcc     780
tccggtcgcc cgcctcgggg cagctagtgg cgcagccccc cgcccgcggc cctgcctcc     840
cgggcggcgc ggcaggggag gggttaagct gccgcaggga ccgccgcgtg cggggcgaga     900
gggagccccc ggtgggggtg gcgcagccgg cggtgcggag ctccgcgcag gggcggaggg     960
gggaggggc agcctggcgc gggggcgggg gcggggcgg ggggagcggg gccgcggcgt    1020
ggagagcggg cggagccgc agccgcagcg aggccggcgg gcgggagcgc acggaggtgg    1080
ggtcggccag gccggtgcgg gctccttgcg gcaggtccca agagtgagtg ggcgagcgcg    1140
ggcggggcgc caggcgaagg agggcgcggc cccagcgac tcccccccg cccagggcgg    1200
cgcgggcggg ctggggggcgg cgagcgggtg gggagtctgc ggcccgggtc tgggagaggg    1260
ggcagcggcc acgagagcta aggcgcgctg gatccccgga gggcggagga cctccacggt    1320
gcacccagct tttcccagcc accttccagc ggggcccctcc cccgcgtacc cccatttggc    1380
agatgagaaa attgaggctc ccagaggcca agtgattctc aaggtcacac gaggaagcgg    1440
```

-continued

```
tagagccagg cggggacggc tctgggtggc tcttaggaaa agtccgcctg agaactccgt    1500
acaggagctc ccctgtcctc cagcctgggg gagtgagtat gtgtagggcc gggtaccctt    1560 tccgtgggc aaggctctgc caaaatctgg gagtgagggg agtcagggag ctggggccgc     1620
agggcgggcc ctgcaccgca aatgggaggg gggcgacgga atgggcgtgc gcacccatgg    1680
gggtgtgtgc atgtgtgtgg gagtgtacat gcgtggagag gcactgcctt gcgtgtgtgc    1740
acacgtgtga ggatgtcagc gcctgtgtgg ccgcgggact caaggctggc ctggctcaag    1800
tgaacagcac gtccaggagg cgacctcgtc cgcgggtttg cattctgggg tggacgagct    1860
gggtatgtgt gcctgagggt ttcttcgtgc aggtgtgcac agggtgtggg tgccattgtg    1920
tgtgagagac ggaggatggg gaggccggtg cctgtggccc ggtgcgtgta agtgcggacg    1980
cctgcacctc cacttaggtc cccggcctcc gacgactaac ttgggtgtgg agtgtttgcc    2040
cctgccaggt gcgtatgac cccgccagtg accggagttg ctaatggtgt catgcaccca     2100
ccggccaccc ttggcgcgag cgcccccctc tggacaccct gctccgtgcg cgctcacagt    2160
tcgcctgtgc ggggccgggg ccagggtcag gagccgggga tagggaggaa gagggcctgt    2220
ggacaagctg agccgggacc cctgggacct ttgcggaggt ggcctgggag cgctcagttc    2280
ccaggctgag gcttcccgct gacgcctcct ggccgcagcg ggctcccccc gcccaggaa    2340 tgttcctctc ccatccagtc cgcctcccct agggcaggcc cctgggggc tgccgcagcc    2400 ccgcctcgcc ttcctgggct cccggagggg gcgaggcga gcaggacgcc tgggttctct    2460 cccccacct cccataccag ggagaaattc ctccgaggtc ccctcaggct ctgggttccc     2520
aaaataaccc tgcggggaa gggaggctgt ggagggaggg aagcgggagg ggcgcagagc     2580
cgagctgcgg ggtgctgcag gtgcctctgg ggagagggcg cgaggagaag gcgccctgcg    2640 ggggctggg cgccagccag tcctgggatc ttggttcgtc cccatcctcg tgaagccct     2700 cggccttccc gcgactccga gggtgggccg gaagcctctc tgcgggtccg tttcccaact    2760
ggcgggttgc accatcccgg gccagaccgt ttaaccccgg gagtggccgc gggggacaac    2820
tccgcccctg tccagcaggg ggcgtgcccg ccccgccccg tttctgcccg cggggccgct    2880
cccccgcccg cgactccgca gactcccgct ctgcctctcc cgggacaggg gttcggtccg    2940
agcccggtgg gaggctcccg gagcgcagcc tgggcccagc ccaccccgcg ccggcggcca    3000
tggcaggcac cctggacctg gacaagggct gcacggtgga ggagctgctc cgcgggtgca    3060
tcgaagcctt cggtgagtgg ctcggagggg cacacgagc ctgagcctag ccccgagtct     3120
gagcccgggt ccctgcctcc caggcacagt ccagggcaca gccctgaccc ggacccaccc    3180
tgctccgcag cgtgcagtct cttaacgaa agcctcctcc gcaacgcagg gcagagagat     3240
gcacgccctt cagacagatg aggtttccct tctctagcct tccccagcgg cggcgaaggg    3300
agggccgggt cccggactct gacacttgag gggcattatc tgtctcccgg ggaatccgga    3360
ggaactcgct atctccggcc tggagctgt ttccggctaa tggggggcgg cttatctggt      3420
gaaggggtgc cccttccccc caagcgctca ggaaatgacc tctggattct tgaccccggg    3480
gaacccaggc tccttccgcc ccagctggtt cccctccgga cgatgggcgg ctcgggcgct    3540
cccctcctcc agtcctcagg gcgtgcctat ctctcgccca ccacccttt cctctctaat     3600 ttgcctcctg ctctcggagt cctgggcaag caggaggtgg gcggggtcga gcgtgcaccc    3660
gaaggaccga tacctggcgg gttgcggggt gaggatgagg catggtagct gcggaccag    3720 ctcagccacc tgtctttgac ccttcggagt cagatgactc cgggaaggtg cgggacccgc    3780
```

-continued

```
agctggtgcg catgttcctc atgatgcacc cctggtacat cccctcctct cagctggcgg      3840
ccaagctgct ccacatatat ccttcgccgg ccttgccaag gccccgccg tcggagccca       3900 tgcgcagccc ctctgcccag cccaggtgca gaatgagcct cgctcctaag tataggccac     3960
tccttatccc agagctcagg cgtcgtccca gcctccaact agggcctagg ctctgccccc      4020
tccttgctcc tagcgactcg gtcctgtccc caggctctgt cccagccga ggccttgccc       4080 tccttctccc tagagtctag ggcctgcccc tgcttcaggc ttgggtgcgc ccgtgcatc       4140 tctctctccc agagcccagg ctttgctttc agcctccctc agcacctagt cctccacccc      4200
cacctccaac ccctcccaga gctcaagcct caccccagc atctccgcag agcgcaagcc      4260
ccatccctag aacgtgtctc ctagaaccag gccccgcccc cagcctccct ccacgcaggc    4320 ctcccttct  agagttaagc ggcctcctta accctctcct tcacctacca acaatcccgg      4380
aaggacaact ccaattccct gcaggtgaaa acgtgccacc tggtcaggtg agtctttccc     4440
ctggggctct agcccctccc ctttctccct tctctctggc ttcaggctgg cctggaggag     4500
ggggcagggc gctgtttctg ggagtggggtt tgaaccctgg cttgtccggg tgggcagtgc    4560
tgccacaggc tcacccttc ctgggtctgg gccttaattt tcttttctgc gcagtgcggg     4620
tggttgtctc aagggtctaa tgtacacttg gagtggcgaa ggaaagagct ggaaccatag    4680
tttgagggtc tttttgctta ggtgactata atctcaaata gctccttgca gcctgctggg     4740
tgatggtggg ggaagggcta tcttgggtga ctccccgctc ctccaggtac tggatctccg    4800
ccttcccagc ggagtttgac ttgaacccgg agttggctga gcagatcaag gagctgaagg    4860
ctctgctaga ccaagaaggg aaccgacggc acagcagcct aatcgacata gacagcgtgt   4920
gcgtgggggg agcacagagg gctggggggg cactcagtat cctataccat ctgtgcttaa     4980
taaatgtctg ttgaactgaa tgagtgaggg tcatgttgct ctctcgctta aaaaccttcc     5040
atggctccct attgccttca acatgcctcc tctgggcagc ttggcgttcc tgcctcatct     5100
tccactgcca ccacccatcc cacacacctc ctcctgtagc tgcgctgggt cggctccccg    5160
tcggctgagc tctcgagtcc tttctcatca tggtgctctg ctcatatcat ccccttgct     5220 gcctcctccg tgttaccaag actcagttca ggcatgaagt ctccgtgggc tctgagggtt    5280
cggggctctt ccggggtaga atttgtcgtt cccacctctg ttttccatgg cactttgtac    5340
agactcctgt acaaagacct ctgtacatgt gtcacgctgt tttgtgatca tgtgttctg    5400 tgtctgtctc cctcagtaga ctgtgagctc ctcgagggca ggaaccgtgt cttactcatc    5460
tctgtattcc cagcgcctag cacagtgcct ggcacagagt acgttgttca taaatgtgtg    5520
ttgagtgcat gacggggtgg ggggagatga ggaggagttg ctgggactgg gaacattcgt    5580
gcctaggaca gtgcctcgca ttatgtaggt tctcagtaag cgtgaatggt gtgtctgtgt     5640
gagtgggggg ccacgaggca tgcgcatgtc cagcaaaggg ctcactaccc ctgccccccc   5700
agccctacct acaagtggaa cggcaggtg actcagcgga accctgtggg acagaaaaag     5760
cgcaagatgt ccctgttgtt tgaccactg gagcccatgg agctggcgga gcatctcacc    5820
tacttggagt atcgctcctt ctgcaagatc ctggtgcggc ccgagggctg ggggtcagg    5880 ggtccaatgt gggctggaag agagttctag gaggggcagg gtccctggcg taggctgggt     5940
cacagggtgc atcagggtt tcagtgtaac cactgaaggt cagctggagg gtgaggagtg     6000
gctatcagtg aggggagagg ccggcaaggt gctgaggcca ctcctcatgc ccccagtttc    6060
aggactatca cagtttcgtg actcatggct gcactgtgga caacccgtc ctggagcggt    6120 tcatctccct cttcaacagc gtctcacagt gggtgcagct catgatcctc agcaaaccca    6180
```

```
cagccccgca gcgggccctg gtcatcacac actttgtcca cgtggcggag gtgcctgccc    6240
ctccctcccg tgtctccca accaccccac atgccagtca ggccaaccct tcccttcccc    6300
taacccactg ccttctctct agataagctg ggccaaattc tgggcccact cagtgactcc    6360
ctgcctctcc gtccccattt gccttccaga agctgctaca gctgcagaac ttcaacacgc    6420
tgatggcagt ggtcggggc ctgagccaca gctccatctc ccgcctcaag gagacccaca    6480
gccacgttag ccctgagacc atcaaggtgc ctgggactgg ggaggggccg gtgcttcca    6540 ggtctgtctt cactgggtcc tcccagcagc actgggggct gggcacagct gtcctcattt    6600
gatagatatg gaaatggagg ctcagagggg ttaagtgctt ttctcagttt gcacaatggc    6660
aacagcagag tgggggctca caggtcgtca gggaccccaa agctagtact tttttttttt    6720
tttttaagac agggtctctc tctctgttgt ccagactgga gttcagtggt gcagtcacaa    6780
gctcactgca gccttgaatt cctgagctca atcgatcctc ccacctcagc ctcctgagta    6840
gctgggacta caggtgtacg ccaccatgcc taatttttgt attgttatta atttttttt    6900 ttttttttta gagatgggt tttgccatgt tgcccagact ggtcttgaac tcctgggctc    6960
aagtgatccg cctgccttgg cctcccaaag tgctgagatt atggcttgag ccattgtgcc    7020
ttgccacttg tagtttcttc ttttctttct ccttcatttt ttattatttt tgaagtattt    7080
tgaagtattg agtaacatac atatagaaaa gtatataaaa acatatgaga ctgggcgtag    7140
tagctcacac ctgtaatccc agcactttgg gaggctgagg tggcagatc acgtgacatc    7200 aggagtttga gaccagcctg ccaacaaggt ggaaaccca tctctactaa aatacaaaaa    7260
ttagccaggc atggtggcac gcacctggaa tccaagctac ttgggaggct gaggcaggag    7320
gagaattact tgaactcagg aggcggaggt tgcagtgagc caagattgtg ccacttcact    7380
ccagcctggg cgacagagtg agactccatc taaaaaaaaa gaaaagtata taaaaacata    7440
tgaatagttt aaagaaaaat tgtaaagaaa acactgtgta actactgccc gggttgggaa    7500
atagaacctt gccaggcccc caagcgccca gcactttaga gcataactcc ctccccacga    7560
cttttgcaat gatgatcttg ctttctttta tagcttcacc atgtaggtat gcggtccaaa    7620
acaatgtggg gctttttgtt gtctgttttg aactttctat gaatggaatg ttgtttgtgt    7680
tattttatgt cttgcttttt tcattccaca tggttctgag agtcttttca ttctgtcatg    7740
tggagcaatt gtttttttcat tttcattgcc atataatatt ttattgtacg tctaccccaa    7800
ttcatttatt tatttatttt tttgagatgg agtctgtctc tgtcatccag gctggagtgc    7860
ggtggcgaga tctcatcact gcaacttccg tctcctgggt ttacgtgatt ctcgtgcctc    7920
agcctcctga gtagctggga ttatgggctc gtaccaccac gtctggctaa ttttttgtag    7980
agacaggctt tcaccatgtt gccgaggctg gtcttgaact cctgagctca ggcaatccac    8040
ccgctttagc ctcccaaagt gctgggatta caggtgtgag ccactgcccc cagcctaccc    8100
caatttatgt attgattcta ttgttgaatg ttgggtttt cctttttctt ttctttcttt    8160 cttttttcttt ctttttttct ttttttgga gagggagtct tgctctgtcg ccaggctgga    8220
gtgcagtgac gctaatttgg ctcactgcat cactgcaccc tctgcctccc gggttcaagc    8280
gattctcctg cctcagcctc ctgagtagct gggactacag gcatgcacca ccacacccgg    8340 ctaattttg tattttttta gtagagatga ggtttccacc atgttggcca agatggtctc    8400
catctcttga cctcatgatc catctgccat ggcctcccaa agtgctgaga ttacaagtgt    8460
gagccaccac gcccagctgg ttttccagt ttttgctgtt tggacggggt ggctgagtat    8520
```

-continued

```
gttcttccag gtcattgtcc tgtgctgcct tgcctccctg agcctctgtt tctcctgtta    8580
aatgttgatg attccctgca tccaggcctg gtttagaggt gtggtgcttt tggcagtgag    8640
tattgccttg aattcatggc aatgaattca atccccaggg gctgagagag ccagtcgtgg    8700
gggacagtaa gggaggtttt tactctttca cctgtccctg accctgactc ctcctcaccc    8760
cctcctacat ttccagggct gaggtaggga ggatagttgt gggggtatga ctcctctgtc    8820
ctttgtcccc agctctggga gggtctcacg gaactagtga cggcgacagg caactatggc    8880
aactaccggc gtcggctggc agcctgtgtg ggcttccgct tcccgatcct gggtgtgcac    8940
ctcaaggacc tggtggccct gcagctggca ctgcctgact ggctggaccc agcccggacc    9000
cggctcaacg gggccaagat gaagcagctc tttagcatcc tggaggagct ggccatggtg    9060
accagcctgc ggccaccagt acaggccaac cccgacctgc tgagcctgct cacggtgagg    9120
agcagggggc agggaggtgg ggagctgggc accaggggtt gacagtttcc ccaggtcctg    9180
gctgtgggcg tggcctgggg ctctgggttc tggccaagaa actgagatct agcgtgggct    9240
ctggggtttg gagtggatgc tgagaagggg tccaggctct ggttgggct gtggactgag    9300
gtctgatctc caggctggta tgtggactgt gggcagtttg aactgggcct gggtcccggg    9360
ttgagttctg gcaatgggct gtgttctagg gctgggccaa gctctgcatt ctgtgggcag    9420
gggtggtttc taagcatggc cctgggctcg gagtgaagtt ctgggcttgg ctttacactt    9480
ggtcttgggg tctagggtgg gagttgggtt ctggtttaga ccagacaag gttctagaca    9540
ttgggctggg gcttaagtgt taaggtttgg agtggattct tagctgcttc tgggctctgg    9600
aggggatcag ggttgaaatc agagcttctg gctgggttcc gacctggctt cttccctgac    9660
atcttggcaa tatgttgtgt tcaaggtttg gggccatgct gtggtttgat ctgtgcgctg    9720
ggatgacatg ggggttgctg tgctgtgttc taagccaggc tttgtcctga gtctagcttc    9780
tgacccgagc tctggctgag ctgtggcctc taggtcgacc tttggccctg ggctctgtgg    9840
ccgtgggcag gggccagtgg gggtgatcag atctgtgtgt cccaggtgtc tctggatcag    9900
tatcagacgg aggatgagct gtaccagctg tccctgcagc gggagccgcg ctccaagtcc    9960
tcggtgaggg ggtactcccc cctctccact ctgcccttcc ctcctgagaa tcccaggatg   10020
tgaggatggg aagagctctt agcagccacc tcacccatcc atcttgtagg acagaggcat   10080
cctgggggta gggcagtagt gttgggcaga cttccctctc ccaggggttc ccctctctgt   10140
tccccgggggc tctgggctcc ccctgcctct ggccctagct caggcccgac catttccata   10200
gccaaccagc cccacgagtt gcaccccacc accccggccc ccggtactgg aggagtggac   10260
ctcggctgcc aaacccaagc tggatcaggc cctcgtggtg gagcacatcg agaagatggt   10320
ggaggtgagc tcctgcggag cctgagcagt gtgtggggag aggccagttt gccggagcac   10380
tgccctggaa ccagcacga gtgtcctgtt caagacccag cactcagccc ctaggagtca   10440
cagggcctgg caggccagct gcacggggct gaagtgcccc tgggtagggt gggggtggag   10500
gtatggaacg ggggtggtgt cagagacctc tctgagacac acctcatcaa atggactggg   10560
aacgtgggaa gggacaggac ctgatgtccc ctttactctc ccctcttctg gctctgcgtg   10620
tccctctgcg tgccccagtc tgtgttccgg aactttgacg tcgatgggga tggccacatc   10680
tcacaggaag aattccagat catccgtggg aacttcccctt acctcagcgc ctttgggac   10740
ctcgaccaga accagtgagg aggctgggg acctggggga gggaaggc aactcagccc   10800
acttctgcct gggcttcagt ttcttgtgtg caagatgagg tcactgagcc agatgatctt   10860
ggcctgggaa gctgccagtg tgggaaaggg cacttgcttt tgtggggagg agaggctgcc   10920
```

-continued

```
agctgtggag gcgcagtggt atctcacaaa ttcagacaga tgggggggctc cacctgagtc  10980
ttgcaaagac tgtgacctgg ggactgtggc tacaaaagtg ctgttttatt tgtggagctc  11040
acagctgtca agaagtgtgg gcaacttgag ctcctggata gtctgttcta atgaatagat  11100
aagaaaggtt tgtaattagc agtacccagt tgtttatcaa cagttcatat gctgacaatt  11160
tggaaaaaca gctggttctc tgaagtaggt taaacatgcc ccctgaagcc agattcatgc  11220
cctattttg ctgagcagaa aaactccat tcaaaattta aagtccatct caggtcgatt  11280
tattttttaa tgttacctgt atttcaaaaa tctgttgttt tttatttcca cattacaaaa  11340
atccacggta aaataaaatc taggtggtaa aataaattta tagtgaacaa aatgtttaaa  11400
gtaagaagtg agaggccagg tgcggtgcct cacgcctgta atcctagcac tttgggagac  11460
tgagttggca ggatcaattc aggccaggag tttgagccca gcctgggcaa cagagtaaga  11520
ccctgtctct acaaaaatta ttattattat ttttgagaca gagtctcact ctgttgccca  11580
ggctggagtg cagtggtaca atctcggctc gctgcaacct ccacttcctg ggttcaagtg  11640
attctcctgc ttcagcttcc tgagtagctg ggattacagg catgcatcac cgtgcctggc  11700
taattttgt attttagca gagatggggt tttaccatgt tggccaggct ggtctcaaac  11760
tcttgacctc aagtgatcta cctgccttgg ccccccaaag tgctaggatt acaggcatga  11820
gctactgctc ctagcctaaa aaattttttt ttgggcatgg gtggcacgtg cctgtagtcc  11880
cagctactca ggaggctgag gcaggaggaa cccttgagcc caggaggttg agactgcagt  11940
gagctgtcat cacaccactg cacttcagcc tgggtgactg cgcgagatca ccccccatcaa  12000
aaaaaaaaaa aaaagaaaaa aaaaggaaga atgaaaagtc ccctcttttcc ttttccactg  12060
gtagaagttg ccatgattaa gcactgttaa caatattaag cttggcagta tgtggattct  12120
tccagtcttc ttttcccagg caggtgcaca ttgatagaga ttttgtttgt ttggtgtctg  12180
tttcatggac aaacaggatt agagcataaa tctagttctg cttgtggctt ttatcatagc  12240
tgctttattt cttctcccag attttaggca gaggtagttg agttccatgt tttctccctg  12300
ggttggtggg tggattttta tctagaccac cttttcagtg agaatgaccc tttgagacga  12360
tggaggcctc agcttcatgc agcgggctca gccttaaccc tccacctcct gcaggccccca  12420
agctgtgtgt gtgtgtgtgt gtgtgtgtgt gtgtgtgtgt gtgtgtgtgt gttggtaagg  12480
ggaaagcccc tggttgggta tcaaaaacct agcacctggt tcggcaggag ggagaccagc  12540
accggctccc caggaccagg cccagctcac cacttcattg taaagctccc tcttttgtttc  12600
tggaacttgg gtgtttccat ttcttttctta caaaattatc tatgcattta cagcaattgt  12660
tgatatatct ttaggcagca tctaggtact tgtagtgggt tctctttttt cttttttctt  12720
tttttaatc accctctctt tttttttgaga cagagtctca ctctgtcgct caggctggag  12780
tgcaatagcg cgatcttggc tcactgcaac ctctgcctcc caggttcaag taattctcat  12840
gcctcagcct cccaagtagc tgagattaca ggcactggcc accagacccg ctaattttt  12900
ttttctttt cttttttttg agacggagtt tcgctctttg ttgcccaggc tggagtacag  12960
tggtgtgatc tcggctcact gcaacctccg cctcccgggt tcaagtgatt ctcctgtctc  13020
agcctcccga gtagctggga ttacaggcgc gcgccaccat gcctggctaa ttttttgtattt  13080
tttttttttt gagacagagt ctcactctgt cacccagact ggagtgcggt ggcgcgatct  13140
cggctcactg caagctctgc ttcccgggtt catgccattc tcctgcctca gcctccggag  13200
tagctgggac tacaagcacc caccaccgtg cccggctaat ttttttgtatt tttagtagag  13260
```

-continued

```
acggggtttc accgtggtct cgacctccag acctcgtgat ccactagcct cagcctccca   13320
aagtgctggg attacaggcg tgagccacct cacccagcct aattttgtat ttttagtaga   13380
gatgggtttt caccatgttg cgcaggctgg tattgaactt ctgacctcag gtgatccgcc   13440
cgcctcggcc tcccgaagtt ctggattat aggcgtgagc caccgcacct ggcctaattt   13500
ttgtattttt agtagagatg gagttttacc ttgttggcca ggctggtctt gaactcctga   13560
cctcacctca ggtgatctgc ccacctcggc ctcccaaagt gctgggatta caggcatgag   13620
ccactgtgca cccggcctaa aaatcaccat cttgacagaa cttcacgcct tgcttttgt    13680 ttttttttcat ctttgtgctt gttttccact taacccttga tcacagacat ctttccatgt  13740
ggattcatgt agaactacct cattcgttag aacagctgca gagtattcca ctgtgcggtt   13800
agtccatcat ttccctaacc atcctcctgc tgatggacag ttagactgtt ccagttttc    13860 agtatgattc tatgccaggc tgccatgaac gtccttttac tgatccactc aggccagtat   13920
ttctgtagga gaaattccta gaagtgggat aattggatca aagatatgc acattctaaa    13980 ttaggagaga gactgccaaa ctgacctcag acaaggttgt accagtttgc accccatca    14040 gcagcgtaca agtgcctgct tcccaacttc ctcgccaaca gggatgctat aaaaagcttc   14100
acaattttgc cagtctcatt ggcaaatggt atcttggtta aatttgcatt tctttaatac   14160
taagtggggg tagggtatct tttcatatgt ttattggcca tttatttctt ctgtcaattg   14220
cctgttctga ttccttgtcc attattctac tgggtttgtt ggtcttttc tcattgattt    14280 ttagaatctc tgttaatgga tattaaccct ttgctgttga atgtgtttgc aaatattttc   14340
tccctgtctg tcatttatgt gtcttttcc atataaattt aaaaaatttt ggtgggctca    14400
ataggtcagt ctttcccttc cgggcttctg ggatttgtgt tcggggtaga aaggccctca   14460
gcccctcaag attataaaat tataaaacct ttctttttt tttttttttt ctgagacagg    14520
gtgtcttgcc atgtcaccca ggctggagtg cagtggcatg atcttggctc gctgcaacct   14580
ccacctccca ggttcaagtg attctcgtgc cttagcctcc cgagtagctg ggattatagg   14640
tgcctgccac tatgcctggc taattttttg tattttagt agagacgggg ctttgccatg    14700
ttggccaggc tggtcttgaa ctcctgacct cgtgatccac ccgccttggc ctcccaaagt   14760
gctgggacta caggcgtaag ccactgtgct cggccctata ttttttttcag atagccagtt   14820 atcctaatgc tcccttgatt tgatggacca cctggatcac acattatgag cccctcata    14880 agcaggtggg agtctcaagc gagggccagt cccgatggga atagcacttg gtggctgagg   14940
accctcctat ctgtgcagac actgttgtaa aacttcacat gcatcatcta atttagtcct   15000
caccaaaatc ctatgaaatg taggaatgat cattacaccc attatatagat aaggaaacgg   15060 agggacaggg agattactcc gctacaggtc aagaggcagg gaagtagagc tgcgatttga   15120
actgaggtct gtgtctagaa cacgtgctca ttctttccct aaaatgtatt cataggtgaa   15180
aaagggcttc tgcggaaagc cctgggttat gtgggaaacc ctggatttac agctgtcttt   15240
ccagcaggat gatgcaggag agagagggat gcgatttctc ccaatctctc ctggtcccag   15300
aactcattag agagttctcc ctgctgaggg ctcccgactg gtgttgcaca cagtacactt   15360
cgggagcccg aggctgatgg ttccatggaa agtacacagt cattttagtt tgcacaccaa   15420
gtgtgaagtg ggcaggacag gccactgttc tgagaaggaa cccagggaaa gggactggcc   15480
caagaccaca cactgttag cggcacttcc cacatctgcc tgaccctag tccagtgccg     15540 ccttttcttt actctgcaac aggagtccaa aatcaggagt tccatgagga cactgggaac   15600
agtgggatgg gttaggccag cggtggatgg ttctggggag ggcccgagct gaagcgcccc   15660
```

```
cgcaactccc cacagggatg gctgcatcag cagggaggag atggtttcct atttcctgcg   15720
ctccagctct gtgttggggg ggcgcatggg cttcgtacac aacttccagg agagcaactc   15780
cttgcgcccc gtcgcctgcc gccactgcaa agccctggtg agagtccctt tcccggctca   15840
cggcccaagc cacgcccctc cagccccggc cccgccctcc cttctggccc cgcctctgcc   15900
agagcccttc tcaagccagg aaaacctggt aattctattt gcctctcctc ctgtggttct   15960
gcccggggcc ctgaggcggg ctctaaagcc ctagtctcac cctcaagaag gaagaagtag   16020
agtcatcacc tctaaatccc tcctcccacc acggcccctc ctctattgca gatcctgggc   16080
atctacaagc agggcctcaa atgccgaggt gagatggaat gactggaagg gctgctgggc   16140 agtgttttt ttgtttgttt gtttgtttgg gagagttact attttggtgg ggcaattgcc   16200
aaggagtgaa gtaccttaaa atcagaggcg catggccggg catggtggct caagcctgta   16260
atcccagcac tttgggaggc cgaggcgcgc agatcacctg aggtcaggag ttcaagacca   16320
gcctgaccaa catagcgcaa ccccgcctct actaaaaata caaaaagtag ctgggcgtgg   16380
tggcacccac ctgtaatccc agctacttgg gaggctgagg catgagaatc gcttgaacct   16440
gggaggcggg gtttgcagtg agccgagatc acgccactgc actccagcct gggcaacaga   16500
gagggctctg tctcaaaaaa aaaaaacaac aaaaaaaccc ccaaaaccaa accccacaa    16560 aatcagaggc tcaagatgac tgatgtgaag ggagtggcgt ttaagaggcc atttattttg   16620
atgacgcagc tgcccaggaa cagagaacat gggagaaggc atagactgac aattaggagg   16680
aggagaacac tttggaagga gactcttatt ttggtggggc agctgctcag gaacaaaggt   16740
tcctggtagg ggggcgcaag cctgcgggat gggatggagg gtattctgac caatgtccct   16800
ggctggctct ccatttgctc tcccccagcc tgtggagtga actgccacaa gcagtgcaag   16860
gatcgcctgt cagttgagtg tcggcgcagg gcccagagtg tgagcctgga ggggtctgca   16920
ccctcaccct cacccatgca cagccaccat caccgcgcct tcagcttctc tctgccccgc   16980
cctggcaggc gaggctccag gcctccaggt aagaggagt cattctgtac tggcctgtgg    17040
agggaaggat gcagggctac tggggcaaag aacgcaggat ggaagccatt ccaaagtgca   17100
taattctctt tttgtggtgg gataataaag aagggacagg ccgggcgcgg tggctcacgc   17160
ctgtaatccc agcactttgg gaggccgagg cgggcggatc acgaggtcag gagatcgaga   17220
ccatcctggc taacacggtg aaaccccatc tttactaaaa atacaaaaaa aaaaaattag   17280
ccaggcgtgg tggcggacgc ctgtagtccc agctacttgg gaggctgagg caggagaatg   17340
gcatgaaccc gggaggcggg gcttgcagtg agccgagatc gcgccactgc actccagcct   17400
gggcgataga gcaagactcc gtctcagaaa aaaaaaaat aaaaaataaa gaaggacag    17460 gtaagggtgc cagaaagtgg ccaggaagcc ctggaccttc tgaggctgag gagagagacc   17520
ctaatttata aagaggtata aaagtgaaag aggcttcaag attccagtta cagtcttatt   17580
ttgttggagg ggttaacaaa ggattggaga aggtgttata tgagccattg gcttgccttt   17640
cccttcctgg ctgctctgga ggctcttctg gggaaagtcc cttgccctga taatgtcctg   17700
gcagctctct tggggtattt gatggtttta ggtcagtttg ctgaatgaca actggccaaa   17760
tgattatttt gctgagaaca gtccgaacaa ctatgttaaa ctgggtctca aggtagttga   17820
tcacaactgt ttgggttggc ataagtcctc aaaaaacaga ggcaggcaca gggcatacat   17880
cctcaaaaat agaaaagata aatccatttg cattgagcct tccagaagtg ctggggtcta   17940
aaatgtgaaa tacacacaaa attgacattt aagcaaactg cgctgacaaa tctgtggctg   18000
```

```
aaaaagctgt ggcaaaacaa aaacatagaa aaagagcctc aaaaattggg ctgaggccag   18060
gcatggtggc tcacgcctgt aatcctagca ctttgggaag ccaaggtggg tggatcaccc   18120
gaggtcagga gttggagacc agactggcca acgtggcaaa acatcatctc tacaatacaa   18180
aaatacaaaa attagctggg cgtggtggca ggcgcctgta atcccagcta cttgggaggc   18240
tgaggcacga gaatcgcttg aacctgggag gtggaggttg cagagagccg agattgcgcc   18300
attgcactcc agcctgggcg acagagagag actctgtctc aaaaaaaaaa aaaaaaaaa    18360 aaattgggct gtgaggtcat gcagggaatt gattttggt gggtgggtct gcttctggga    18420
tgatgtggat gcctcccgtg gagaggggaa gggttgatga agtcccaggg acctggaagt   18480
gtgttctgca gcaatccccc tcccagcaga gatccgtgag gaggaggtac agacggtgga   18540
ggatggggtg tttgacatcc acttgtaata gatggtgagt cctcccacag ctggcaccag   18600
agctccccac tgagggctgg ggggagctg ggagtatca gggaaatggg tgctttatcc     18660
aaatggctcc aagccaggtg ggctactacc ttgttgttag gggggtgtct tcctcacaac   18720 ctgttttct cttcccagct gtggttggat caaggactca ttcctgcctt ggagaaaata    18780
cttcaaccag agcaggagc ctgggggtgt cggggcagga ggctggggat gggggtggga    18840 tatgaggggtg gcatgcagct gagggcaggg ccagggctgg tgtccctaag gttgtacaga  18900
ctcttgtgaa tatttgtatt ttccagatgg aataaaaagg cccgtgtaat taaccttcac   18960
catcagcgcc tagaatcccg gggggtaggg ggatggtata cttttacagga tgacaatctt  19020 gggagctaga actttgtagc cagagaaact tgggaggtct ggaatctcat gtgtctggag   19080
tcttggggaa gagaatctta gaagcagaaa accttggaac ataagaatct tggggagggt   19140
ctaggatctt gaggagacca gatccttgga catctaaaac ttgaaactag taggtctgca   19200
cccgagaatt gcagggccag tcatgcatac ccaaagcctt cagcccatgg ccgaaattcc   19260
cttgctggac aggggccttt tcagccctg cttggacgct tccagtaaca gggccctcac    19320
tgcaggaatc gtgggaggga gaggggcagc acagagttgc tggctgtcgg ggaagggagg   19380
gagggccctg ggcagtccga gggccctgct gggcttgtgc ctcagggtgg gggctgcact   19440
cctccgcctt gcagcctcct ggcctggtgc tgctgccagc cggaaggaca gtgacttcca   19500
gaggaaatgc atattgatcc tgctttcagc ctccggtggt ggcttctccc aacccagctc   19560
ttccctcctg agcctgcagc acggaggttt tgggggtcac tgctacctaa agaaggctaa   19620
ggccacttct gaggctggtc tgggagttta ctaaaggttc tgaagctggg ccgggctgcc   19680
cctgggatca ggagactcca gacagcagtc ctgacaatgg gaactacctc tcagtccccc  19740
caaactggga ggtgtcccac agcagctgta ggattgtcct aggggtggag acctgagcac   19800
cttccactcc aaagcacagt atctgtgggc ctggcagtgg cctcagttcc cccatgagtg   19860
ccccggtccc ccaccccagg gttccccac atcacatcca tccctgcttt gagaccccac    19920
tccccctggc ctgttcttta ttttgggtca ctcccttctc tttcctggtc atatctctcc   19980
tgcaggccta ccctgtgttg gcccccag ccctgtctct gcatcgggtg ccccctgcc     20040 cctccttctg tcctcagccc cctccgccct tcccctctt gaggctgtaa tatccgtttc    20100
acgatttggg ggctgagttg ctataacaac agacggcgat tgtgttgtga agagcagctc   20160
gctcctgtgc cgcctgcctc ctgtgctgcc tccatccctg cagcccagtc ggttcctctt   20220
ggctcctctc gtcactaccc tccagttcca gtctggcctc ttcctggtgt gtgtgtgtgt   20280
gtgtgtgtgt gtgtgtgtat gcatgcatgc atatgtgtgt ccaggtctgc ctgcccggga   20340
tgtgacaagt agcggtcttc atggttgcat gtgtctgaat ttggtgtctg agcttcacat   20400
```

-continued

```
tgtatgcgcc tgtgtgcatg tgtgtgcatg gacatgcatg ctgtatctgc tgtgtttccc    20460
ctcccccatg tgtccccact ggcctttgca catgggagaa gggcatgtgc tcagcatatc    20520
actcaactgt ccacattggg tgggtacctg tgtgtggtgt gtgtgtgtgg gggtgtgtc     20580 ttgaagtggc aggtcccaaa tgcttaggca atctgaacct tggaccttgc agagaggaga    20640
gatgtccctg taggtgggag ggacagggag atgcagcagc tgcccggtga ccttttctgc    20700
ccttgatggg caaagctggg ggtagggaaa ggagacaagt gctcatactt acctccctcc    20760
ctgcccaggc tcctctgtaa gggtctgagt ctgtctctgt gagccattgc atctgtctgt    20820
ctatgccctg atgcctggat ggacaagggg tgtgtgtgtg tgtgtgtgtg tgtgtgtgtg    20880
agtgtgaggc tgcaggaaga ggaacagtgg gggatgggca ggaaagtggg ctgtggggtc    20940
agggaggcga t                                                         20951
```

<210> SEQ ID NO 4
<211> LENGTH: 609
<212> TYPE: PRT
<213> ORGANISM: Human

<400> SEQUENCE: 4

```
Met Ala Gly Thr Leu Asp Leu Asp Lys Gly Cys Thr Val Glu Glu Leu
  1               5                  10                  15

Leu Arg Gly Cys Ile Glu Ala Phe Asp Asp Ser Gly Lys Val Arg Asp
                 20                  25                  30

Pro Gln Leu Val Arg Met Phe Leu Met Met His Pro Trp Tyr Ile Pro
             35                  40                  45

Ser Ser Gln Leu Ala Ala Lys Leu Leu His Ile Tyr Gln Gln Ser Arg
         50                  55                  60

Lys Asp Asn Ser Asn Ser Leu Gln Val Lys Thr Cys His Leu Val Arg
 65                  70                  75                  80

Tyr Trp Ile Ser Ala Phe Pro Ala Glu Phe Asp Leu Asn Pro Glu Leu
                 85                  90                  95

Ala Glu Gln Ile Lys Glu Leu Lys Ala Leu Leu Asp Gln Glu Gly Asn
                100                 105                 110

Arg Arg His Ser Ser Leu Ile Asp Ile Asp Ser Val Pro Thr Tyr Lys
            115                 120                 125

Trp Lys Arg Gln Val Thr Gln Arg Asn Pro Val Gly Gln Lys Lys Arg
        130                 135                 140

Lys Met Ser Leu Leu Phe Asp His Leu Glu Pro Met Glu Leu Ala Glu
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
        195                 200                 205

Leu Met Ile Leu Ser Lys Pro Thr Ala Pro Gln Arg Ala Leu Val Ile
    210                 215                 220

Thr His Phe Val His Val Ala Glu Lys Leu Leu Gln Leu Gln Asn Phe
225                 230                 235                 240

Asn Thr Leu Met Ala Val Val Gly Gly Leu Ser His Ser Ser Ile Ser
                245                 250                 255

Arg Leu Lys Glu Thr His Ser His Val Ser Pro Glu Thr Ile Lys Leu
            260                 265                 270
```

Trp Glu Gly Leu Thr Glu Leu Val Thr Ala Thr Gly Asn Tyr Gly Asn
           275                 280                 285

Tyr Arg Arg Arg Leu Ala Ala Cys Val Gly Phe Arg Phe Pro Ile Leu
        290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Thr Val Ser Leu
        355                 360                 365

Asp Gln Tyr Gln Thr Glu Asp Glu Leu Tyr Gln Leu Ser Leu Gln Arg
370                 375                 380

Glu Pro Arg Ser Lys Ser Ser Pro Thr Ser Pro Thr Ser Cys Thr Pro
385                 390                 395                 400

Pro Pro Arg Pro Pro Val Leu Glu Glu Trp Thr Ser Ala Ala Lys Pro
                405                 410                 415

Lys Leu Asp Gln Ala Leu Val Val Glu His Ile Glu Lys Met Val Glu
            420                 425                 430

Ser Val Phe Arg Asn Phe Asp Val Asp Gly Asp Gly His Ile Ser Gln
        435                 440                 445

Glu Glu Phe Gln Ile Ile Arg Gly Asn Phe Pro Tyr Leu Ser Ala Phe
    450                 455                 460

Gly Asp Leu Asp Gln Asn Gln Asp Gly Cys Ile Ser Arg Glu Glu Met
465                 470                 475                 480

Val Ser Tyr Phe Leu Arg Ser Ser Val Leu Gly Gly Arg Met Gly
                485                 490                 495

Phe Val His Asn Phe Gln Glu Ser Asn Ser Leu Arg Pro Val Ala Cys
            500                 505                 510

Arg His Cys Lys Ala Leu Ile Leu Gly Ile Tyr Lys Gln Gly Leu Lys
        515                 520                 525

Cys Arg Ala Cys Gly Val Asn Cys His Lys Gln Cys Lys Asp Arg Leu
530                 535                 540

Ser Val Glu Cys Arg Arg Ala Gln Ser Val Ser Leu Glu Gly Ser
545                 550                 555                 560

Ala Pro Ser Pro Ser Pro Met His Ser His His Arg Ala Phe Ser
                565                 570                 575

Phe Ser Leu Pro Arg Pro Gly Arg Arg Gly Ser Arg Pro Pro Glu Ile
            580                 585                 590

Arg Glu Glu Glu Val Gln Thr Val Glu Asp Gly Val Phe Asp Ile His
        595                 600                 605

Leu

<210> SEQ ID NO 5
<211> LENGTH: 664
<212> TYPE: PRT
<213> ORGANISM: Human

<400> SEQUENCE: 5

Gly Arg Gly Thr Gln Gly Trp Pro Gly Ser Ser Glu Gln His Val Gln
1               5                   10                  15

Glu Ala Thr Ser Ser Ala Gly Leu His Ser Gly Val Asp Glu Leu Gly
            20                  25                  30

-continued

```
Val Arg Ser Glu Pro Gly Gly Arg Leu Pro Glu Arg Ser Leu Gly Pro
         35                  40                  45

Ala His Pro Ala Pro Ala Ala Met Ala Gly Thr Leu Asp Leu Asp Lys
 50                  55                  60

Gly Cys Thr Val Glu Glu Leu Leu Arg Gly Cys Ile Glu Ala Phe Asp
 65                  70                  75                  80

Asp Ser Gly Lys Val Arg Asp Pro Gln Leu Val Arg Met Phe Leu Met
             85                  90                  95

Met His Pro Trp Tyr Ile Pro Ser Ser Gln Leu Ala Ala Lys Leu Leu
            100                 105                 110

His Ile Tyr Gln Gln Ser Arg Lys Asp Asn Ser Asn Ser Leu Gln Val
            115                 120                 125

Lys Thr Cys His Leu Val Arg Tyr Trp Ile Ser Ala Phe Pro Ala Glu
        130                 135                 140

Phe Asp Leu Asn Pro Glu Leu Ala Glu Gln Ile Lys Glu Leu Lys Ala
145                 150                 155                 160

Leu Leu Asp Gln Glu Gly Asn Arg Arg His Ser Ser Leu Ile Asp Ile
                165                 170                 175

Asp Ser Val Pro Thr Tyr Lys Trp Lys Arg Gln Val Thr Gln Arg Asn
            180                 185                 190

Pro Val Gly Gln Lys Lys Arg Lys Met Ser Leu Leu Phe Asp His Leu
        195                 200                 205

Glu Pro Met Glu Leu Ala Glu His Leu Thr Tyr Leu Glu Tyr Arg Ser
210                 215                 220

Phe Cys Lys Ile Leu Phe Gln Asp Tyr His Ser Phe Val Thr His Gly
225                 230                 235                 240

Cys Thr Val Asp Asn Pro Val Leu Glu Arg Phe Ile Ser Leu Phe Asn
                245                 250                 255

Ser Val Ser Gln Trp Val Gln Leu Met Ile Leu Ser Lys Pro Thr Ala
            260                 265                 270

Pro Gln Arg Ala Leu Val Ile Thr His Phe Val His Val Ala Glu Lys
        275                 280                 285

Leu Leu Gln Leu Gln Asn Phe Asn Thr Leu Met Ala Val Val Gly Gly
290                 295                 300

Leu Ser His Ser Ser Ile Ser Arg Leu Lys Glu Thr His Ser His Val
305                 310                 315                 320

Ser Pro Glu Thr Ile Lys Leu Trp Glu Gly Leu Thr Glu Leu Val Thr
                325                 330                 335

Ala Thr Gly Asn Tyr Gly Asn Tyr Arg Arg Arg Leu Ala Ala Cys Val
            340                 345                 350

Gly Phe Arg Phe Pro Ile Leu Gly Val His Leu Lys Asp Leu Val Ala
        355                 360                 365

Leu Gln Leu Ala Leu Pro Asp Trp Leu Asp Pro Ala Arg Thr Arg Leu
370                 375                 380

Asn Gly Ala Lys Met Lys Gln Leu Phe Ser Ile Leu Glu Glu Leu Ala
385                 390                 395                 400

Met Val Thr Ser Leu Arg Pro Pro Val Gln Ala Asn Pro Asp Leu Leu
                405                 410                 415

Ser Leu Leu Thr Val Ser Leu Asp Gln Tyr Gln Thr Glu Asp Glu Leu
            420                 425                 430

Tyr Gln Leu Ser Leu Gln Arg Glu Pro Arg Ser Lys Ser Ser Pro Thr
        435                 440                 445
```

-continued

```
Ser Pro Thr Ser Cys Thr Pro Pro Arg Pro Pro Val Leu Glu Glu
            450                 455                 460

Trp Thr Ser Ala Ala Lys Pro Lys Leu Asp Gln Ala Leu Val Val Glu
465                 470                 475                 480

His Ile Glu Lys Met Val Glu Ser Val Phe Arg Asn Phe Asp Val Asp
                485                 490                 495

Gly Asp Gly His Ile Ser Gln Glu Glu Phe Gln Ile Ile Arg Gly Asn
            500                 505                 510

Phe Pro Tyr Leu Ser Ala Phe Gly Asp Leu Asp Gln Asn Gln Asp Gly
            515                 520                 525

Cys Ile Ser Arg Glu Glu Met Val Ser Tyr Phe Leu Arg Ser Ser Ser
            530                 535                 540

Val Leu Gly Gly Arg Met Gly Phe Val His Asn Phe Gln Glu Ser Asn
545                 550                 555                 560

Ser Leu Arg Pro Val Ala Cys Arg His Cys Lys Ala Leu Ile Leu Gly
                565                 570                 575

Ile Tyr Lys Gln Gly Leu Lys Cys Arg Ala Cys Gly Val Asn Cys His
            580                 585                 590

Lys Gln Cys Lys Asp Arg Leu Ser Val Glu Cys Arg Arg Arg Ala Gln
            595                 600                 605

Ser Val Ser Leu Glu Gly Ser Ala Pro Ser Pro Ser Pro Met His Ser
            610                 615                 620

His His His Arg Ala Phe Ser Phe Ser Leu Pro Arg Pro Gly Arg Arg
625                 630                 635                 640

Gly Ser Arg Pro Pro Glu Ile Arg Glu Glu Val Gln Thr Val Glu
                645                 650                 655

Asp Gly Val Phe Asp Ile His Leu
            660

<210> SEQ ID NO 6
<211> LENGTH: 608
<212> TYPE: PRT
<213> ORGANISM: Mus musculus

<400> SEQUENCE: 6

Met Ala Ser Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
                20                  25                  30

Pro Gln Leu Val Arg Met Phe Leu Met Met His Pro Trp Tyr Ile Pro
            35                  40                  45

Ser Ser Gln Leu Ala Ser Lys Leu Leu His Phe Tyr Gln Gln Ser Arg
        50                  55                  60

Lys Asp Asn Ser Asn Ser Leu Gln Val Lys Thr Cys His Leu Val Arg
65                  70                  75                  80

Tyr Trp Val Ser Ala Phe Pro Ala Glu Phe Asp Leu Asn Pro Glu Leu
                85                  90                  95

Ala Glu Pro Ile Lys Glu Leu Lys Ala Leu Leu Asp Gln Glu Gly Asn
            100                 105                 110

Arg Arg His Ser Ser Leu Ile Asp Ile Glu Ser Val Pro Thr Tyr Lys
        115                 120                 125

Trp Lys Arg Gln Val Thr Gln Arg Asn Pro Val Glu Gln Lys Lys Arg
    130                 135                 140

Lys Met Ser Leu Leu Phe Asp His Leu Glu Pro Met Glu Leu Ala Glu
145                 150                 155                 160
```

```
His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
        195                 200                 205

Leu Met Ile Leu Ser Lys Pro Thr Ala Thr Gln Arg Ala Leu Val Ile
    210                 215                 220

Thr His Phe Val His Val Ala Glu Lys Leu Leu Gln Leu Gln Asn Phe
225                 230                 235                 240

Asn Thr Leu Met Ala Val Val Gly Gly Leu Ser His Ser Ser Ile Ser
                245                 250                 255

Arg Leu Lys Glu Thr His Ser His Val Ser Pro Asp Thr Ile Lys Leu
            260                 265                 270

Trp Glu Gly Leu Thr Glu Leu Val Thr Ala Thr Gly Asn Tyr Ser Asn
        275                 280                 285

Tyr Arg Arg Arg Leu Ala Ala Cys Val Gly Phe Arg Phe Pro Ile Leu
    290                 295                 300

Gly Val His Leu Lys Asp Leu Val Ala Leu Gln Leu Ala Leu Pro Asp
305                 310                 315                 320

Trp Leu Asp Pro Gly Arg Thr Arg Leu Asn Gly Ala Lys Met Arg Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Thr Val Ser Leu
        355                 360                 365

Asp Gln Tyr Gln Thr Glu Asp Glu Leu Tyr Gln Leu Ser Leu Gln Arg
    370                 375                 380

Glu Pro Arg Ser Lys Ser Ser Pro Thr Ser Pro Thr Ser Cys Thr Pro
385                 390                 395                 400

Pro Pro Arg Pro Pro Val Leu Glu Glu Trp Thr Ser Val Ala Lys Pro
                405                 410                 415

Lys Leu Asp Gln Ala Leu Val Ala Glu His Ile Glu Lys Met Val Glu
            420                 425                 430

Ser Val Phe Arg Asn Phe Asp Val Asp Gly Asp Gly His Ile Ser Gln
        435                 440                 445

Glu Glu Phe Gln Ile Ile Arg Gly Asn Phe Pro Tyr Leu Ser Ala Phe
    450                 455                 460

Gly Asp Leu Asp Gln Asn Gln Asp Gly Cys Ile Ser Arg Glu Glu Met
465                 470                 475                 480

Ile Ser Tyr Phe Leu Arg Ser Ser Val Leu Gly Gly Arg Met Gly Gly
                485                 490                 495

Phe Val His Asn Phe Gln Glu Ser Asn Ser Leu Arg Pro Val Ala Cys
            500                 505                 510

Arg His Cys Lys Ala Leu Ile Leu Gly Ile Tyr Lys Gln Gly Leu Lys
        515                 520                 525

Cys Arg Ala Cys Gly Val Asn Cys His Lys Gln Cys Lys Asp Arg Leu
    530                 535                 540

Ser Val Glu Cys Arg Arg Arg Ala Gln Ser Val Ser Leu Glu Gly Ser
545                 550                 555                 560

Ala Pro Ser Pro Ser Pro Thr His Thr His His Arg Ala Phe Ser Phe
                565                 570                 575
```

```
Ser Leu Pro Arg Pro Gly Arg Arg Ser Arg Pro Pro Glu Ile Arg
        580                 585                 590

Glu Glu Glu Val Gln Thr Val Glu Asp Gly Val Phe Asp Ile His Leu
            595                 600                 605
```

<210> SEQ ID NO 7
<211> LENGTH: 591
<212> TYPE: PRT
<213> ORGANISM: Human

<400> SEQUENCE: 7

```
Gly Ser Ser Gly Leu Gly Lys Ala Ala Thr Leu Asp Glu Leu Leu Cys
 1               5                  10                  15

Thr Cys Ile Glu Met Phe Asp Asp Asn Gly Glu Leu Asp Asn Ser Tyr
             20                  25                  30

Leu Pro Arg Ile Val Leu Leu Met His Arg Trp Tyr Leu Ser Ser Thr
         35                  40                  45

Glu Leu Ala Glu Lys Leu Leu Cys Met Tyr Arg Asn Ala Thr Gly Glu
     50                  55                  60

Ser Cys Asn Glu Phe Arg Leu Lys Ile Cys Tyr Phe Met Arg Tyr Trp
 65                  70                  75                  80

Ile Leu Lys Phe Pro Ala Glu Phe Asn Leu Asp Leu Gly Leu Ile Arg
                 85                  90                  95

Met Thr Glu Glu Phe Arg Glu Val Ala Ser Gln Leu Gly Tyr Glu Lys
            100                 105                 110

His Val Ser Leu Ile Asp Ile Ser Ile Pro Ser Tyr Asp Trp Met
        115                 120                 125

Arg Arg Val Thr Gln Arg Lys Lys Val Ser Lys Gly Lys Ala Cys
    130                 135                 140

Leu Leu Phe Asp His Leu Glu Pro Ile Glu Leu Ala Glu His Leu Thr
145                 150                 155                 160

Phe Leu Glu His Lys Ser Phe Arg Arg Ile Ser Phe Thr Asp Tyr Gln
                165                 170                 175

Ser Tyr Val Ile His Gly Cys Leu Glu Asn Asn Pro Thr Leu Glu Arg
            180                 185                 190

Ser Ile Ala Leu Phe Asn Gly Ile Ser Lys Trp Val Gln Leu Met Val
        195                 200                 205

Leu Ser Lys Pro Thr Pro Gln Gln Arg Ala Glu Val Ile Thr Lys Phe
    210                 215                 220

Ile Asn Val Ala Lys Lys Leu Leu Gln Leu Lys Asn Phe Asn Thr Leu
225                 230                 235                 240

Met Ala Val Val Gly Gly Leu Ser His Ser Ser Ile Ser Arg Leu Lys
                245                 250                 255

Glu Thr His Ser His Leu Ser Ser Glu Val Thr Lys Asn Trp Asn Glu
            260                 265                 270

Met Thr Glu Leu Val Ser Ser Asn Gly Asn Tyr Cys Asn Tyr Arg Lys
        275                 280                 285

Ala Phe Ala Asp Cys Asp Gly Phe Lys Ile Pro Ile Leu Gly Val His
    290                 295                 300

Leu Lys Asp Leu Ile Ala Val His Val Ile Phe Pro Asp Trp Thr Glu
305                 310                 315                 320

Glu Asn Lys Val Asn Ile Val Lys Met His Gln Leu Ser Val Thr Leu
                325                 330                 335

Ser Glu Leu Val Ser Leu Gln Asn Ala Ser His His Leu Glu Pro Asn
            340                 345                 350
```

```
Met Asp Leu Ile Asn Leu Leu Thr Leu Ser Leu Asp Leu Tyr His Thr
            355                 360                 365

Glu Asp Asp Ile Tyr Lys Leu Ser Leu Val Leu Glu Pro Arg Asn Ser
        370                 375                 380

Lys Ser Pro Thr Ser Pro Thr Pro Asn Lys Pro Val Val Pro Leu
385                 390                 395                 400

Glu Trp Ala Leu Gly Val Met Pro Lys Pro Asp Pro Thr Val Ile Asn
                405                 410                 415

Lys His Ile Arg Lys Leu Val Glu Ser Val Phe Arg Asn Tyr Asp His
            420                 425                 430

Asp His Asp Gly Tyr Ile Ser Gln Glu Asp Phe Glu Ser Ile Ala Ala
        435                 440                 445

Asn Phe Pro Phe Leu Asp Ser Phe Cys Val Leu Asp Lys Asp Gln Asp
    450                 455                 460

Gly Leu Ile Ser Lys Asp Glu Met Met Ala Tyr Phe Leu Arg Ala Lys
465                 470                 475                 480

Ser Gln Leu His Cys Lys Met Gly Pro Gly Phe Ile His Asn Phe Gln
                485                 490                 495

Glu Met Thr Tyr Leu Lys Pro Thr Phe Cys Glu His Cys Ala Gly Phe
            500                 505                 510

Leu Trp Gly Ile Ile Lys Gln Gly Tyr Lys Cys Lys Asp Cys Gly Ala
        515                 520                 525

Asn Cys His Lys Gln Cys Lys Asp Leu Leu Val Leu Ala Cys Arg Arg
    530                 535                 540

Phe Ala Arg Ala Pro Ser Leu Ser Ser Gly His Gly Ser Leu Pro Gly
545                 550                 555                 560

Ser Pro Ser Leu Pro Pro Ala Gln Asp Glu Val Phe Glu Phe Pro Gly
                565                 570                 575

Val Thr Ala Gly His Arg Asp Leu Asp Ser Arg Ala Ile Thr Leu
            580                 585                 590

<210> SEQ ID NO 8
<211> LENGTH: 581
<212> TYPE: PRT
<213> ORGANISM: Rattus norvegicus

<400> SEQUENCE: 8

Gly Ser Arg Ala Gly Pro Lys Gly Arg Leu Glu Ala Lys Ser Thr Asn
1               5                   10                  15

Ser Pro Leu Pro Ala Gln Pro Ser Leu Ala Gln Ile Thr Gln Phe Arg
            20                  25                  30

Met Met Val Ser Leu Gly His Leu Ala Lys Gly Ala Ser Leu Asp Asp
        35                  40                  45

Leu Ile Asp Ser Cys Ile Gln Ser Phe Asp Ala Asp Gly Asn Leu Cys
    50                  55                  60

Arg Ser Asn Gln Leu Leu Gln Val Met Leu Thr Met His Arg Ile Ile
65                  70                  75                  80

Ile Ser Ser Ala Glu Leu Leu Gln Lys Leu Met Asn Leu Tyr Lys Asp
                85                  90                  95

Ala Leu Glu Lys Asn Ser Pro Gly Ile Cys Leu Lys Ile Cys Tyr Phe
            100                 105                 110

Val Arg Tyr Trp Ile Thr Glu Phe Trp Ile Met Phe Lys Met Asp Ala
        115                 120                 125

Ser Leu Thr Ser Thr Met Glu Glu Phe Gln Asp Leu Val Lys Ala Asn
```

-continued

```
            130                 135                 140
Gly Glu Glu Ser His Cys His Leu Ile Asp Thr Thr Gln Ile Asn Ser
145                 150                 155                 160
Arg Asp Trp Ser Arg Lys Leu Thr Gln Arg Ile Lys Ser Asn Thr Ser
                165                 170                 175
Lys Lys Arg Lys Val Ser Leu Leu Phe Asp His Leu Glu Pro Glu Glu
                180                 185                 190
Leu Ser Glu His Leu Thr Tyr Leu Glu Phe Lys Ser Phe Arg Arg Ile
                195                 200                 205
Ser Phe Ser Asp Tyr Gln Asn Tyr Leu Val Asn Ser Cys Val Lys Glu
        210                 215                 220
Asn Pro Thr Met Glu Arg Ser Ile Ala Leu Cys Asn Gly Ile Ser Gln
225                 230                 235                 240
Trp Val Gln Leu Met Val Leu Ser Arg Pro Thr Pro Gln Leu Arg Ala
                245                 250                 255
Glu Val Phe Ile Lys Phe Ile His Val Ala Gln Lys Leu His Gln Leu
                260                 265                 270
Gln Asn Phe Asn Thr Leu Met Ala Val Ile Gly Gly Leu Cys His Ser
        275                 280                 285
Ser Ile Ser Arg Leu Lys Glu Thr Ser Ser His Val Pro His Glu Ile
        290                 295                 300
Asn Lys Val Leu Gly Glu Met Thr Glu Leu Leu Ser Ser Cys Arg Asn
305                 310                 315                 320
Tyr Asp Asn Tyr Arg Arg Ala Tyr Gly Glu Cys Thr His Phe Lys Ile
                325                 330                 335
Pro Ile Leu Gly Val His Leu Lys Asp Leu Ile Ser Leu Tyr Glu Ala
                340                 345                 350
Met Pro Asp Tyr Leu Glu Asp Gly Lys Val Asn Val Gln Lys Leu Leu
                355                 360                 365
Ala Leu Tyr Asn His Ile Asn Glu Leu Val Gln Leu Gln Asp Val Ala
        370                 375                 380
Pro Pro Leu Asp Ala Asn Lys Asp Leu Val His Leu Leu Thr Leu Ser
385                 390                 395                 400
Leu Asp Leu Tyr Tyr Thr Glu Asp Glu Ile Tyr Glu Leu Ser Tyr Ala
                405                 410                 415
Arg Glu Pro Arg Asn His Arg Ala Pro Pro Leu Thr Pro Ser Lys Pro
                420                 425                 430
Pro Val Val Val Asp Trp Ala Ser Gly Val Ser Pro Lys Pro Asp Pro
                435                 440                 445
Lys Thr Ile Ser Lys His Val Gln Arg Met Val Asp Ser Val Phe Lys
                450                 455                 460
Asn Tyr Asp Leu Asp Gln Asp Gly Tyr Ile Ser Gln Glu Glu Phe Glu
465                 470                 475                 480
Lys Ile Ala Ala Ser Phe Pro Phe Ser Phe Cys Val Met Asp Lys Asp
                485                 490                 495
Arg Glu Gly Leu Ile Ser Arg Asp Glu Ile Thr Ala Tyr Phe Met Arg
                500                 505                 510
Ala Ser Ser Ile Tyr Ser Lys Leu Gly Leu Gly Phe Pro His Asn Phe
                515                 520                 525
Gln Glu Thr Thr Tyr Leu Lys Pro Thr Phe Cys Asp Asn Cys Ala Gly
                530                 535                 540
Phe Leu Trp Gly Val Ile Lys Gln Gly Tyr Arg Cys Lys Asp Cys Gly
545                 550                 555                 560
```

-continued

```
Met Asn Cys His Lys Gln Cys Lys Asp Leu Val Val Phe Glu Cys Lys
                565                 570                 575
Lys Arg Ser Lys Ser
            580
```